United States Patent [19]

Tsuda et al.

[11] Patent Number: 4,918,074

[45] Date of Patent: Apr. 17, 1990

[54] POLYAZAHETEROCYCLE COMPOUNDS

[75] Inventors: Yoshinao Tsuda, Tokorozawa; Tadashi Mishina, Iruma; Minoru Obata; Kazuhiko Araki, both of Nakatsu; Jun Inui, Iruma; Tadao Nakamura, Nakatsu, all of Japan

[73] Assignee: Yoshitomi Pharmaceutical Industries, Ltd., Osaka, Japan

[21] Appl. No.: 154,398

[22] Filed: Feb. 10, 1988

Related U.S. Application Data

[60] Continuation-in-part of Ser. No. 137,088, Dec. 23, 1987, abandoned, which is a division of Ser. No. 911,803, Sep. 25, 1986, abandoned, which is a continuation-in-part of Ser. No. 736,725, May 22, 1985, abandoned, and a continuation-in-part of Ser. No. 888,497, Jul. 23, 1986, abandoned, which is a continuation-in-part of Ser. No. 796,479, Oct. 16, 1985, abandoned.

[30] Foreign Application Priority Data

| | | | |
|---|---|---|---|
| Mar. 12, 1984 | [JP] | Japan | 59-47357 |
| May 22, 1984 | [JP] | Japan | 59-104257 |
| Sep. 30, 1985 | [JP] | Japan | 60-218306 |
| Apr. 28, 1986 | [JP] | Japan | 61-98499 |

[51] Int. Cl.[4] .................. C07D 487/04; A61K 31/505

[52] U.S. Cl. .................. 514/258; 544/281; 544/254; 544/263

[58] Field of Search .................. 544/281; 514/258

[56] References Cited

U.S. PATENT DOCUMENTS 3,244,717 4/1966 Wagner .

FOREIGN PATENT DOCUMENTS 0103796 9/1983 European Pat. Off. .
0107619 5/1984 European Pat. Off. .
0114273 8/1984 European Pat. Off. .
0163240 12/1985 European Pat. Off. .
0183848 6/1986 European Pat. Off. .
0076677 10/1970 German Democratic Rep. .

OTHER PUBLICATIONS

G. Auzzi et al., "Il Farmaco, Ed. Sc.", vol. 34, 751–758 (1979).
"Basic Abstracts Journal", Derwent Publications 84–173756/28 (Japanese Patent Appln. (Kokai) 59–95289).

*Primary Examiner*—Anton H. Sutto
*Assistant Examiner*—C. L. Cseh
*Attorney, Agent, or Firm*—Wenderoth, Lind & Ponack

[57] ABSTRACT

A polyazaheterocycle compound of the formula:

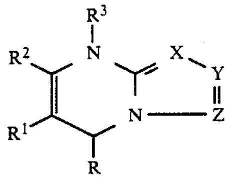

or a pharmaceutically acceptable salt thereof, wherein each symbol is as defined in the specification.

Said compounds exhibit calcium antagonistic and/or calcium agonistic activities.

16 Claims, No Drawings

POLYAZAHETEROCYCLE COMPOUNDS

This is a continuation-in-part of application Ser. No. 137,088, filed Dec. 23, 1987, now abandoned; which is a divisional of application Ser. No. 911,803, filed Sept. 25, 1986, now abandoned; which is a continuation-in-part of both application Ser. No. 736,725, filed May 22, 1985, now abandoned and Ser. No. 888,497, filed Jul. 23, 1986, now abandoned; the latter of which is a continuation-in-part of application Ser. No. 796,479, filed Oct. 16, 1985, now abandoned.

FIELD OF THE INVENTION

The present invention relates to novel and pharmaceutically useful polyazaheterocycle compounds and pharmaceutical composition containing said compounds.

DESCRIPTION OF THE PRIOR ART

It is known that 1,4-dihydropyridine compounds exhibit calcium antagonistic activity and are useful for the treatment of circulatory diseases such as angina pectoris, hypertension or cerebral circulatory disorder. In particular, nifedipine (U.S. Pat. No. 3,485,847) and nicardipine (U.S. Pat. No. 3,985,758) have been widely used as calcium antagonist in clinical field.

Certain fused 1,4-dihydropyridine compounds also have calcium antagonistic activity, such as 4,7-dihydropyrazolo[3,4-b]pyridine-5-carboxylic acid derivatives disclosed in European Patent Application Publications Nos. 107,619 and 114,273.

Further, European Patent Application Publication No. 103,796 discloses 1,4-dihydropyrimidine-5-carboxylic acid derivatives having cardiovascular activity, and Japanese Patent Application laid open under No. 95289/84 (Derwent CPI No. 84-173,756) published on June 1, 1984 discloses 1,2,4-triazolo[1,5-a]pyrimidine compounds with calcium antagonistic activity.

G. Auzzi et al. disclose a method for preparing 2-phenyl-3-chloro/bromo-4,7-dimethyl-4,7-dihydropyrazolo[1,5-a]pyrimidine-6-carboxylic acid in Il-Farmaco, Ed. Sc., vol. 34, 751–758; 1979.

DISCLOSURE OF THE INVENTION

The present invention relates to polyazaheterocycle compounds of the formula:

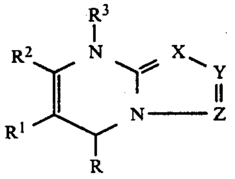

(I)

or a pharmaceutically acceptable salts thereof and pharmaceutical compositions containing said compounds, wherein R is (1) hydrogen, (2) $C_{1-8}$ alkyl, (3) $C_{2-10}$ alkenyl, (4) $C_{2-10}$ alkynyl, (5) aryl, (6) substituted aryl by at least one substituent selected from halogen, amino, nitro, cyano, $C_{1-8}$ alkyl, trifluoromethyl, hydroxy, acylamino, acyl, alkoxycarbonyl and —X'—$R^4$ (wherein X' is oxygen or sulfur and $R^4$ is $C_{1-8}$ alkyl, $C_{2-10}$ alkenyl, $C_{2-10}$ alkynyl, haloalkyl, $C_{3-8}$ cycloalkyl, cycloalkylalkyl, phenyl, substituted phenyl by at least one substituent selected from halogen, nitro, cyano, $C_{1-8}$ alkyl, trifluoromethyl, $C_{1-8}$ alkoxy and hydroxy, aralkyl or substituted aralkyl by on the benzene ring at least one substituent selected from halogen, nitro, cyano, $C_{1-8}$ alkyl, trifluoromethyl, $C_{1-8}$ alkoxy and hydroxy), (7) $C_{3-8}$ cycloalkyl, (8) heteroaryl, (9) substituted heteroaryl, (10) aralkyl, (11) substituted aralkyl, (12) arylalkenyl, (13) substituted arylalkenyl, (14) cycloalkylalkyl, (15) cycloalkylalkenyl, (16) cycloalkylalkynyl, (17) heteroarylalkyl, (18) substituted hetero-arylalkyl, (19) benzoyl, (20) substituted benzoyl, $R^1$ is (1) hydrogen, (2) nitro, (3) cyano, (4) acyl, (5) carbamoyl, (6) mono or di-substituted carbamoyl, (7) thiocarbamoyl, (8) monoor di-substituted thiocarbamoyl, (9) $C_{1-8}$ alkylthiocarbonyl, (10) $C_{1-8}$ alkoxythiocarbonyl, (11) $C_{1-8}$ alkyldithiocarbonyl, or (12) —$COOR^5$ wherein $R^5$ is hydrogen, $C_{1-25}$ alkyl, $C_{2-10}$ alkenyl, $C_{2-10}$ alkynyl, $C_{3-8}$ cycloalkyl, substituted $C_{3-8}$ cycloalkyl by $C_{1-8}$ alkyl, $C_{3-8}$ cycloalkyl-$C_{1-8}$ alkyl, halo-alkyl, $C_{1-8}$ alkoxy-$C_{1-8}$ alkyl, cyano-$C_{1-8}$ alkyl, nitro-$C_{1-8}$ alkyl, hydroxy-$C_{1-8}$ alkyl, acyloxy-$C_{1-8}$ alkyl, amino-$C_{1-8}$ alkyl, substituted amino-$C_{1-8}$ alkyl, amino-$C_{1-8}$ alkoxy-$C_{1-8}$ alkyl, substituted amino-$C_{1-8}$ alkoxy-$C_{1-8}$ alkyl, heteroaryl-$C_{1-8}$ alkyl, alkylthio-$C_{1-8}$ alkyl, alkoxycarbonyl-$C_{1-8}$ alkyl, 2,3-epoxypropyl,

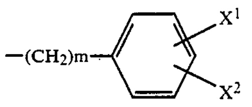

(wherein $X^1$ and $X^2$ are same or different and each is hydrogen, halogen, $C_{1-8}$ alkyl, $C_{1-8}$ alkoxy, nitro, cyano, trifluoromethyl, hydroxy, amino or mono or disubstituted amino, and m is 0 or 1 to 5) or

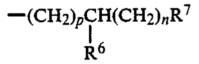

(wherein $R^6$ is phenyl, substituted phenyl by at least one substituent selected from halogen, $C_{1-8}$ alkyl, $C_{1-8}$ alkoxy, nitro, cyano, trifluoromethyl, hydroxy, amino, acylamino and acyl, heteroaryl or substituted heteroaryl, $R^7$ is cyano, hydroxy, nitro, $C_{1-8}$ alkoxy, amino, substituted amino, acyloxy, amino-$C_{1-8}$ alkoxy, substituted amino-$C_{1-8}$ alkoxy, heteroaryl or $C_{1-8}$ alkoxycarbonyl, and each of n and p is 0 or 1 to 4); $R^2$ is (1) halogen, (2) cyano, (3) $C_{1-8}$ alkyl, (4) haloalkyl, (5) hydroxyalkyl, (6) acyloxyalkyl, (7) alkoxyalkyl, (8) dialkoxyalkyl, (9) aminoalkyl, (10) acylaminoalkyl, (11) formyl, (12) carbamoyloxyalkyl, (13) thiocarbamoyloxyalkyl, (14) amino, (15) substituted amino, (16) aralkyloxyalkyl, (17) aryloxyalkyl, (18) hydroxyiminomethyl, (19) hydroxyalkoxyalkyl, (20) aminoalkoxyalkyl, (21) substituted aminoalkoxyalkyl, (22) $C_{3-8}$ cycloalkyl, (23) cycloalkylalkyl, (24) phenyl, (25) substituted phenyl by at least one substituent selected from halogen, $C_{1-8}$ alkyl, $C_{1-8}$ alkoxy, nitro, cyano, hydroxy, amino and trifluoromethyl, (26) aralkyl, or (27) substituted aralkyl by at least one substituent selected from halogen, $C_{1-8}$ alkyl, $C_{1-8}$ alkoxy, nitro and trifluoromethyl; $R^3$ is (1) hydrogen, (2) $C_{1-8}$ alkyl, (3) haloalkyl, (4) hydroxyalkyl, (5) alkoxyalkyl, (6) alkoxycarbonyl, (7) aminoalkyl, (8) substituted aminoalkyl, (9) acyl, (10) heteroaroyl, (11) arenesulfonyloxyalkyl, (12) alkanesulfonyloxyalkyl, (13) aralkyl, or (14) substituted aralkyl by on the benzene ring at least one substituent selected from halogen, $C_{1-8}$ alkyl, $C_{1-8}$ alkoxy, cyano, nitro and trifluoromethyl; and at least one of X, Y and Z is N, and other(s) is (are) C-$R^8$, wherein $R^8$ is (1) hydrogen, (2) halogen, (3) nitro, (4) amino, (5) acylamino, (6) $C_{1-8}$ alkyl, (7) $C_{3-8}$ cycloalkyl, (8) cyano, (9) carboxyl, (10) alkoxycarbonyl, (11) carbamoyl, (12) mono or di-substituted carbamoyl, (13) formyl, (14) hydroxyalkyl, (15) aminoalkyl, (16) acyl, (17) haloalkyl, (18) $C_{2-10}$ alkenyl, (19) $C_{2-10}$ alkynyl, (20) cycloalkylalkyl, (21) alkoxyalkyl, (22) acyloxyalkyl, (23) cyanoalkyl, (24) nitroalkyl, (25) carbamoyloxyalkyl, (26) thiocarbamoyloxyalkyl, (27) aralkyloxy, (28) aralkylthio, (29) alkylthio, (30) $C_{1-8}$ alkoxy, or (31) aralkyl; with the following provisos: (1) when two of X, Y and Z are C-$R^8$, two of $R^8$ are the same or different and each is as defined above, (2) when X and Z are N, $R^2$ is not halogen, amino or substituted amino, and (3) when only X is N, $R^8$ is not nitro, amino, $C_{1-8}$ alkyl, carboxyl, formyl, hydroxylalkyl, aminoalkyl, alkoxyalkyl, acyloxyalkyl, nitroalkyl, aralkyloxy, aralkylthio, alkylthio or $C_{1-8}$ alkoxy.

More specifically stated with the aforementioned generic formula, $C_{1-8}$ alkyl includes, e.g. methyl, ethyl, propyl, isopropyl, butyl, sec-butyl, tert-butyl, pentyl, neopentyl, 1-ethylpropyl, 1-methylbutyl, tert-pentyl, hexyl, heptyl, octyl, etc.; $C_{2-10}$ alkenyl includes, e.g. vinyl, 2-propenyl, 2-butenyl, 3-butenyl, 1-methyl-2-propenyl, 2-methyl-2-propenyl, 2-pentenyl, 1-methyl-2-butenyl, 1-ethyl-2-propenyl, 1,1-dimethyl-2-propenyl, 3-methyl-2-butenyl, geranyl, etc.; $C_{2-10}$ alkynyl includes, e.g. ethynyl, propargyl, propynyl, 2-butynyl, 1-methyl-2-propynyl, 2-pentynyl, 1-ethyl-2-propynyl, 1,1-dimethyl-2-propynyl, etc.; aryl includes, e.g. phenyl, naphthyl, anthranyl, etc.; halogen includes fluorine, chlorine, bromine, iodine; (mono or di-substituted) amino includes, e.g. amino, methylamino, ethylamino, propylamino, dimethylamino, diethylamino, dipropylamino, 1-pyrrolidinyl, piperidino, morpholino, 1-piperazinyl, 4-methyl-piperazinlyl, N-methyl-N-benzylamino, etc.; acylamino includes, e.g. acetylamino, propionylamino, butyrylamino, isobutyrylamino, N-methylacetylamino, benzoylamino, etc.; acyl includes, e.g. acetyl, propionyl, butyryl, isobutyryl, benzoyl, etc.; alkoxycarbonyl includes, e.g. methoxycarbonyl, ethoxycarbonyl, propoxycarbonyl, isopropoxycarbonyl, butoxycarbonyl, etc.; haloalkyl includes, e.g. fluoromethyl, bromomethyl, iodomethyl, trifluoromethyl, fluoroethyl, trifluorothyl, chloromethyl, chloroethyl, chloropropyl, bromopropyl, difluoromethyl, dichloromethyl, dibromomethyl, difluoroethyl, trifluoropropyl, trifluorobutyl, iodoethyl, chlorobutyl, fluorobutyl, etc.; $C_{3-8}$ cycloalkyl includes, e.g. cyclopropyl, cyclobutyl, cyclopentyl, cyclohexyl, cycloheptyl, etc.; cycloalkylalkyl includes, e.g. cyclopropymethyl, cyclobutylmethyl, cyclopropylethyl, cyclopentylmethyl, cyclohexylmethyl, cyclopentylethyl, cycloheptylmethyl, cyclohexylethyl, cyclopentylbutyl, cyclohexylpropyl, cyclopropylbutyl, etc.; $C_{1-8}$ alkoxy includes, e.g. methoxy, ethoxy, propoxy, isopropoxy, butoxy, etc.; aralkyl includes, e.g. benzyl, phenylethyl, phenylpropyl, etc.; heteroaryl includes, e.g. pyridyl, thienyl, furyl, pyryl, quinolyl, isoquinolyl, pyrimidinyl, pyridazinyl, quinazolyl, quinoxalyl, benzothienyl, pyrazolyl, imidazolyl, triazolyl, oxadiazolyl, pyrazinyl, thiazolyl, oxazolyl, isothiazolyl, isoxazolyl, thiadiazolyl, indolizinyl, indolyl, benzofuranyl, indazolyl, benzothienyl, benzimidazolyl, benzoxazolyl, benzisoxazolyl, benzthiazolyl, benztriazolyl, 2,1,3-benzoxadiazolyl, cinnolyl, phthalazynyl, naphthyri-dinyl, benztriazinyl, etc.; arylalkenyl includes, e.g. styryl, cinnamyl, phenylbutenyl, etc.; arylalkynyl includes, e.g. phenylpropynyl, phenylbutynyl, etc.; mono or di-substituted carbamoyl includes, e.g. N-methylcarbamoyl, N-ethylcarbamoyl, N-propylcarbamoyl, N-butylcarbamoyl, N,N-dimethylcarbamoyl, N,N-diethylcarbamoyl, N-isopropylcarbamoyl, N-hexylcarbamoyl, N-methyl-N-benzylcarbamoyl, N-benzylcarbamoyl, N-phenylcarbamoyl, pyrrolidinylcarbamoyl, piperidinocarbamoyl, morpholinocarbamoyl, N-tert-butylcarbamoyl, N-cyclopentylcarbamoyl, etc.; mono or di-substituted thiocarbamoyl includes, e.g. N-methylthiocarbamoyl, N-ethylthiocarbamoyl, N-propylthiocarbamoyl, N-butylthiocarbamoyl, N,N-dimethylthiocarbamoyl, N,N-diethylthiocarbamoyl, N-isopropylthiocarbamoyl, N-methyl-N-benzylthiocarbamoyl, N-benzylthiocarbamoyl, N-phenylthiocarbamoyl, pyrrolidinylthiocarbamoyl, piperidino-thiocarbamoyl, morpholinothiocarbamoyl, S-methylthiocarbamoyl, S-ethylthiocarbamoyl, S-propylthiocarbamoyl, S-butylthiocarbamoyl, S-isopropylthiocarbamoyl, S-benzylthiocarbamoyl, S-phenylthiocarbamoyl, N-tert-butylthiocarbamoyl, S-tert-butylthiocarbamoyl, N-cyclopentylthiocarbamoyl, S-cyclopentylthiocarbamoyl, etc.; $C_{1-8}$ alkylthiocarbonyl includes, e.g. methylthiocarbonyl, ethylthiocarbonyl, propylthiocarbonyl, isopropylthiocarbonyl, butylthiocarbonyl, isobutylthiocarbonyl, sec-butylthiocarbonyl, tert-butylthiocarbonyl, pentylthiocarbonyl, etc.; $C_{1-8}$ alkoxythiocarbonyl includes, e.g. methoxythiocarbonyl, ethoxythiocarbonyl, propoxythiocarbonyl, isopropoxythiocarbonyl, butoxythiocarbonyl, tert-butoxythiocarbonyl, cyclopentyloxythiocarbonyl, etc.; $C_{1-8}$ alkyldithiocarbonyl includes, e.g. methyldithiocarbonyl, ethyldithiocarbonyl, propyldithiocarbonyl, isopropyldithiocarbonyl, butyldithiocarbonyl, tert-butyldithiocarbonyl, cyclopentyldithiocarbonyl, etc.; $C_{1-25}$ alkyl includes, e.g. methyl, ethyl, propyl, isopropyl, butyl, isobutyl, sec-butyl, tert-butyl, pentyl, neopentyl, 1-ethylpropyl, 1-methylbutyl, tert-pentyl, hexyl, heptyl, octyl, decyl, cetyl, stearyl, behenyl, etc.; amino-$C_{1-8}$ alkyl includes, e.g. aminomethyl, methylaminomethyl, ethylaminomethyl, propylaminomethyl, isopropylaminomethyl, dimethylaminomethyl, diethylaminomethyl, dipropylaminomethyl, pyrrolidinylmethyl, piperidinomethyl, morpholinomethyl, 4-methylpiperazin-1-ylmethyl, N-methyl-N-benzylaminomethyl, 2-aminoethyl, 2-methylaminoethyl, 2-ethylaminoethyl, 2-propylaminoethyl, 2-dimethylaminoethyl, 2-diethylaminoethyl, 2-dipropylaminoethyl, 2-(1-pyrrolidinyl)ethyl, 2-piperidinoethyl, 2-morpholinoethyl, 2-(1-piperazinyl)ethyl, 2-(4-methylpiperazin-1-yl)ethyl, 2-(N-methyl-N-benzylamino)ethyl, 2-diethylamino-1-methylethyl, 2-piperidino-1-methylethyl, 2-(N-methyl-N-benzylamino)-1-methylethyl, 2-piperidino-1,1-dimethylethyl, 3-diethylaminopropyl, 3-piperidinopropyl, 3-(N-methyl-N-benzylamino)propyl, 3-morpholinopropyl, 4-dimethylaminobutyl, 4-diethylaminobutyl, 4-piperidinobutyl, 4-(2-methoxyphenyl)piperazin-1-ylmethyl, N-methyl-N-[2-(3,4-dimethoxyphenyl)ethyl]aminoethyl, N-[2-(3,4-dimethoxyphenyl)ethyl]aminomethyl, N-methyl-N-[2-(3,4-dihydroxyphenyl)ethyl]aminomethyl, etc.; alkylthio-$C_{1-8}$ alkyl includes, e.g. 2-methylthioethyl, 2-ethylthioethyl, 2-propylthioethyl, 2-isopropylthioethyl, 3-methylthiobutyl, 3-ethylthiobutyl, 2-methylthio-1-methylethyl, 2-methylthio-1,1-dimethylethyl, etc.; alkoxycarbonyl-$C_{1-8}$ alkyl includes, e.g. methoxycarbonylmethyl, ethoxycarbonylmethyl, propoxycarbonylmethyl, isopropoxycarbonylmethyl, 2-methoxycarbonylethyl, 2-ethoxycarbonylethyl, 1-methoxycarbonylethyl, 1-ethoxycarbonylethyl, 1-methoxycarbonyl-1-methylethyl, 1-ethoxycarbonyl-1-methylethyl, etc.; hydroxyalkyl includes, e.g. hydroxymethyl, hydroxyethyl, hydroxypropyl, hydroxybutyl, etc.; acyloxyalkyl includes, e.g. acetoxymethyl, acetoxyethyl, acetoxypropyl, acetoxybutyl, propionyloxymethyl, butyryloxymethyl, isobutyryloxymethyl, benzoyloxymethyl, etc.; alkoxyalkyl includes, e.g. methoxymethyl, ethoxymethyl, propoxymethyl, isopropoxymethyl, butoxymethyl, methoxyethyl, methoxypropyl, methoxybutyl, propoxypropyl, isopropoxymethyl, etc.; dialkoxyalkyl includes, e.g. dimethoxymethyl, diethoxymethyl, dipropoxymethyl, dibutoxymethyl, etc.; acylaminoalkyl includes, e.g. acetylaminomethyl, acetylaminoethyl, acetylaminopropyl, acetylaminobutyl, acetylaminopentyl, propionylaminomethyl, butyrylaminomethyl, isobutyrylaminoethyl, N-methylacetylaminomethyl, etc.; carbamoyloxyalkyl includes, e.g. carbamoyloxymethyl, carbamoyloxyethyl, carbamoyloxypropyl, cabamoyloxybutyl, N-methylcarbamoyloxymethyl, N-ethylcarbamoyloxymethyl, N-propylcarbamoyloxymethyl, N-butylcarbamoyloxymethyl, N-methylcarbamoyloxyethyl, N-methylcarbamoyloxypropyl, N-methylcarbamoyloxybutyl, N,N-dimethylcarbamoyloxymethyl, N,N-diethylcarbamoyloxyethyl, piperidinocarbonyloxymethyl, etc.; thiocarbamoyloxyalkyl includes, e.g. thiocarbamoyloxymethyl, thiocarbamoyloxyethyl, thiocarbamoyloxypropyl, thiocarbamoyloxybutyl, N-methylthiocarbamoyloxymethyl, N-ethylthiocarbamoyloxymethyl, N-propylthiocarbamoyloxymethyl, N-butylthiocarbamoyloxymethyl, N-methylthiocarbamoyloxyethyl, N-methylthiocarbamoyloxypropyl, N-methylthiocarbamoyloxybutyl, N,N-dimethylthiocarbamoyloxymethyl, N,N-diethylthiocarbamoyloxyethyl, piperidinothiocarbonyloxymethyl, etc.; substituted amino includes, e.g. methylamino, ethylamino, propylamino, dimethylamino, diethylamino, dipropylamino, 1-pyrrolidinyl, piperidino, morpholino, 1-piperazinyl, 4-methylpiperazin-1-yl, N-methyl-N-benzylamino, etc.; aralkyloxyalkyl includes, e.g. benzyloxymethyl, benzyloxyethyl, benzyloxypropyl, etc.; aryloxyalkyl includes, e.g. phenoxymethyl, phenoxyethyl, phenoxypropyl, tolyloxymethyl, tolyloxyethyl, tolyloxypropyl, tolyloxybutyl, xylyloxymethyl, xylyloxyethyl, xylyloxypropyl, etc.; hydroxyalkoxyalkyl includes, e.g. hydroxyethoxymethyl, hydroxyethoxyethyl, hydroxyethoxypropyl, hydroxyethoxybutyl, hydroxypropoxymethyl, hydroxybutoxymethyl, etc.; aminoalkoxyalkyl includes, e.g. aminoethoxymethyl, aminoethoxyethyl, aminoethoxypropyl, aminoethoxybutyl, aminopropoxymethyl, aminobutoxymethyl, etc.; substituted aminoalkoxyalkyl includes, e.g. N-methylaminoethoxymethyl, N-methylaminoethoxyethyl, N-butylaminoethoxypropyl, N,N-dimethylaminoethoxybutyl, N-benzylaminopropoxymethyl, N-methyl-N-benzylaminobutoxymethyl, pyrrolidinoethoxymethyl, piperidinoethoxyethyl, morpholinoethoxypropyl, etc.; heteroaroyl includes, e.g. furoyl, thenoyl, nicotinoyl, isonicotinoyl, etc.; arenesulfonyloxyalkyl includes, e.g. tosyloxyethyl, tosyloxypropyl, tosyloxybutyl, etc.; alkanesulfonyloxyalkyl includes, e.g. mesyloxyethyl, mesyloxypropyl, mesyloxybutyl, etc.; cyanoalkyl includes, e.g. cyanomethyl, cyanoethyl, cyanopropyl, cyanobutyl, etc.; nitroalkyl includes, e.g. nitromethyl, nitroethyl, nitropropyl, nitrobutyl, etc.; aralkyloxy includes, e.g. benzyloxy, phenylethyloxy, phenylpropyloxy, phenylbutyloxy, etc.; aralkylthio includes, e.g. benzylthio, phenylethylthio, phenylpropylthio, etc.; alkylthio includes, e.g. methylthio, ethylthio, propylthio, isopropylthio, butylthio, pentylthio, hexylthio, heptylthio, octylthio, etc.; and substituent includes, e.g. halogen, amino, nitro, cyano, $C_{1-8}$ alkyl, trifluoromethyl, hydroxy, $C_{1-8}$ alkoxy, haloalkyl, etc.

The ring in the formula (I) and in the specification of the present invention represented by the formula:

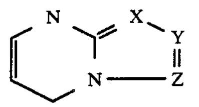

means a 4,7-dihydrotetrazolo[1,5-a]pyrimidine of the formula (a):

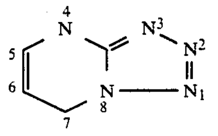

a 4,7-dihydro-1,2,4-triazolo[1,5-a]pyrimidine of the formula (b):

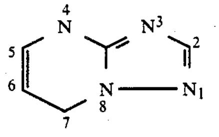

a 4,7-dihydro-1,2,3-triazolo[1,5-a]pyrimidine of the formula (c):

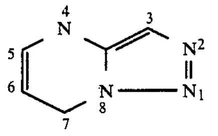

a 5,8-dihydroimidazo[1,2-a]pyrimidine of the formula (d):

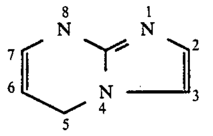

a 1,4-dihydroimidazo[1,5-a]pyrimidine of the formula (e):

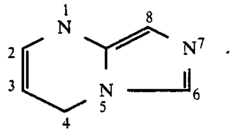

or a 4,7-dihydropyrazolo[1,5-a]pyrimidine of the formula (f):

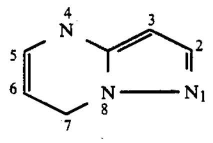

The compounds of formula (I) of the present invention can be, for example, prepared by the following methods.

(1) A method which comprises subjecting a compound of the formula:

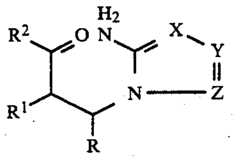

(II)

to dehydration condensation at room temperature or under heating in a suitable solvent or without it.

(2) A method which comprises subjecting a compound of the formula:

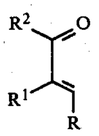

(III)

to condensation with a compound of the formula:

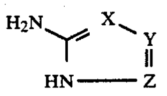

(IV)

at room temperature or under heating in a suitable solvent or without it.

(3) A method which comprises subjecting a compound of the formula:

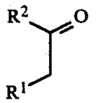

(V)

to dehydration condensation with a compound of the formula:

R—CHO (VI)

at room temperature or under heating in a suitable solvent or without it, if necessary in the presence of a suitable acid catalyst, a base catalyst or both, and then subjecting the compound obtained to condensation with a compound of the formula (IV) at room temperature or under heating in a suitable solvent or without it.

(4) A method which comprises reacting a compound of the formula:

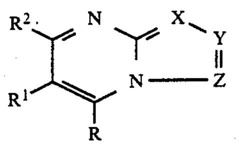

(VII)

with hydrogen gas in the presence of a suitable metal catalyst or a complex metal hydride (e.g. lithium aluminum hydride or sodium borohydride) at room temperature or under heating in a suitable solvent or without it.

(5) A method which comprises converting the substituents R, $R^1$, $R^2$ and $R^8$ of the compound obtained by the abovementioned methods (1)-(4) according to usual manners of organic chemical synthesis.

The compounds of the formula (I) wherein $R^3$ is the substituent other than hydrogen can, for example, be prepared by the following method.

(6) A method which comprises reacting a compound of the formula:

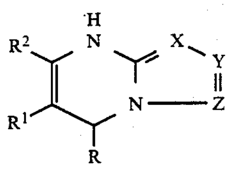

(VIII)

with a compound of the formula:

$R^3$—Y (IX)

wherein Y is halogen (e.g. chlorine, bromine or iodine) or active ester group (e.g. methanesulfonyloxy, toluenesulfonyloxy or trifluoromethanesulfonyloxy) in a suitable solvent in the presence of a suitable inorganic base (e.g. sodium hydride, sodium amide, sodium methoxide, sodium hydroxide or potassium carbonate) or a suitable organic base (e.g. triethylamine or diisopropylethylamine).

(7) A method which comprises converting the substituents R, $R^1$, $R^2$ and $R^8$ of the compound obtained by the abovementioned methods (6) according to usual manners of organic chemical synthesis.

Any inert solvent can be employed as a suitable solvent in the methods (1)-(4) and (6), and includes, for example, a lower alkanol (e.g. methanol, ethanol, propanol, isopropanol, butanol, tert-butanol or ethylene glycol), an aromatic hydrocarbon (e.g. benzene, toluene or xylene), an ether (e.g. diethyl ether, diisopropyl ether, dimethoxyethane, diethylene glycol dimethyl ether, tetrahydrofuran or dioxane), a halogenated lower alkane (e.g. dichloromethane, dichloroethane, chloroform or tetrachloromethane), an acid amide (e.g. dimethylformamide, N-methylpyrrolidone or hexamethylphosphorotriamide), a lower alkanecarboxylic acid or an ester thereof (e.g. formic acid, acetic acid, propionic acid, methyl acetate, ethyl acetate, butyl acetate or methyl propionate), a nitrated lower alkane (e.g. nitromethane or nitroethane), dimethylsulfoxide, sulforane, water, or a mixture thereof.

The reactions of the methods (1)-(4) perform at a temperature under 200° C., and preferably at temperature of from room temperature to 150° C.

The usual manners of organic chemical synthesis in the methods (5) and (7) include, for example, substitution reaction with an electrophilic reagent (e.g. Mannich reaction, Vilsmeyer reaction, Friedel-Crafts reaction, formation of methylol, halogenation or nitration); reduction reaction (e.g. reduction of nitro to amino, reduction of a cyano to an aminomethyl, reduction of a carboxylic acid or its ester to a methylol, or reduction of an aldehyde or a ketone to an alcohol); hydrolysis reaction (e.g. hydrolysis of an ester, hydrolysis of an acetal or a ketal, or hydrolysis of an amide or a nitrile); hydrogenolysis; decarboxylation; substitution reaction via a diazonium salt (e.g. Sandmeyer reaction or Schiemann reaction); substitution reaction with a nucleophilic agent (e.g. amination, acetoxylation, halogenation, cyanation, alkoxylation, formation of thioether or thioester, formation of an azide or carbon-carbon bond formation using a carbanion); esterification; thioesterification; transesterification; acylation; sulfonylation; formation of alkylcarbamoyl; formation of alkylthiocarbamoyl; dehydration of an amide to a nitrile; dehydration of an alcohol or a halide to an olefine; rearrangement of an acid azide or an acid amide to an amino derivative; rearrangement of an oxime to an amino derivative; halogenation of an alkyl carbon; and formation of an iminoether from a nitrile.

The compound of formula (I) having an asymmetric carbon atom can be prepared as a racemate or an optically active isomer. The racemate can be divided into a desired optical isomer by means of, for example, a fractional recrystallization of a salt with an optically active base or acid; passing through the column filled with an optically active carrier; producing an ester bond or amide bond with an optically active amine, alcohol or carboxylic acid, and then separating the formed diastereomer by using a fractional recrystallization or column chromatography; carring out the synthetic methodsof (1), (2) and (3) using the starting compounds (the compounds of formulas (II), (III), (IV), (V), (VI) and so on), which are combined with an optically active amine, alcohol or carboxylic acid; or reducing the starting compound using an asymmetric reduction reagent or asymmetric reduction catalyst in the synthetic method (4). Furthermore, the compounds of formula (I) having at least two asymmetric carbon atoms can be prepared as an individual diastereomer or a mixture thereof. The optical isomers thus obtained can be led to the optically active compounds of the present invention by the synthetic method (7). The individual diastereomer can be purified by means of fractional recrystallization or chromatography. In the compound (I) having an oxime of the present invention, syn- and anti-isomers can exist. The compounds of the present invention also include the syn- and anti-forms.

The compounds of the formula (I), optical isomers thereof or diasteromers thereof can, if desired, be converted into acid addition salts thereof with an inorganic acid (e.g. hydrochloric acid, hydrobromic acid, sulfuric acid or phosphoric acid), an organic acid (e.g. acetic acid, propionic acid, glycollic acid, succinic acid, maleic acid, fumaric acid, malic acid, tartaric acid, oxalic acid, citric acid, benzoic acid, cinnamic acid, mandelic acid, salicylic acid, 2-acetoxybenzoic acid, nicotinic acid or isonicotinic acid), an organic sulfonic acid (e.g. methanesulfonic acid, ethanesulfonic acid, 2-hydroxyethanesulfonic acid, benzenesulfonic acid, p-toluenesulfonic acid or naphthalene-2-sulfonic acid), ascorbic acid, lysine or glutamic acid. Furthermore, the compounds (1) having a carboxyl group can also be converted into metal salts thereof (e.g. sodium salt, potassium salt or aluminum salt) or salts with amines (e.g. a salt with triethylamine).

The compounds of the present invention clearly exhibited not only an increase in coronary blood flow and vertebral blood flow but also cardiotonic activity associated with mild hypotension by intravenous or intraduodenal administration to the anesthetized dogs. These compounds, however, did not influence heart rate. They also increased renal blood flow and exhibited diuretic activity. In the isolated myocardium, the compounds of the present invention prolonged the duration of action potential.

Furthermore, the present inventors have found that the compounds of the present invention have shown calcium antagonistic and/or calcium agonistic activities depending upon the concentrations of extracellular potassium ion in cardiac muscle and blood vessel. Several compounds showed the organ-selective calcium antagonist and agonist activity, i.e., calcium antagonist in vascular system and calcium agonist in myocardium. Since the compounds possessing these specific pharmacological activities, they seem to be desirable as drugs for the treatment of ischemic heart disease (coronary vasodilators), heart failure (cardiotonics), arrhythmia and the prophylaxis or the treatment of myocardial infarction. In addition, the compounds of the present invention are recognized to have ideal characteristics to treat and improve the multiple cardiovascular disfunction, especially resulted from aging. Furthermore, for cerebral diseases, the compounds of the present invention are ideal because they preferrentially increased the blood flow of damaged cerebral region with less steal phenomena in acute or chronic phases due to its dependency on extracellular potassium concentration. From the above-mentioned effects in brain, heart and kidney, it can be understood that the compounds of the present invention are also sufficient as mild anti-hypertensive agents with increasing the blood flow in such vital organs as the heart, brain and kidney. Moreover, the comounds of the present invention can be applied as pressor or anti-shock agents.

The following pharmacological experiments explain the effects of the compounds according to the present invention in more detail. The test compounds employed are as follows:

Compound (1): 6-Ethoxycarbonyl-5-methyl-7-(2-trifluoromethylphenyl)-4,7-dihydropyrazolo[1,5-a]pyrimidine Compound (2): 1-Phenyl-2-piperidinoethyl 5-methyl-7-(3-nitrophenyl)-4,7-dihydropyrazolo[1,5-a]pyrimidine-6-carboxylate (β-form of diastereomer)

Compound (3): 6-Butoxycarbonyl-5-methyl-7-(2-trifluoromethylphenyl)-4,7-dihydropyrazolo[1,5-a]pyrimidine Compound (4): 7-(2-Chlorophenyl)-6-ethoxycarbonyl-5-methyl-4,7-dihydropyrazolo[1,5-a]pyrimidine Compound (5): 6-Ethoxycarbonyl-5-hydroxymethyl-7-(2-trifluoromethylphenyl)-4,7-dihydropyrazolo[1,5-a]pyrimidine Compound (6): 6-Cyclopropylmethyloxycarbonyl-5-methyl-7-(2-trifluoromethylphenyl)-4,7-dihydropyrazolo[1,5-a]pyrimidine Compound (7): 3-Cyano-6-cyclopropylmethyloxycarbonyl-5-methyl-7-(2-trifluoromethylphenyl)-4,7-dihydropyrazolo[1,5-a]pyrimidine Compound (8): 1-Phenyl-2-methoxyethyl 5-methyl-7-(2-trifluoromethylphenyl)-4,7-dihydropyrazolo[1,5-a]pyrimidine-6-carboxylate (β-form of diastereomer)

Compound (9): 1-Phenyl-2-methoxyethyl 5-methyl-7-(2-trifluoromethylphenyl)-4,7-dihydropyrazolo[1,5-a]pyrimidine-6-carboxylate (α-form of diastereomer)

Compound (10): 6-Isopropoxycarbonyl-5-methyl-7-(2-trifluoromethylphenyl)-4,7-dihydropyrazolo[1,5-a]pyrimidine Compound (11): 5-Methyl-6-propoxycarbonyl-7-(2-trifluoromethylphenyl)-4,7-dihydropyrazolo[1,5-a]pyrimidine Compound (12): 6-Isobutoxycarbonyl-5-methyl-7-(2-trifluoromethylphenyl)-4,7-dihydropyrazolo[1,5-a]pyrimidine Compound (13): 6-tert-Butoxycarbonyl-5-methyl-7-(2-trifluoromethylphenyl)-4,7-dihydropyrazolo[1,5-a]pyrimidine Compound (14): 3-Cyano-6-ethoxycarbonyl-5-methyl-7-(2-trifluoromethylphenyl)-4,7-dihydropyrazolo[1,5-a]pyrimidine Compound (15): 6-Cyclopentyloxycarbonyl-5-methyl-7-(2-trifluoromethylphenyl)-4,7-dihydropyrazolo[1,5-a]pyrimidine Compound (16): 3-Chloro-6-ethoxycarbonyl-5-methyl-7-(2-trifluoromethylphenyl)-4,7-dihydropyrazolo[1,5-a]pyrimidine Compound (17): 7-(2-Benzylthiophenyl)-6-ethoxycarbonyl-5-methyl-4,7-dihydropyrazolo[1,5-a]pyrimidine Compound (18): 7-(2-Difluoromethoxyphenyl)-6-ethoxycarbonyl-5-methyl-4,7-dihydropyrazolo[1,5-a]pyrimidine Compound (19): 6-[2-(3,4-Dimethoxyphenyl)ethyl]oxycarbonyl-5-methyl-7-(2-trifluoromethylphenyl)-4,7-dihydropyrazolo[1,5-a]pyrimidine Compound (20): 6-Ethoxycarbonyl-5-methyl-7-(2-trifluoromethylphenyl)-4,7-dihydropyrazolo[1,5-a]pyrimidine, optical isomer (−)

Compound (21): 6-Ethoxycarbonyl-5-methyl-7-(2-trifluoromethylphenyl)-4,7-dihydrotetrazolo[1,5-a]pyrimidine Compound (22): 5-Methyl-6-(3-pentyloxycarbonyl)-7-(2-trifluoromethylphenyl)-4,7-dihydropyrazolo[1,5-a]pyrimidine Compound (23): 7-(2-Fluorophenyl)-6-isopropoxycarbonyl-5-methyl-4,7-dihydropyrazolo[1,5-a]pyrimidine Compound (24): 6-Ethoxycarbonyl-5-fluoromethyl-7-(2-trifluoromethylphenyl)-4,7-dihydropyrazolo[1,5-a]pyrimidine Compound (25): 6-Cyclopentyloxycarbonyl-7-(2-fluorophenyl)-5-methyl-4,7-dihydropyrazolo[1,5-a]pyrimidine Compound (26): 7-(2-Chlorophenyl)-6-isopropoxycarbonyl-5-methyl-4,7-dihydropyrazolo[1,5-a]pyrimidine Compound (27): 7-(2-Bromophenyl)-6-isopropoxycarbonyl-5-methyl-4,7-dihydropyrazolo[1,5-a]pyrimidine Compound (28): 7-(2,3-Dichlorophenyl)-6-isopropoxycarbonyl-5-methyl-4,7-dihydropyrazolo[1,5-a]pyrimidine Compound (29): 3-Cyano-7-(2-fluorophenyl)-6-isopropoxycarbonyl-5-methyl-4,7-dihydropyrazolo[1,5-a]pyrimidine Compound (30): 6-Isopropoxycarbonyl-5-methyl-7-(2-methylphenyl)-4,7-dihydropyrazolo[1,5-a]pyrimidine Compound (31): 7-(2,3-Difluorophenyl)-6-isopropoxycarbonyl-5-methyl-4,7-dihydropyrazolo[1,5-a]pyrimidine Compound (32): 7-(2,5-Difluorophenyl)-6-isopropoxycarbonyl-5-methyl-4,7-dihydropyrazolo[1,5-a]pyrimidine Compound (33): 7-(2-Chloro-3-fluorophenyl)-6-isopropoxycarbonyl-5-methyl-4,7-dihydropyrazolo[1,5-a]pyrimidine Compound (34): 1-Phenyl-2-piperidinoethyl 7-methyl-5-(3-nitrophenyl)-5,8-dihydroimidazo[1,2-a]pyrimidine-6-carboxylate (β-form of diastereomer)

Compound (35): 3-Cyano-7-(2,3-difluorophenyl)-6-isopropoxycarbonyl-5-methyl-4,7-dihydropyrazolo[1,5-a]pyrimidine

I. CA$^{2+}$-ANTAGONIST, CA$^{2+}$-AGONIST, PARTIAL CA$^{2+}$-AGONIST AND ANTAGONIST ACTIVITY

1. Methods

Dogs of either sex were anesthetized with sodium pentobarbital (30 mg/kg i.v.). Heparin (500 U/kg i.v.) was administered before making preparation. Under artificial respiration (18 strokes/min, 20 ml/kg tidal volume), left ventricular dp/dt max, and left coronary blood flow were measured (1). Test compounds were injected into the left coronary artery in a volume of 10 or 30 μl. The effects of compounds on coronary blood flow were observed and presented generally as $ED_{50}$, a dose required to increase coronary blood flow by a half of the effects of nifedipine (3 μg). Similarly, the effects on dp/dt max were observed and shown as $ED_{30}$, a dose required to increase dp/dt max by 30% of the efffects of isoproterenol (0.1 μg).

(1) Yago, N.: Folia pharmacol. japon 57, 380 (1961)

2. Results

All the compounds could be classified into three groups according to their pharmacological properties.

(i) Ca$^{2+}$-antagonist

The compounds of this group showed coronary vasodilating activity, but had little effect on contraction of the heart.

| Compounds | Increase in CBF $ED_{50}$ (μg) | Increase in dp/dt max $ED_{30}$ (μg) |
|---|---|---|
| (2) | 1.5 | >10 |
| (7) | 2.0 | >30 |
| (12) | 1.8 | >300 |
| (14) | 1.6 | >100 |
| (29) | 1.0 | >30 |
| (31) | 1.4 | >30 |
| (33) | 1.4 | >30 |
| (34) | 10.0 | >30 |
| (35) | 0.28 | >30 |

*CBF; coronary blood flow (ii) Ca$^{2+}$-agonist

The compounds of this group showed both coronary vasoconstricting and cardiotonic activity in the heart.

| Compounds | Decrease in CBF $ED_{-50}$ (μg) | Increase in dp/dt max $ED_{30}$ (μg) |
|---|---|---|
| (17) | 1.1 | 6.7 |
| (19) | 1.2 | 14 |
| (24) | >300 | 86 |

*CBF; coronary blood flow

**$ED_{-50}$; dose required to decrease CBF by 50% from basal value (iii) Partial Ca$^{2+}$-agonist and antagonist The compounds of this group showed both coronary vasodilating and cardiotonic activity.

| Compounds | Increase in CBF $ED_{50}$ (μg) | Increase in dp/dt max $ED_{30}$ (μg) |
|---|---|---|
| (10) | 5.7 | 71 |
| (13) | 22 | 70 |
| (15) | 1.8 | 198 |
| (23) | 15 | 71 |
| (25) | 28 | 164 |
| (26) | 13 | 133 |
| (27) | 7 | 103 |
| (32) | 8 | 93 |

*CBF; coronary blood flow

Pharmacological characteristics of the compounds were studied in following experiments.

II. EFFECTS ON CARDIAC FUNCTION AND HEMODYNAMICS IN THE ANESTHETIZED DOG

1. Methods

Adult mongrel dogs were anesthetized with sodium pentobarbital (30 mg/kg i.v.). Effects of test compounds on arterial blood pressure, coronary arterial blood flow, vertebral blood flow, renal blood flow, left ventricular dp/dt max (dp/dt max) and urine volume were observed. The compounds were administered intravenously (i.v.) or intraduodenally (i.d.).

2. Results (i) Hypotensive effects:

When the following compounds were administered intravenously, they effectively lowered blood pressure by over 20% from control.

| Compounds | Dose (μg/kg) | Hypotensive effect (%) |
|---|---|---|
| (2) | 30 | 37 |
| (7) | 10 | 20 |
| (10) | 300 | 31 |
| (14) | 10 | 20 |
| (15) | 300 | 20 |
| (16) | 300 | 29 |
| (20) | 10 | 22 |
| (23) | 300 | 32 |
| (27) | 30 | 20 |
| (28) | 30 | 29 |

(ii) Coronary vasodilating effects:

Following compounds increased coronary blood flow by over 30% by i.v. administration.

| Compounds | Dose (μg/kg) | Increase (%) |
|---|---|---|
| (3) | 100 | 36 |
| (4) | 300 | 33 |
| (5) | 300 | 43 |
| (6) | 10 | 45 |
| (7) | 10 | 52 |
| (8) | 10 | 33 |
| (10) | 300 | 132 |
| (11) | 10 | 36 |
| (13) | 300 | 34 |
| (14) | 10 | 54 |
| (15) | 300 | 125 |
| (16) | 300 | 113 |
| (18) | 300 | 89 |
| (21) | 300 | 63 |
| (22) | 300 | 107 |
| (23) | 300 | 157 |
| (26) | 30 | 33 |
| (27) | 30 | 37 |
| (28) | 30 | 53 |
| (30) | 300 | 47 |

(iii) Cardiotonic effects:

Following compounds increased dp/dt max by over 20% by i.v. administration.

| Compounds | Dose (μg/kg) | Increase (%) |
|---|---|---|
| (3) | 100 | 20 |
| (5) | 300 | 20 |
| (10) | 300 | 39 |
| (13) | 300 | 39 |
| (15) | 300 | 83 |
| (18) | 300 | 20 |
| (22) | 300 | 24 |
| (23) | 300 | 44 |
| (30) | 300 | 46 |

III. $CA^{2+}$-AGONISTIC AND ANTAGONISTIC ACTIVITY IN RABBIT AORTA

1. Methods

Rabbit aorta were isolated and cut into ring segments of about 2 mm. These preparations were suspended in 40 ml chambers filled with Krebs-Henseleit solution bubbled with a gas mixture of 95% $O_2$+5% $CO_2$ (pH 7.4) and kept at 37° C. The contractile response to $[K^+]_o$ (9–48 mM) was measured in the absence or presence of test compounds (1).

(1) R. P. Hof et al. J. Cardiovasc. Pharmacol. 7, 689 (1985)

2. Results

Following compounds showed $[K^+]_o$-dependent conversion of $Ca^{2+}$-agonistic to $Ca^{2+}$-antagonistic action. That is, at lower $[K^+]_o$ these compounds augmented contractile force, however, at higher $[K^+]_o$ they produced only relaxation of aorta. $[K^+]_o$, at which conversion of the effects of compounds ($10^{-6}$M) occurred, was as follows.

| Compounds | $[K^+]_o$ (mM) |
|---|---|
| (1) | 23 |
| (3) | 24 |
| (10) | 21 |
| (11) | 22 |
| (13) | 24 |
| (15) | 20 |
| (23) | 19 |
| (27) | 22 |
| (30) | 28 |

IV. $CA^{2+}$-AGONISTIC AND ANTAGONISTIC ACTION IN RABBIT MYOCARDIUM

1. Methods

Papillary muscle was isolated from rabbit heart and suspended in 40 ml chamber filled with Krebs-Henseleit solution ($[Ca^{2+}]_o$ was elevated to 5 mM) bubbled with a gas mixture of 95% $O_2$+5% $CO_2$ and kept at 37° C. The preparation was electrically driven at a rate of 0.5 Hz and developed tension was observed. $[K^+]_o$ was varied from 5.9 mM to 27 mM in the absence and presence of test compounds.

2. Results

Following compounds showed $[K^+]_o$-dependent conversion of $Ca^{2+}$-agonistic to $Ca^{2+}$-antagonistic action. That is, at lower $[K^+]_o$ these compounds showed positive inotropic effect, however, at higher $[K^+]_o$ they produced only negative inotropic effect. $[K^+]_o$, at which conversion of the effects of compounds ($10^{-4}$M) occurred, was as follows.

| Compounds | $[K^+]_o$ (mM) |
|---|---|
| (1) | 16 |
| (10) | 15 |
| (13) | 14 |
| (15) | 18 |
| (23) | 12 |
| (25) | 15 |
| (27) | 12 |
| (30) | 15 |

V. EXPERIMENT OF ACUTE TOXICITY:

Compound (1), (10) and (23) were orally or intraperitoneally administered to ddY strain mice. All mice survived at the oral dose of 1,000 mg/kg and at the intraperitoneal dose of 250 mg/kg for five days after administration.

The present invention also provides isopropyl 5-(2-aminoethoxymethyl)-3-cyano-7-(2,3-difluorophenyl)-4,7-dihydropyrazolo[1,5-a]pyrimidine-6-carboxylate which exhibits mild and long-lasting hypotensive activity, high-selective coronary vasodilating activity, and higher bioavailability by the oral administration as well as potent diuretic activity and renal blood flow increasing activity and weak heart-depressive activity.

The compounds of the present invention, when used as drugs, can be administered in the form of powder, tablets, capsules, granules, injectable solutions, suppositories, ointments or the like by mixing with a suitable carrier, excipient, diluent or the like. The dose for human adults usually ranges from 10 mg to 500 mg, but it may vary depending upon the age, body weight, and severity of the conditions to be treated.

| | 25 mg tablets | 50 mg tablets |
|---|---|---|
| Formulation Example 1: Tablets | | |
| Compounds (I) | 25.0 mg | 50.0 mg |
| Lactose | 59.5 | 67.0 |
| Corn starch | 20.0 | 25.0 |
| Crystalline cellulose | 10.0 | 20.0 |
| Methyl cellulose | 1.0 | 1.5 |
| Talc | 4.0 | 6.0 |
| Magnesium stearate | 0.5 | 0.5 |
| | 120.0 mg | 170.0 mg |
| Formulation Example 2: 10% Powder | | |
| Compound (I) | 10.0% | |
| Lactose | 59.5 | |
| Corn starch | 30.0 | |
| Talc | 0.5 | |
| | 100.0% | |

The present invention will be explained by the following examples in more detail, but these examples are not to be construed as limiting the present invention:

EXAMPLE 1

To 1-phenyl-2-piperidinoethyl α-acetyl-3-nitrocinnamate prepared from 7.5 g of 3-nitrobenzaldehyde and 14.5 g of 1-phenyl-2-piperidinoethyl acetoacetate is added a solution of 4.2 g of 3-aminopyrazole in ethanol, and then stirred at 50° C. for 3 hours. The mixture is concentrated at reduced pressure, and the residue is purified by column chromatography on silica gel with chloroform-ethyl acetate-ethanol eluents to give two forms of diastereromers. The initally eluted solution is concentrated and the residue is recrystallized from ethanol to give one form (α-form) of diastereomer of 1-phenyl-2-piperidinoethyl 5-methyl-7-(3-nitrophenyl)-4,7-dihydropyrazolo[1,5-a]pyrimidine-6-carboxylate, melting at 92°-93° C. Then, the subsequently eluted solution is concentrated and the residue is recrystallized from ethanol to give the other form (β-form) of diastereomer of 1-phenyl-2-piperidinoethyl 5-methyl-7-(3-nitrophenyl)-4,7-dihydropyrazolo[1,5-a]pyrimidine-6-carboxylate, melting at 191°-192° C.

EXAMPLE 2

Ethyl α-acetyl-β-(3-aminopyrazol-2-ly)-β-(2-trifluoromethylphenyl)propionate (34.5 g) is dissolved in 200 ml of chloroform and heated under reflux for 6 hours. After the reaction mixture is washed with water, dried and concentrated, the residue is purified by column chromatography on silica gel with chloroform-methanol eluents to give 24 g of the product. The product is crystallized from isopropylether and further recrystallized from ethanol to give 6-ethoxycarbonyl-5-methyl-7-(2-trifluoromethylphenyl)-4,7-dihydropyrazolo[1,5-a]pyrimidine, melting at 182°-183° C.

Ethyl α-acetyl-β-(3-aminopyrazol-2-ly)-β-(2-trifluoromethylphenyl)propionate is synthesized by the following manner.

Ethyl α-acetyl-2-trifluoromethylcinnamate (36 g) and 10.5 g of 3-aminopyrazole are dissolved in 200 ml of ethanol, and the mixture is stirred at room temperature for 5 hours. The precipitated white crystals are collected by filtration to give 8.5 g of ethyl α-acetyl-β-(3-aminopyrazol-2-ly)-β-(2-trifluoromethylphenyl)propionate, melting at 136°-137° C.

EXAMPLE 3

To the crude 1-phenyl-2-piperidinoethyl α-acetyl-3-nitrocinnamate, which was synthesized by reacting 30 g of 3-nitrobenzaldehyde with 67 g of 1-phenyl-2-piperidinoethyl acetoacetate, is added 500 ml of ethanol solution of 2-aminoimidazole prepared from 26.4 g of 2-aminoimidazole sulfate and sodium hydroxide, and then stirred at 50° C. for 5 hours. After cooling, the precipitated crystals are collected by filtration and recrystallized from ethanol to give 9.7 g of 1-phenyl-2-piperidinoethyl 7-methyl-5-(3-nitrophenyl)-5,8-dihydroimidazo[1,2-a]pyrimidine-6-carboxylate, melting at 205°-206° C. as one diastereomer (α-form). Then, the filtrate is concentrated under reduced pressure, and the residue is purified by column chromatography on silica gel with chloroform-ethyl acetate-ethanol eluents. The crystals thus obtained are recrystallized from a mixture of chloroform and ethanol to give 4.8 g of 1-phenyl-2-piperidinoethyl 7-methyl-5-(3-nitrophenyl)-5,8-dihydroimidazo[1,2-a]pyrimidine-6-carboxylate, melting at 216°-217° C. with decomposition as the other diastereomer (β-form).

EXAMPLE 4

To a solution of 10.5 g of 2-aminoimidazole sulfate in 11 ml of water is added a sodium ethoxide solution prepared from 1.7 g of metal sodium and 200 ml of ethanol. After the precipitated crystals are filtered off, to the filtrate is added 15.5 g of ethyl α-acetylcrotonate and then stirred at 50° C. for 3 hours and at 75° C. for 3 hours. After the ethanol is evaporated at reduced pressure, the residue is extracted by chloroform, washed with water and dried. The solvent is distilled off under reduced pressur to give white crystals. The crystals are recrystallized from ethanol to give 10.2 g of 6-ethoxycarbonyl-5,7-dimethyl-5,8-dihydroimidazo[1,2-a]pyrimidine, melting at 185°-186.5° C.

EXAMPLE 5

To 50 ml of ethanol are added 2.6 g of ethyl 3-nitro-α-acetylcinnamate and 0.9 g of 5-aminotetrazole, and then heated under reflux for 16 hours. On cooling, 2 g of 6-ethoxycarbonyl-5-methyl-7-(3-nitrophenyl)-4,7-dihydrotetrazolo[1,5-a]pyrimidine, melting at 210°-212° C., is obtained.

EXAMPLE 6

To 50 ml of ethanol are added 7.8 g of ethyl α-acetylcrotonate and 4.2 g of 3-amino-1,2,4-triazole, stirred at 50° C. for an hour and then heated under reflux for an hour. The ethanol is evaporated under reduced pressure, and the obtained crystals are recrystallized from ethanol to give 7 g of 6-ethoxycarbonyl-5,7-dimethyl-4,7-dihydro-1,2,4-triazolo[1,5-a]pyrimidine, melting at 155°-157° C.

EXAMPLE 7

A solution of 6.7 g of 6-ethoxycarbonyl-5,7-dimethyl-4,7-dihydro-1,2,4-triazolo[1,5-a]pyrimidine in 40 ml of acetic acid is heated at 50° C. To the reaction mixture is added dropwise a solution of 4.8 g of bromine in 20 ml of acetic acid for 10 minutes, and then the mixture is stirred at 50°-60° C. for an hour. The resulting mixture is poured into water, extracted with chloroform, washed with water and dried. The chloroform layer is purified by column chromatography on silica gel to give 0.5 g of 5-dibromomethyl-6-ethoxycarbonyl-7-methyl-4,7-dihydro-1,2,4-triazolo[1,5-a]pyrimidine, melting at 170°-171° C. with decomposition.

EXAMPLE 8

A mixture of 50 g of methyl 2-acetyl-3-(2-thienyl)acrylate, 20 g of 3-amino-1,2,4-triazole and 300 ml of ethanol is heated under reflux for 4 hours. The precipitated white crystals are collected by filtration to give 29.5 g of 6-methoxycarbonyl-5-methyl-7-(2-thienyl)-4,7-dihydro-1,2,4-triazolo[1,5-a]pyrimidine, melting at 239°-240° C.

Methyl 2-acetyl-3-(2-thienyl)acrylate was synthesized by the following manner.

A mixture of 112 g of 2-thiophenecarbaldehyde, 116 g of methyl acetoacetate, 770 ml of benzene, 4 ml of acetic acid and 3 ml of piperidine is heated under reflux for 2.5 hours under the condition of azeotropic dehydration. The benzene is evaporated under reduced pressure and the residual solvent is distilled off to give 199 g of methyl 2-acetyl-3-(2-thienyl)acrylate, boiling at 130°-160° C./0.2 mmHg.

EXAMPLE 9

In 300 ml of acetic acid is dissolved 29.5 g of 6-methoxycarbonyl-5-methyl-7-(2-thienyl)-4,7-dihydro-1,2,4-triazolo[1,5-a]pyrimidine at 60° C. To the solution is added dropwise a solution of 16 g of bromine in 50 ml of acetic acid for 20 minutes with stirring. After stirring at room temperature for an hour, the reaction mixture is poured into water, extracted with chloroform, washed with water and potassium carbonate solution, dried and the solvent is evaporated under reduced pressure. The obtained pale yellow crystals are recrystallized from ethanol to give 18 g of 5-bromomethyl-6-methoxycarbonyl-7-(2-thienyl)-4,7-dihydro-1,2,4-triazolo[1,5-a]pyrimidine, melting at 155° C. with decomposition.

EXAMPLE 10

A mixture of 29.2 g of benzalacetone and 17.6 g of 3-amino-1,2,4-triazole is refluxed in 150 ml of dimethylformamide for 3 hours. On cooling at room temperature, crystals are precipitated and collected by filtration. The crystals are recrystallized from dimethylformamide to give 17 g of 5-methyl-7-phenyl-4,7-dihydro-1,2,4-triazole[1,5-a]pyrimidine, melting at 220°-222° C.

EXAMPLE 11

To a solution of 41.3 g of 2-aminoimidazole sulfate in 50 ml of water are added 6.8 g of sodium hydroxide and 500 ml of methanol, and the mixture is stirred and dried over sodium sulfate. To the resulting solution is added 77.9 g of methyl α-acetyl-3-nitrocinnamate, stirred at 50° C. for 2.5 hours and refluxed under heating for 1.5 hours. On cooling at room temperature, crystals are precipitated and collected by filtration to give 81.4 g of 6-methoxycarbonyl-7-methyl-5-(3-nitrophenyl)-5,8-dihydroimidazo[1,2-a]pyrimidine, melting at 263°-264° C. with decomposition.

EXAMPLE 12

A mixture of 20.0 g of 6-methoxycarbonyl-7-methyl-5-(3-nitrophenyl)-5,8-dihydroimidazo[1,2-a]pyrimidine, 200 ml of acetic acid and 3.0 g of 10 palladium-carbon is stirred at room temperature for 5 hours under hydrogen gas. After an insoluble material is filtered off, the filtrate is neutralized with sodium bicarbonate, and extracted with chloroform. The extract is dried and the solvent is distilled off under reduced pressure. The precipitated pale yellow crystals are collected by filtration and recrystallized from methanol to give 11.0 g of 5-(3-aminophenyl)-6-methoxycarbonyl-7-methyl-5,8-dihydroimidazo[1,2-a]pyrimidine, melting at 224°-225° C.

EXAMPLE 13

To a solution of 4.0 g of 2-aminoimidazole sulfate in 10 ml of water are added 1.2 g of sodium hydroxide and 200 ml of methanol, and the mixture is dried over sodium sulfate. To the resulting solution is added 9.5 g of 2-methoxyethyl α-acetyl-2-trifluoromethylcinnamate and stirred at 50° C. for 3 hours. After stirring under reflux for 3.5 hours, the solvent is distilled off and the precipitated crystals are collected by filtration. The crystals are recrystallized from a mixture of methanol and chloroform to give 5.5 g of 6-(2-methoxyethoxycarbonyl)-7-methyl-5-(2-trifluoromethylphenyl)-5,8-dihydroimidazo[1,2-a]pyrimidine, melting at 181°-182° C.

2-Methoxyethyl α-acetyl-2-trifluoromethylcinnamate is synthesized by the following manner.

A mixture of 12.2 g of 2-trifluoromethylbenzaldehyde, 11.2 g of 2-methoxyethyl acetoacetate, 1 ml of piperidine, 2 ml of acetic acid and 150 ml of benzene is refluxed under the condition of azeotropic dehydration for 3.5 hours. The solvent is distilled off under reduced pressure to give red brown oil. The oil is distilled under reduced pressure to give 15.5 g of 2-methoxyethyl α-acetyl-2-trifluoromethylcinnamate, boiling at 145°-151° C./0.5 mmHg.

EXAMPLE 14

Crystals are obtained by reacting 6.8 of 2-aminoimidazole sulfate with 10.5 g of methyl 2-acetyl-3-cyclohexylacrylate in a similar manner as described in Example 13. Recrystallization from methanol gives 4.8 g of 5-cyclohexyl-6-methoxycarbonyl-7-methyl-5,8-dihydroimidazo[1,2-a]pyrimidine, melting at 178° C.

EXAMPLE 15

To 100 ml of benzene are added 10.7 g of 2-pyridinecarbaldehyde and 13 g of methyl acetoacetate, and maintained at 30°-40° C. for 2 hours in the presence of 0.5 ml of acetic acid and 0.25 ml of piperidine. The mixture is washed with sodium chloride solution, dried and the solvent is distilled off. To the residue is added 150 ml of isopropanol solution containing 2-aminoimidazole prepared from 10.5 g of 2-aminoimidazole sulfate and 2.9 g of sodium hydroxide, and then refluxed under heating for 2 hours. The reaction mixture is passed through silica gel column, and the solvent of the eluate is distilled off. Crystallization from methanol gives 2.5 g of 6-methoxycarbonyl-7-methyl-5-(2-pyridyl)-5,8-dihydroimidazo[1,2-a]pyrimidine, melting at 224°-226° C. with decomposition.

EXAMPLE 16

2-N,N-diethylaminoethyl 5-(3-nitrophenyl)-7-methyl-5,8-dihydroimidazo[1,2-a]pyrimidine-6-carboxylate (1.6 g), melting at 119°-121° C. is obtained as crystals by reacting 7.6 g of 3-nitrobenzaldehyde with 10.1 g of 2-N,N-diethylaminoethyl acetoacetate and 4.5 g of 2-aminoimidazole sulfate in a similar manner as described in Example 15.

EXAMPLE 17

In a mixture of 50 ml of acetone, 30 ml of methanol and 20 ml of water is dissolved 1.8 g of 5-[3-(2-methyl-1,3-dioxolan-2-yl)phenyl]-6-methoxycarbonyl-7-methyl-5,8-dihydroimidazo[1,2-a]pyrimidine. The mixture is adjusted to pH 1 with p-toluenesulfonic acid and then heated at 60° C. for 3 hours. The solvent is distilled off and the residue is neutralized with sodium bicarbonate solution. The resulting white precipitations are collected by filtration and recrystallized from a mixture of ethanol and acetone to give 1.1 g of 5-(3-acetylphenyl)-6-methoxycarbonyl-7-methyl-5,8-dihydroimidazo[1,2-a]pyrimidine, melting at 227°-229° C.

5-[3-(2-methyl-1,3-dioxolan-2-yl)phenyl]-6-methoxycarbonyl-7-methyl-5,8-dihydroimidazo[1,2-a]pyrimidine is synthesized according to the following manner.

5-[3-(2-methyl-1,3-dioxolan-2-yl)phenyl]-6-methoxycarbonyl-7-methyl-5,8-dihydroimidazo[1,2-a]pyrimidine (9 g), melting at 199°-201° C., is obtained by reacting 11 g of 3-(2-methyl-1,3-dioxolan-2-yl)benzaldehyde with 7.3 g of methyl acetoacetate and 9 g of 2-aminoimidazole sulfate in a similar manner as described in Example 15.

EXAMPLE 18

To an isopropanol solution of 2-aminoimidazole, which is prepared from 7.9 g of 2-aminoimidazole sulfate and 2.2 g sodium hydroxide, is added 11.7 g of α-acetyl-3-nitrocrotonamide and heated under reflux for 5 hours. After cooling, the precipitated crystals are collected by filtration to give 12 g of 6-carbamoyl-7-methyl-5-(3-nitrophenyl)-5,8-dihydroimidazo[1,2-a]pyrimidine, melting at 238°-240° C.

α-Acetyl-3-nitrocrotonamide is synthesized by the following manner.

A mixture of 10 g of acetoacetamide and 15 g of 3-nitrobenzaldehyde in 100 ml of isopropanol is stirred at 35° C. for 4 hours in the presence of 0.3 ml of piperidine and 0.5 ml of acetic acid. The precipitated yellow crystals are collected by filtration to give 20 g of α-acetyl-3-nitrocrotonamide, melting at 159°-161° C.

EXAMPLE 19

1.5 ml of thionyl chloride is added dropwise to a solution of 3 g of 6-carbamoyl-7-methyl-5-(3-nitrophenyl)-5,8-dihydroimidazo[1,2-a]pyrimidine in 30 ml of dimethylformamide. After stirring for an hour, the mixture is poured into chloroform and washed with sodium bicarbonate solution followed by passing the mixture through a column containing 50 g of silica gel with a mixture of dichloromethane and ethanol as an eluent. Upon allowing the eluates to stand, crystals are precipitated and collected by filtration to give 1.1 g of 6-cyano-7-methyl-5-(3-nitrophenyl)-5,8-dihydroimidazo[1,2-a]pyrimidine, melting at 278°-280° C. with decomposition.

EXAMPLE 20

50 ml of ethanol is added to a solution of 4.5 g of 2-aminoimidazole sulfate and 1.3 g of sodium hydroxide in 11 ml of water and dried over sodium sulfate. To the solution is added 10 g of ethyl 4,4-dimethoxy-2-(3-nitrobenzylidene)-3-oxobutylate. The resulting mixture is stirred at 50° C. for 30 minutes and further refluxed under heating for 6 hours. After cooling, the precipitated yellow crystals are collected by filtration, purified by column chromatography on silica gel with chloroform-methanol eluents, and then recrystallized from methanol to give 6 g of 7-dimethoxymethyl-6-ethoxycarbonyl-5-(3-nitrophenyl)-5,8-dihydroimidazo[1,2-a]pyrimidine, melting at 190°-191° C. with decomposition.

Ethyl 4,4-dimethoxy-2-(3-nitrobenzylidene)-3-oxobutylate is synthesized by the following manner.

A solution of 24 g of 3-nitrobenzaldehyde, 30 g of ethyl 4,4-dimethoxy-3-oxobutylate, 0.5 ml of piperidine and 1 ml of acetic acid in 200 ml of benzene is refluxed under heating for 4 hours under the condition of azeotropic dehydration. The solvent is distilled off and evaporated under reduced pressure to give 36 g of ethyl 4,4-dimethoxy-2-(3-nitrobenzylidene)-3-oxobutylate, boiling at 195°-210° C./0.2 mmHg.

EXAMPLE 21

10 ml of 6N hydrochloric acid is added to a solution of 4.4 g of 7-dimethoxymethyl-6-ethoxycarbonyl-5-(3-nitrophenyl)-5,8-dihydroimidazo[1,2-a]pyrimidine in mixture of 10 ml of acetone and 10 ml of water and the mixture is stirred at room temperature for an hour, and then allowed to stand overnight. The solvent is distilled off under reduced pressure below 40° C. to give 4 g of 6-ethoxycarbonyl-7-formyl-5-(3-nitrophenyl)-5,8-dihydroimidazo[1,2-a]pyrimidine hydrochloride, melting at 228° C. with decomposition.

EXAMPLE 22

To a solution of 6-ethoxycarbonyl-7-formyl-5-(3-nitrophenyl)-5,8-dihydroimidazo[1,2-a]pyrimidine hydrochloride in a mixture of 20 ml of ethanol and 20 ml of dimethylformamide are added 0.88 g of hydroxylamine hydrochloride and 1.22 g of sodium carbonate and the mixture is stirred at 50° C. for 1.5 hours. The solvent is distilled off under reduced pressure and water is added to the residue, then precipitated crystals are collected by filtration. The crystals are recrystallized from a mixture of chloroform and methanol to give 2.0 g of 6-ethoxycarbonyl-7-hydroxyiminomethyl-5-(3-nitrophenyl)-5,8-dihydroimidazo[1,2-a]pyrimidine, melting at 229°-230° C. with decomposition.

EXAMPLE 23

A solution of 6-ethoxycarbonyl-7-hydroxyiminomethyl-5-(3-nitrophenyl)-5,8-dihydroimidazo[1,2-a]pyrimidine (1.25 g), 0.29 g of sodium acetate and 0.4 ml of acetic anhydride in 15 ml of acetic acid is stirred with heating at 80°-90° C. for 30 minutes. The reaction solution is poured into water and precipitated crystals are collected by filtration. Recrystallization from a mixture of chloroform and ethanol gives 0.5 g of 7-cyano-6-ethoxycarbonyl-5-(3-nitrophenyl)-5,8-dihydroimidazo[1,2-a]pyrimidine, melting at 260°-261° C. with decomposition.

EXAMPLE 24

12 g of 8-carboxy-3-ethoxycarbonyl-2-methyl-4-(3-nitrophenyl)-1,4-dihydroimidazo[1,5-a]pyrimidine is heated at 215° C. for 20 minutes and purified by column chromatography on silica gel with chloroform eluent. The yellow crystals obtained are recrystallized from ethanol to give 1.5 g of 3-ethoxycarbonyl-2-methyl-4-(3-nitrophenyl)-1,4-dihydroimidazo[1,5-a]pyrimidine, melting at 196°-197° C.

8-Carboxy-3-ethoxycarbonyl-2-methyl-4-(3-nitrophenyl)-1,4-dihydroimidazo[1,5-a]pyrimidine is synthesized by the following manner.

0.17 g of potassium hydroxide in 1.7 ml of water is added to a solution of 1.0 g of 3,8-diethoxycarbonyl-2-methyl-4-(3-nitrophenyl)-1,4-dihydroimidazo[1,5-a]pyrimidine in 20 ml of ethanol, and gradually heated followed by stirring at 70° C. for 10 hours. The ethanol is distilled off under reduced pressure, chloroform is added to the resulting oil and extracted with potassium carbonate solution. The water layer is washed with chloroform and adjusted to pH 5-6 with acetic acid. The precipitated crystals are collected by filtration and recrystallized from ethanol to give 0.32 g of 8-carboxy-3-ethoxycarbonyl-2-methyl-4-(3-nitrophenyl)-1,4-dihydroimidazo[1,5-a]pyrimidine, melting at 222° C. with decomposition.

3,8-Diethoxycarbonyl-2-methyl-4-(3-nitrophenyl)-1,4-dihydroimidazo[1,5-a]pyrimidine is synthesized by the following manner.

A solution of 2 g. of 5-amino-4-ethoxycarbonylimidazole and 3.4 g of ethyl α-acetyl-3-nitrocinnamate in 50 ml of ethanol is refluxed under heating for 7 hours under a nitrogen atmosphere. The ethanol is removed under reduced pressure, the resulting oil is purified by column chromatography on silica gel with a mixture of chloroform and methanol as eluent. Recrystallization from a mixture of isopropyl alcohol and isopropyl ether gives 2.5 g of 3,8-diethoxycarbonyl-2-methyl-4-(3-nitrophenyl)-1,4-dihydroimidazo[1,5-a]pyrimidine, melting at 160°-162° C.

EXAMPLE 25

16 mg of sodium borohydride is added gradually to a solution of 17 mg of 6-methoxycarbonyl-5-methyl-7-(2-trifluoromethylphenyl)pyrazolo[1,5-a]pyrimidine in 1 ml of methanol with stirring and heating at 60° C. The reaction mixture is poured into water, extracted with ethyl acetate and dried. The solvent is removed and the residue is recrystallized from methanol to give 6-methoxycarbonyl-5-methyl-7-(2-trifluoromethylphenyl)-4,7-dihydropyrazolo[1,5-a]pyrimidine, melting at 209°-210° C.

The compounds summarized in the following tables can also be, for example, prepared in a similar manner as the above examples.

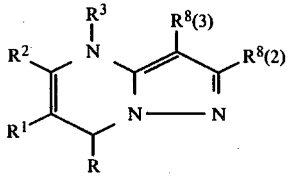
| No. | R | $R^1$ | $R^2$ | $R^3$ | $R^8(2)$ | $R^8(3)$ | M.p. (°C.) |
|---|---|---|---|---|---|---|---|
| 26 | 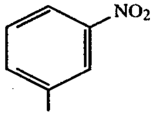 | $C_2H_5OOC$ | $CH_3$ | H | H | H | 157–159(d) |
| 27 | $CH_3$ | $C_2H_5OOC$ | $CH_3$ | H | H | H | 168–170 |
| 28 | 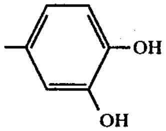 | $CH_3OOC$ | $CH_3$ | H | H | H | 253–255 |
| 29 | 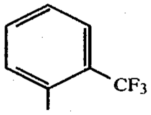 | $C_2H_5OOC$ | $CH_2OCOCH_3$ | H | H | H | 166–167 |
| 30 | 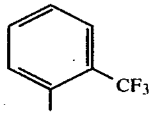 | $C_2H_5OOC$ | $CH_2OH$ | H | H | H | 229–230 |
| 31 | 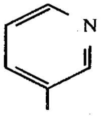 | $CH_3OOC$ | $CH_3$ | H | H | H | 222–223 |

-continued
| | | | | | | | |
|---|---|---|---|---|---|---|---|
| 32 | 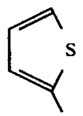 | $C_2H_5OOC$ | $C_3H_7$ | H | H | H | 169–170 |
| 33 | 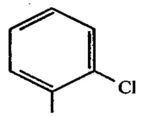 | $C_2H_5OOC$ | $CH_3$ | H | H | H | 176–178 |
| 34 | 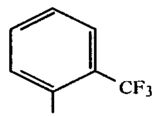 | $C_4H_9OOC$ | $CH_3$ | H | H | H | 134–136 |
| 35 | 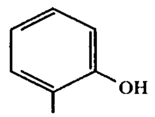 | $CH_3OOC$ | $CH_3$ | H | H | H | 218–220 |
| 36 | 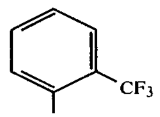 | $C_2H_5OOC$ | $CH_2Cl$ | H | H | H | 147–149 |
| 37 | 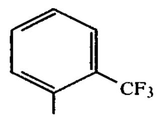 | $C_2H_5OOC$ | $CH_2F$ | H | H | H | 118–119 |
| 38 | 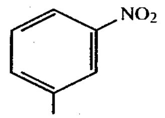 | $CH_3CO$ | $CH_3$ | H | H | H | 190–192 |

-continued
| | | | | | | | |
|---|---|---|---|---|---|---|---|
| 39 | 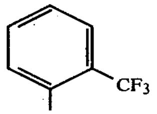 | 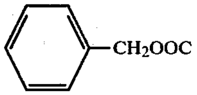 | $CH_3$ | H | H | H | 164–166 |
| 40 | 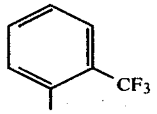 | HOOC | $CH_3$ | H | H | H | 172–173(d) |
| 41 | 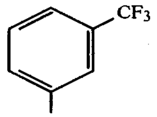 | $C_2H_5OOC$ | $CH_3$ | H | H | H | 189–190 |
| 42 | 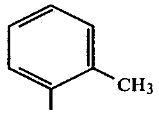 | $C_2H_5OOC$ | $CH_3$ | H | H | H | 186–187 |
| 43 | 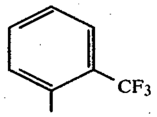 | $C_3H_7OOC$ | $CH_3$ | H | H | H | 168–169 |
| 44 | 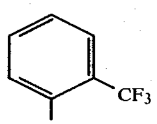 | $(CH_3)_2CHOOC$ | $CH_3$ | H | H | H | 160–162 |
| 45 | 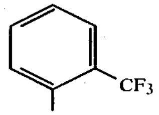 | $(CH_3)_2CHCH_2OOC$ | $CH_3$ | H | H | H | 144–145 |

-continued
| | | | | | | | |
|---|---|---|---|---|---|---|---|
| 46 | 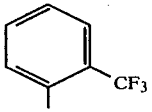 | $(CH_3)_3COOC$ | $CH_3$ | H | H | H | 168-170 |
| 47 | 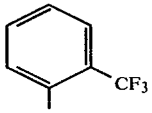 | 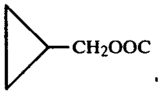 | $CH_3$ | H | H | H | 182-183 |
| 48 | 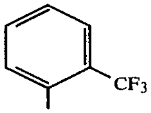 | 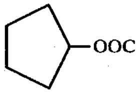 | $CH_3$ | H | H | H | 159-160 |
| 49 | 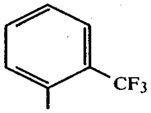 | $CH_3OCH_2CHOOC$ 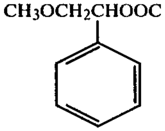 | $CH_3$ | H | H | H | α: 176-178<br>β: 202-204 |
| 50 | 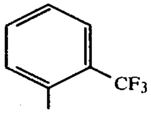 | $C_2H_5OOC$ | $CH_3$ | H | H | Cl | 199-200 |
| 51 | 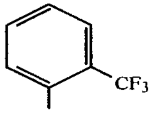 | 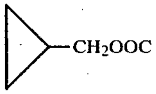 | $CH_3$ | H | H | CN | 223-225 |
| 52 | 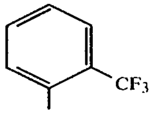 | $C_2H_5OOC$ | $CH_3$ | H | 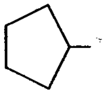 | H | 194-195 |

-continued
| | | | | | | | |
|---|---|---|---|---|---|---|---|
| 53 | 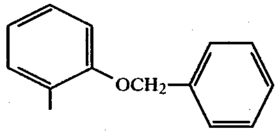 | $C_2H_5OOC$ | $CH_3$ | H | H | H | 182-184 |
| 54 | 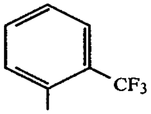 | $O_2N$ | $CH_3$ | H | H | H | 239-240 |
| 55 | 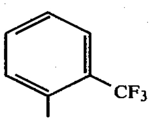 | 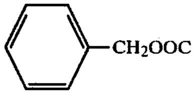 | $CH_3$ | $CH_2OC_2H_5$ | H | H | 79-80 |
| 56 | 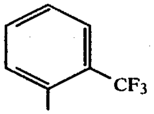 | HOOC | $CH_3$ | $CH_2OC_2H_5$ | H | H | 155-157(d) |
| 57 | 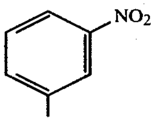 | $C_2H_5OOC$ | $(C_2H_5)_2NCH_2$ | H | H | H | 138-140 |
| 58 | 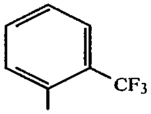 | $C_2H_5OOC$ | $CH_3$ | H | H | $CH_2N(C_2H_5)_2$ | 190-192(d) |
| 59 | 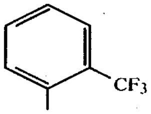 | 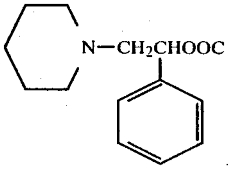 | $CH_3$ | H | H | H | α: 151-153<br>β:99-101* |

-continued
| | | | | | | | |
|---|---|---|---|---|---|---|---|
| 60 | 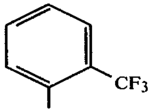 | $C_2H_5OOC$ | $CH_3$ | H | H | H | α: 139-141<br>β: 140-141** |
*diastereomer, $[\alpha]_D = +90.7°$ (C = 1.06 $C_2H_5OH$), $[\alpha]_D = +79.1°$ (C = 1.06 $C_2H_5OH$)
**enantiomer, $[\alpha]_D = -91.9°$ (C = 1.07 $C_2H_5OH$), $[\alpha]_D = +97.7°$ (C = 0.97 $C_2H_5OH$)
| | | | | | | | |
|---|---|---|---|---|---|---|---|
| 61 | 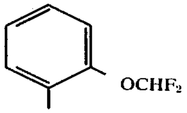 | $C_2H_5OOC$ | $CH_3$ | H | H | H | 191-192 |
| 62 | 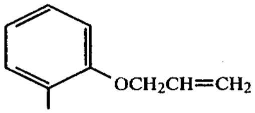 | $C_2H_5OOC$ | $CH_3$ | H | H | H | 203-204 |
| 63 | 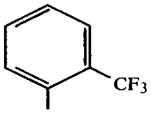 | $CH_3OOC$ | $CH_3$ | H | H | $COOC_2H_5$ | 118-120 |
| 64 | 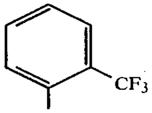 | $CH_3OOC$ | $CH_3$ | H | H | Br | 186-187 |
| 65 | 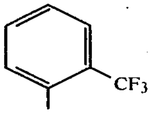 | $CH_3OOC$ | $CH_3$ | H | H | $NO_2$ | 247-249 |
| 66 | 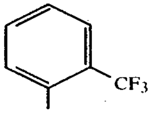 | $CH_3OOC$ | $CH_3$ | H | H | CN | 268-270 |

-continued
| | | | | | | | |
|---|---|---|---|---|---|---|---|
| 67 | 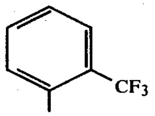 | $CH_3OOC$ | $CH_3$ | H | H | $CONH_2$ | 278–280 |
| 68 | 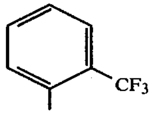 | $FCH_2CH_2OOC$ | $CH_3$ | H | H | H | 185–187 |
| 69 | 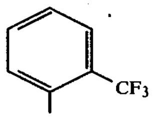 | $CH_3OOC$ | $CH_3$ | H | H | COOH | 216–217 |
| 70 | 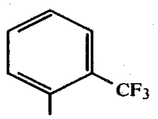 | $CH_3OCH_2CH_2OOC$ | $CH_3$ | H | H | H | 142–143 |
| 71 | 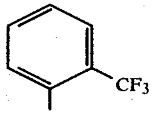 | $O_2N$ | $CH_3$ | H | H | $COOC_2H_5$ | 188–190 |
| 72 | 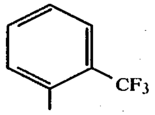 | $ClCH_2CH_2OOC$ | $CH_3$ | H | H | H | 189–190 |
| 73 | 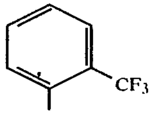 | $C_2H_5OOC$ | $CH_3$ | H | H | 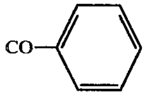 | 119–121 |

-continued
| | | | | | | | |
|---|---|---|---|---|---|---|---|
| 74 | 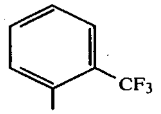 | $CF_3CH_2OOC$ | $CH_3$ | H | H | H | 191–193 |
| 75 | 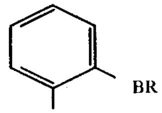 | $C_4H_9OOC$ | $CH_3$ | H | H | H | 155–156 |
| 76 | 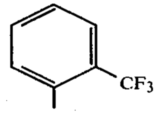 | $C_2H_5OOC$ | $CH_3$ | H | CN | H | |
| 77 | 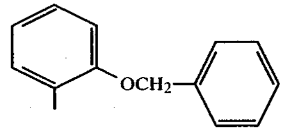 | 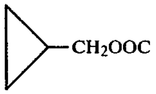 | $CH_3$ | H | H | H | 176–178 |
| 78 | 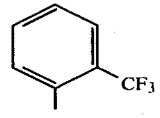 | 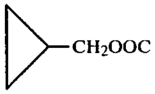 | $CH_3$ | H | H | $NO_2$ | 214–215 |
| 79 | 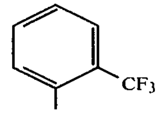 | 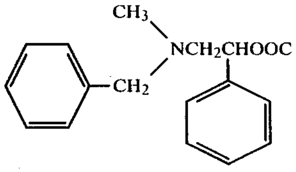 | $CH_3$ | H | H | H | α: 171–172<br>β: 169–170 |
| 80 | 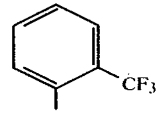 | $C_2H_5OOC$ | $CH_3$ | H | H | Br | 187–188 |

-continued
| | | | | | | | |
|---|---|---|---|---|---|---|---|
| 81 | 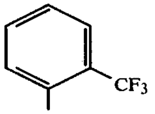 | $CH_3(CH_2)_7OOC$ | $CH_3$ | H | H | H | 104-105 |
| 82 | 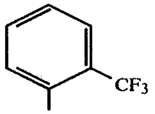 | $CH_3(CH_2)_5OOC$ | $CH_3$ | H | H | H | 105-107 |
| 83 | 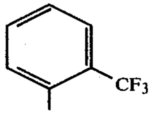 | $C_2H_5OOC$ | $CH_3$ | H | H | $COOC_2H_5$ | 116-118 |
| 84 | 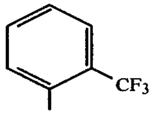 | $CH_2{=}CHCH_2OOC$ | $CH_3$ | H | H | H | 159-160 |
| 85 | 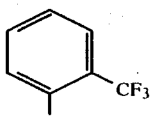 | 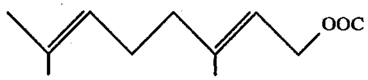 | $CH_3$ | H | H | H | 108-109 |
| 86 | 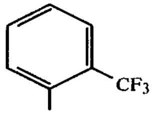 | $CH{\equiv}CCH_2OOC$ | $CH_3$ | H | H | H | 169-171 |
| 87 | 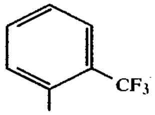 | $CH_3S(CH_2)_2OOC$ | $CH_3$ | H | H | H | 173-175 |

-continued
| | | | | | | | |
|---|---|---|---|---|---|---|---|
| 88 | 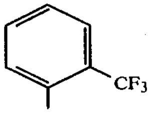 | $CH_3(CH_2)_4OOC$ | $CH_3$ | H | H | H | ½ $H_2O$ 115–117 |
| 89 | 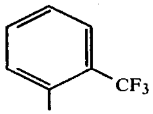 | 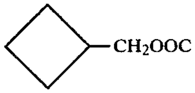 | $CH_3$ | H | H | H | 170–171 |
| 90 | 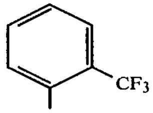 | $C_2H_5OOC$ | $CH_3$ | H | H | CN | 252–254 |
| 91 | 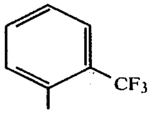 | 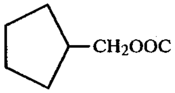 | $CH_3$ | H | H | H | 158–159 |
| 92 | 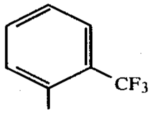 | 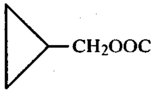 | $CH_3$ | H | H | $NH_2$ | 169–171 |
| 93 | 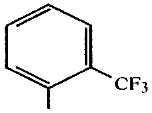 | 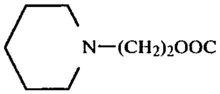 | $CH_3$ | H | H | H | ¼ $H_2O$ 81–82 |
| 94 | 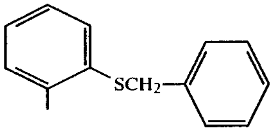 | $C_2H_5OOC$ | $CH_3$ | H | H | H | 146–147 |

-continued
| | | | | | | | |
|---|---|---|---|---|---|---|---|
| 95 | 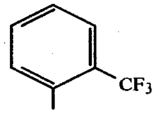 | 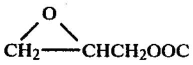 | $CH_3$ | H | H | H | 186-187 |
| 96 | 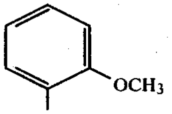 | $C_2H_5OOC$ | $CH_3$ | H | H | H | 178-179 |
| 97 | 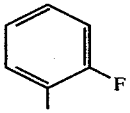 | $C_2H_5OOC$ | $CH_3$ | H | H | H | 188-191 |
| 98 | 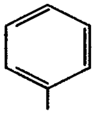 | $CH_3OOC$ | $CH_3$ | H | H | H | 198-200 |
| 99 | 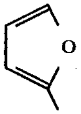 | $C_2H_5OOC$ | $C_3H_7$ | H | H | H | 153-155 |
| 100 | 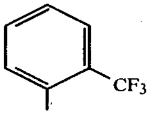 | $CH_3(CH_2)_{21}OOC$ | $CH_3$ | H | H | H | 107-110 |
| 101 | 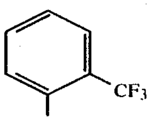 | 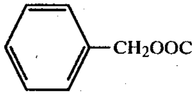 | $CH_3$ | H | H | H | 178-180 |

-continued
| | | | | | | | |
|---|---|---|---|---|---|---|---|
| 102 | 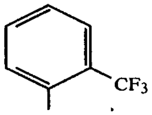 | $(CH_3)_3CCH_2OOC$ | $CH_3$ | H | H | H | 180-181 |
| 103 | 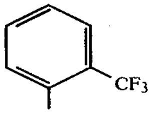 | 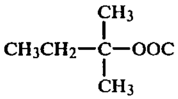 | $CH_3$ | H | H | H | 159-161 |
| 104 | 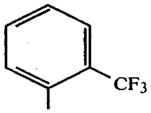 | 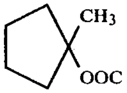 | $CH_3$ | H | H | H | 145-147 |
| 105 | 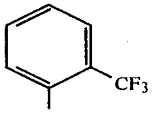 | $C_2H_5OOC$ | $C_3H_7$ | H | H | H | 151-152 |
| 106 | 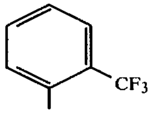 | $C_2H_5OOC$ | $CH_3$ | H | H | $NO_2$ | 195-198 |
| 107 | 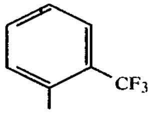 | $C_2H_5OOC$ | $CH_3$ | H | H | $CONH_2$ | 290-292 |
| 108 | 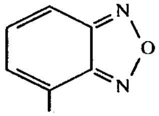 | $C_2H_5OOC$ | $CH_3$ | H | H | H | 204-205 |

-continued
| | | | | | | | |
|---|---|---|---|---|---|---|---|
| 109 | 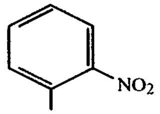 | $C_2H_5OOC$ | $CH_3$ | H | H | H | 157–160 |
| 110 | 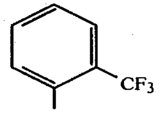 | 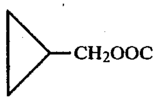 | $CH_3$ | H | H | $NHCOCH_3$ | |
| 111 | 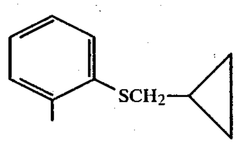 | $C_2H_5OOC$ | $CH_3$ | H | H | H | 173–175 |
| 112 | 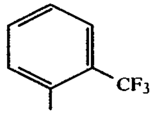 | 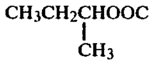 | $CH_3$ | H | H | H | |
| 113 | 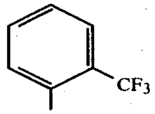 | 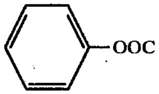 | $CH_3$ | H | H | H | 157–158 |
| 114 | 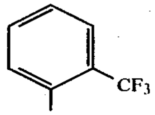 | 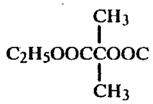 | $CH_3$ | H | H | H | 155–157.5 |
| 115 | 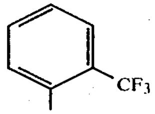 | CN | $CH_3$ | H | H | H | 240–241 |

-continued
| | | | | | | | |
|---|---|---|---|---|---|---|---|
| 116 | 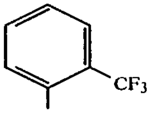 | $C_2H_5OOC$ | $CF_3$ | H | H | H | |
| 117 | 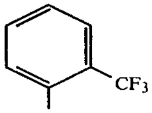 | $CH_3(CH_2)_{15}OOC$ | $CH_3$ | H | H | H | 91-93 |
| 118 | 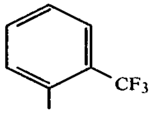 | 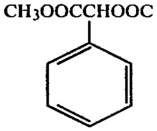 | $CH_3$ | H | H | H | α: 187-189<br>β: |
| 119 | 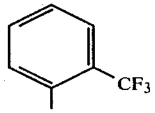 | 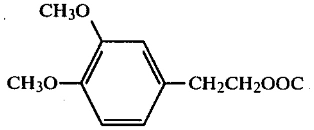 | $CH_3$ | H | H | H | 182-183.5 |
| 120 | 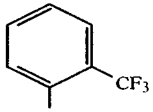 | 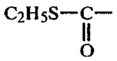 | $CH_3$ | H | H | H | |
| 121 | 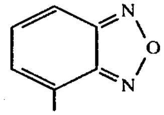 | $O_2N$ | $CH_3$ | H | H | H | |
| 122 | 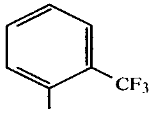 | $C_2H_5OOC$ | Cl | H | H | H | |

-continued
| | | | | | | | |
|---|---|---|---|---|---|---|---|
| 123 | 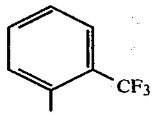 | $C_2H_5OOC$ | $(C_2H_5)_2NCH_2$ | H | H | H | |
| 124 | 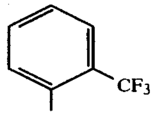 | $C_2H_5OOC$ | $CH_3NHCOOCH_2$ | H | H | H | |
| 125 | 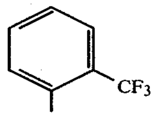 | $C_2H_5OOC$ | $CH_3$ | H | H | F | |
| 126 | 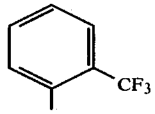 | $C_2H_5OOC$ | $CH_3$ | H | H | $CH_2OH$ | |
| 127 | 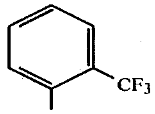 | $C_2H_5OOC$ | $CH_3$ | H | H | $C_3H_7$ | 131-133 |
| 128 | 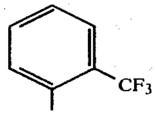 | $C_2H_5OOC$ | $(C_2H_5)_2N$ | H | H | H | |
| 129 | 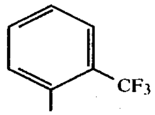 | $C_2H_5OOC$ | $(CH_3)_3C$ | H | H | H | |

-continued
| | | | | | | | |
|---|---|---|---|---|---|---|---|
| 130 | 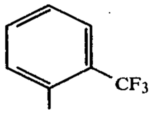 | $C_2H_5OOC$ | $CH_3NHCSOCH_2$ | H | H | H | |
| 131 | 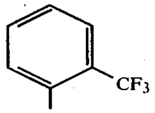 | $C_2H_5OOC$ | $CH_3$ | H | H | $CH_3$ | 203–204 |
| 132 | 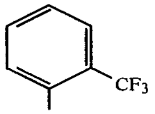 | $C_2H_5OOC$ | $CH_3$ | H | H | COOH | |
| 133 | 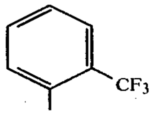 | $C_2H_5OOC$ | $CH_3$ | H | H | $NHCOCH_3$ | |
| 134 | 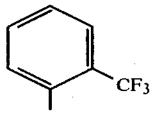 | $C_2H_5OOC$ | $CH_3$ | H | F | H | |
| 135 | 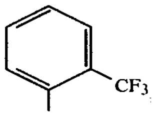 | $C_2H_5OOC$ | $CH_3$ | $CH_3$ | H | H | |
| 136 | 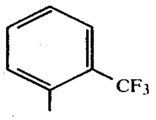 | $C_2H_5OOC$ | $CH_3$ | 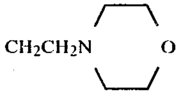 | H | H | |

-continued
| | | | | | | | |
|---|---|---|---|---|---|---|---|
| 137 | 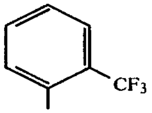 | 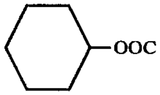 | $CH_3$ | H | H | 186–187 | |
| 138 | 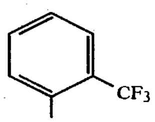 | $C_2H_5OOC$ | $CH_3$ | H | $CH_3$ | $CH_3$ | |
| 139 | 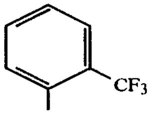 | $C_2H_5OOC$ | $C_2H_5OCH_2$ | H | H | H | |
| 140 | 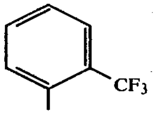 | $C_2H_5OOC$ | $CH_3$ | H | $CH_3$ | H | 207–208 |
| 141 | 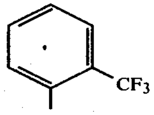 | $C_2H_5OOC$ | $CH_3$ | 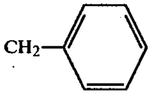 | H | H | |
| 142 | 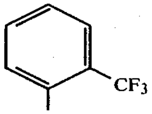 | $C_2H_5OOC$ | 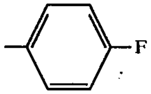 | H | H | H | |
| 143 | 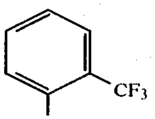 | $H_2NOC$ | $CH_3$ | H | H | H | |

-continued
| | | | | | | | |
|---|---|---|---|---|---|---|---|
| 144 | 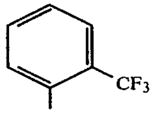 | $H_2NSC$ | $CH_3$ | H | H | H | |
| 145 | 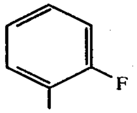 | $(CH_3)_2CHOOC$ | $CH_3$ | H | H | H | 182-184 |
| 146 | 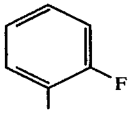 | 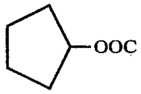 | $CH_3$ | H | H | H | ½ $H_2O$<br>115-117 |
| 147 | 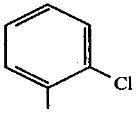 | $(CH_3)_2CHOOC$ | $CH_3$ | H | H | H | 176-178 |
| 148 | 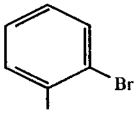 | $(CH_3)_2CHOOC$ | $CH_3$ | H | H | H | 158-160 |
| 149 | 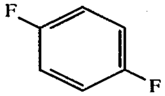 | $(CH_3)_2CHOOC$ | $CH_3$ | H | H | H | 185-187 |
| 150 | 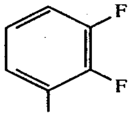 | $(CH_3)_2CHOOC$ | $CH_3$ | H | H | H | 175-177 |

-continued
| | | | | | | | |
|---|---|---|---|---|---|---|---|
| 151 | 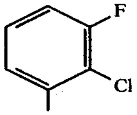 | $(CH_3)_2CHOOC$ | $CH_3$ | H | H | H | 205 |
| 152 | 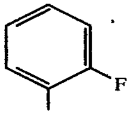 | $CH_3OCH_2CHOOC$ 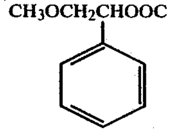 | $CH_3$ | H | H | H | amorphous* |
| 153 | 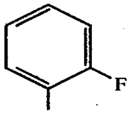 | $(CH_3)_2CHOOC$ | $CH_3$ | H | H | H | amorphous** |
*diastereomer, $[\alpha]_D = +93.1°$ (C = 1.12, $C_2H_5OH$), $[\alpha]_D = +213.1°$ (C = 1.15 $C_2H_5OH$)
**enantiomer, $[\alpha]_D = -122.1°$ (C = 1.028 $C_2H_5OH$), $[\alpha]_D = +123.6°$ (C = 1.046 $C_2H_5OH$)
| | | | | | | | |
|---|---|---|---|---|---|---|---|
| 154 | 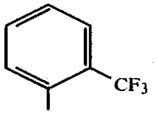 | $(C_2H_5)_2CHOOC$ | $CH_3$ | H | H | H | 147-149 |
| 155 | 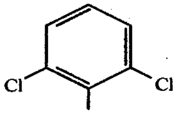 | $C_2H_5OOC$ | $CH_3$ | H | H | H | 218-219 |
| 156 | 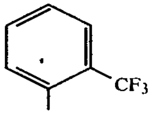 | $(CH_3)_2CHOOC$ | $CH_3$ | $CH_3$ | H | H | 136-137 |
| 157 | 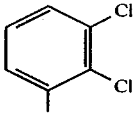 | $C_2H_5OOC$ | $CH_3$ | H | H | H | 213-214 |

-continued
| | | | | | | | |
|---|---|---|---|---|---|---|---|
| 158 | 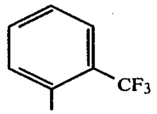 | $(CH_3)_2CHS\underset{\overset{\|}{O}}{C}$ | $CH_3$ | H | H | H | 183-185 |
| 159 | 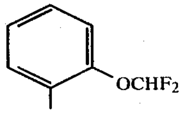 | $CH_3OOC$ | $CH_3$ | H | H | H | 175-177 |
| 160 | 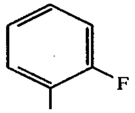 | $C_3H_7OOC$ | $CH_3$ | H | H | H | 162-164 |
| 161 | 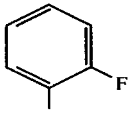 | $(CH_3)_3COOC$ | $CH_3$ | H | H | H | 179-181 |
| 162 | 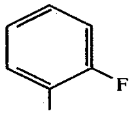 | $(CH_3)_2CHOOC$ | $CH_3$ | H | H | Br | 173-174 |
| 163 | 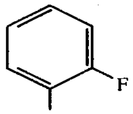 | $(CH_3)_2CHOOC$ | $CH_3$ | H | $CH_3$ | H | 185-186 |
| 164 | 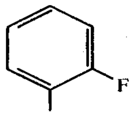 | $(CH_3)_2CHOOC$ | $CH_3$ | H | H | Cl | 163-164 |

-continued
| | | | | | | | |
|---|---|---|---|---|---|---|---|
| 165 | 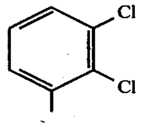 | $(CH_3)_2CHOOC$ | $CH_3$ | H | H | H | 196-198 |
| 166 | 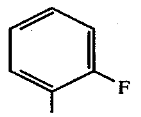 | $(CH_3)_2CHCH_2OOC$ | $CH_3$ | H | H | H | 150 |
| 167 | 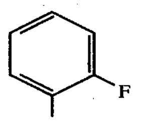 | $C_4H_9OOC$ | $CH_3$ | H | H | H | ⅛ $H_2O$ 164-165 |
| 168 | 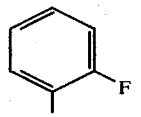 | $(CH_3)_2CHOOC$ | $CH_3$ | H | H | $CH_3$ | 219-220 |
| 169 | 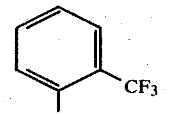 | $(CH_3)_2NCH_2CH_2OOC$ | $CH_3$ | H | H | H | 161-163 |
| 170 | 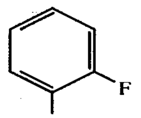 | $(CH_3)_2CHOOC$ | $C_2H_5$ | H | H | H | 98-99 |
| 171 | 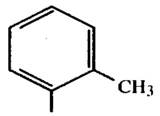 | $(CH_3)_2CHOOC$ | $CH_3$ | H | H | H | 177-178 |

-continued
| | | | | | | | |
|---|---|---|---|---|---|---|---|
| 172 | 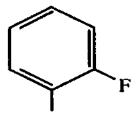 | $(CH_3)_2CHOOC$ | $CH_3$ | H | H | CN | 218–219 |
| 173 | 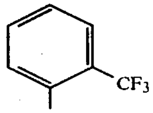 | $(CH_3)_2CHOOC$ | $CH_3$ | H | H | Cl | 171–172 |
| 174 | 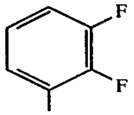 | $C_2H_5OOC$ | $CH_3$ | H | H | H | 185–186 |
| 175 | 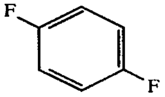 | $C_2H_5OOC$ | $CH_3$ | H | H | H | 199–200 |
| 176 | 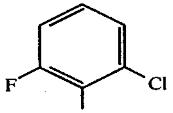 | $C_2H_5OOC$ | $CH_3$ | H | H | H | 173–175 |
| 177 | 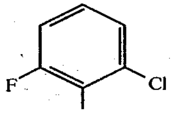 | $(CH_3)_2CHOOC$ | $CH_3$ | H | H | H | 132–134 |
| 178 | 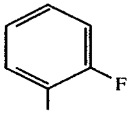 | $(CH_3)_2CHOOC$ | $CH(CH_3)_2$ | H | H | H | 183–185 |

-continued
| | | | | | | | |
|---|---|---|---|---|---|---|---|
| 179 | 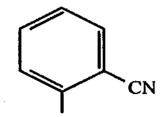 | $(CH_3)_2CHOOC$ | $CH_3$ | H | H | H | 185–187 |
| 180 | 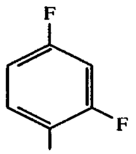 | $C_2H_5OOC$ | $CH_3$ | H | H | H | 157–159 |
| 181 | 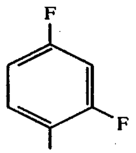 | $(CH_3)_2CHOOC$ | $CH_3$ | H | H | H | 144–145 |
| 182 | 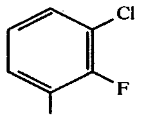 | $C_2H_5OOC$ | $CH_3$ | H | H | H | 205–206 |
| 183 | 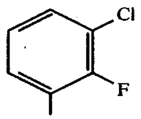 | $(CH_3)_2CHOOC$ | $CH_3$ | H | H | H | 180–181 |
| 184 | 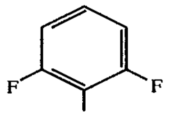 | $C_2H_5OOC$ | $CH_3$ | H | H | H | 144–146 |
| 185 | 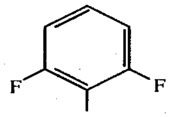 | $(CH_3)_2CHOOC$ | $CH_3$ | H | H | H | 143–144 |

-continued
| | | | | | | | |
|---|---|---|---|---|---|---|---|
| 186 | 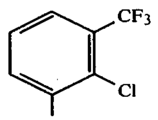 | $C_2H_5OOC$ | $CH_3$ | H | H | H | 208-210 |
| 187 | 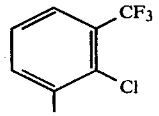 | $(CH_3)_2CHOOC$ | $CH_3$ | H | H | H | 204-206 |
| 188 | 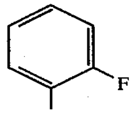 | $(CH_3)_2CHOOC$ | $CH_2OH$ | H | H | H | 168-170 |
| 189 | 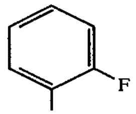 | $(CH_3)_2CHOOC$ | $C_4H_9$ | H | H | H | 155-157 |
| 190 | 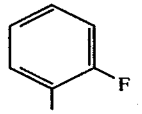 | $(CH_3)_2CHOOC$ | $CH_3$ | H | H | $CH(CH_3)_2$ | 186-188 |
| 191 | 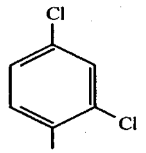 | $(CH_3)_2CHOOC$ | $CH_3$ | H | H | H | 198-200 |
| 192 | 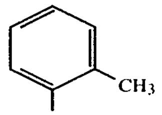 | $(CH_3)_2CHOOC$ | $CH_3$ | H | H | CN | 220-222 |

-continued
| | | | | | | | |
|---|---|---|---|---|---|---|---|
| 193 | 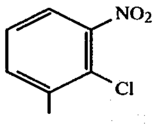 | $C_2H_5OOC$ | $CH_3$ | H | H | H | 166-199 |
| 194 | 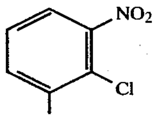 | $(CH_3)_2CHOOC$ | $CH_3$ | H | H | H | 228-229 |
| 195 | 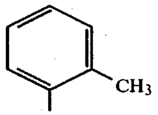 | $(CH_3)_2CHCH_2OOC$ | $CH_3$ | H | H | H | 185-186 |
| 196 | 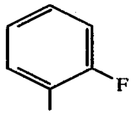 | $(CH_3)_2CHOOC$ | $CH_3$ | H | F | H | 167-168 |
| 197 | 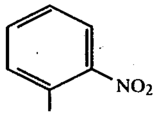 | $(CH_3)_2CHOOC$ | $CH_3$ | H | H | CN | 224-226 |
| 198 | 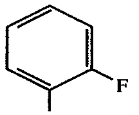 | $(CH_3)_2CHOOC$ | $CH_2F$ | H | H | H | 126-127 |
| 199 | 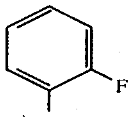 | $(CH_3)_2CHOOC$ | $CH_2CH_2OH$ | H | H | H | 186-187 |

-continued
| | | | | | | | |
|---|---|---|---|---|---|---|---|
| 200 | 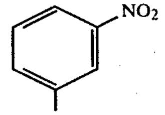 | $(CH_3)_2CHOOC$ | $CH_3$ | H | H | CN | 218-220 |
| 201 | 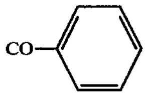 | $C_2H_5OOC$ | 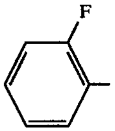 | H | H | H | 211-212 |
| 202 | 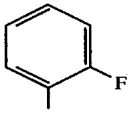 | CN | $CN_3$ | H | H | H | 215-217 |
| 203 | 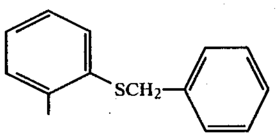 | $(CH_3)_2CHOOC$ | $CH_3$ | H | H | H | |
| 204 | 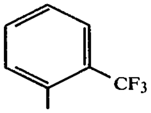 | $(CH_3)_2CHOOC$ | $C_4H_9$ | H | H | H | 133-135 |
| 205 | 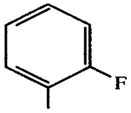 | $(CH_3)_2CHOOC$ | $CH_2OCOCH_3$ | H | H | H | |
(d: decomposition)

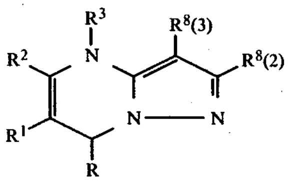
| No. | R | $R^1$ | $R^2$ | $R^3$ | $R^8(2)$ | $R^8(3)$ | M.p. (°C.) |
|---|---|---|---|---|---|---|---|
| 206 | 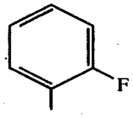 | $(CH_3)_2CHOOC$ | $CH_3$ | H | H | $NO_2$ | 175-177 |
| 207 | 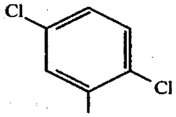 | $(CH_3)_2CHOOC$ | $CH_3$ | H | H | H | 191-192 |
| 208 | 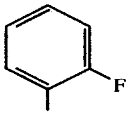 | $(CH_3)_2CHOOC$ | $CH_2Cl$ | H | H | H | |
| 209 | 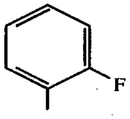 | $(CH_3)_2CHOOC$ | $CH_2N(C_2H_5)_2$ | H | H | H | |
| 210 | 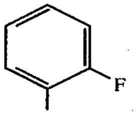 | 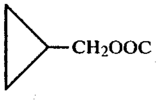 | $CH_3$ | H | H | H | 177-179 |
| 211 | 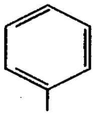 | $(CH_3)_2CHOOC$ | $CH_3$ | H | H | H | 193-194 |

-continued
| | | | | | | | |
|---|---|---|---|---|---|---|---|
| 212 | 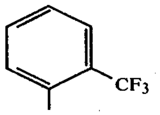 | $(CH_3)_2CHOOC$ | $CH_3$ | $COOC_2H_5$ | H | H | 60-61 |
| 213 | 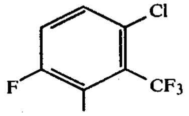 | $C_2H_5OOC$ | $CH_3$ | H | H | H | 204-205.5 |
| 214 | 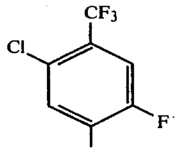 | $(CH_3)_2CHOOC$ | $CH_3$ | H | H | H | 201.5-202.5 |
| 215 | 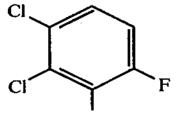 | $C_2H_5OOC$ | $CH_3$ | H | H | H | 196-198 |
| 216 | 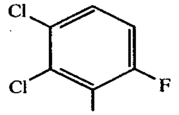 | $(CH_3)_2CHOOC$ | $CH_3$ | H | H | H | 178-181 |
| 217 | 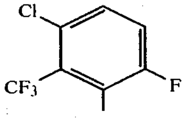 | $(CH_3)_2CHOOC$ | $CH_3$ | H | H | H | 211-212 |
| 218 | 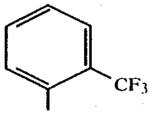 | $(ClCH_2)_2CHOOC$ | $CH_3$ | H | H | H | 186-187 |

-continued
| | | | | | | | |
|---|---|---|---|---|---|---|---|
| 219 | 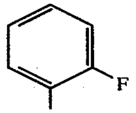 | $ClCH_2CH_2OOC$ | $CH_3$ | H | H | H | 142–144 |
| 220 | 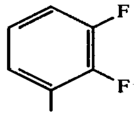 | $(CH_3)_2CHOOC$ | $CH_3$ | H | H | CN | 191–193 |
| 221 | 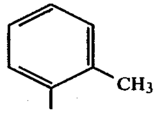 | 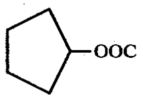 | $CH_3$ | H | H | H | 182–183 |
| 222 | 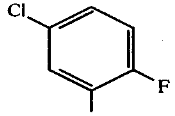 | $(CH_3)_2CHOOC$ | $CH_3$ | H | H | H | 179–181 |
| 223 | 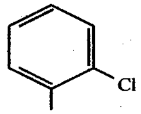 | 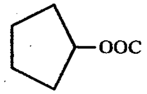 | $CH_3$ | H | H | H | 156–157 |
| 224 | 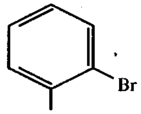 | 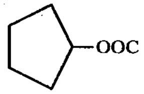 | $CH_3$ | H | H | H | 172–173 |
| 225 | 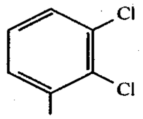 | $(CH_3)_3COOC$ | $CH_3$ | H | H | H | 212–213 |

-continued
| | | | | | | | |
|---|---|---|---|---|---|---|---|
| 226 | 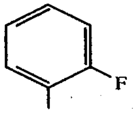 | $(CH_3)_2CHOOC$ | $CH_3$ | H | H | $CH_2OH$ | 155-156(d) |
| 227 | 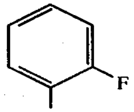 | $(CH_3)_2CHOOC$ | $CH_3$ | H | H | $CH_2OCOCH_3$ | |
| 228 | 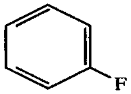 | $(CH_3)_2CHOOC$ | $Cl(CH_2)_3$ | H | H | H | 155-157 |
| 229 | 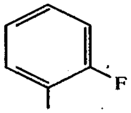 | $(CH_3)_2CHOOC$ | $CH_3COO(CH_2)_3$ | H | H | H | |
| 230 | 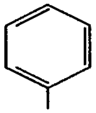 | 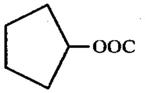 | $CH_3$ | H | H | H | 234-235 |
| 231 | 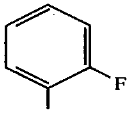 | $(CH_3)_2CHOOC$ | $CH_3COOCH_2CH_2$ | H | H | H | 156-157 |
| 232 | 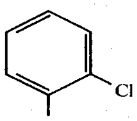 | $(CH_3)_3COOC$ | $CH_3$ | H | H | H | 186-188 |

-continued
| | | | | | | | |
|---|---|---|---|---|---|---|---|
| 233 | 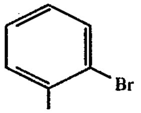 | $(CH_3)_3COOC$ | $CH_3$ | H | H | H | 205-206 |
| 234 | 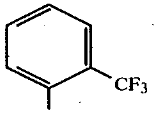 | $ClCH_2CH_2CH_2CH_2OOC$ | $CH_3$ | H | H | H | 153-154 |
| 235 | 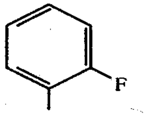 | $(CH_3)_2CHOOC$ | $CH_3$ | H | H | COOH | 198-200(d) |
| 236 | 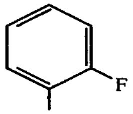 | $(ClCH_2)_2CHOOC$ | $CH_3$ | H | H | H | |
| 237 | 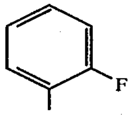 | $(CH_3)_2CHOOC$ | $CH_3COOCH_2$ | H | H | H | |
| 238 | 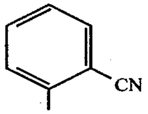 | $(CH_3)_3COOC$ | $CH_3$ | H | H | H | |
| 239 | 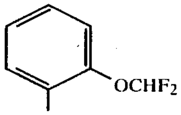 | $(CH_3)_3COOC$ | $CH_3$ | H | H | H | 138-140 |

-continued
| | | | | | | |
|---|---|---|---|---|---|---|
| 240 | 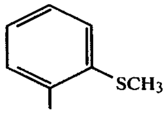 | $(CH_3)_2CHOOC$ | $CH_3$ | H | H | H |
| 241 | 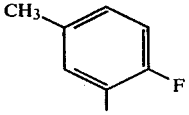 | $(CH_3)_2CHOOC$ | $CH_3$ | H | H | H |
| 242 | 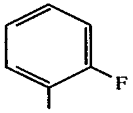 | 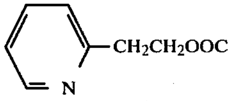 | $CH_3$ | H | H | H |
| 243 | 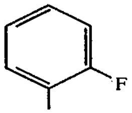 | 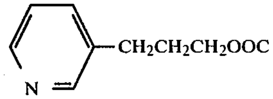 | $CH_3$ | H | H | H |
| 244 | 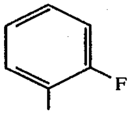 | 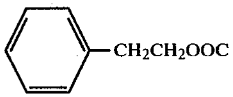 | $CH_3$ | H | H | H |
| 245 | 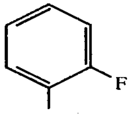 | 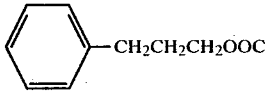 | $CH_3$ | H | H | H |
| 246 | 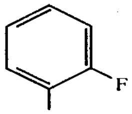 | $C_2H_5OOC$ | $H_2N$ | H | H | H |

-continued
| | | | | | | | |
|---|---|---|---|---|---|---|---|
| 247 | 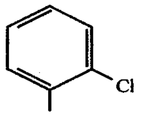 | H | $CH_3$ | H | H | H | |
| 248 | 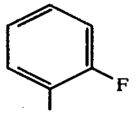 | $(CH_3)_2CHOOC$ | $CH_3$ | H | H | $COCH_3$ | |
| 249 | 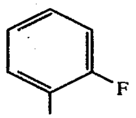 | $(CH_3)_2CHOOC$ | $CH_3$ | H | H | 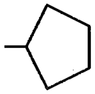 | |
| 250 | 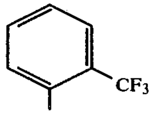 | $CH_3OCH_2CHOOC$ 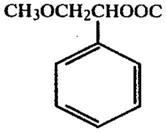 | $CH_3$ | H | H | H | α: 154-155*<br>β: 178-179** |
| 251 | 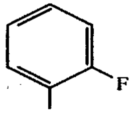 | $(CH_3)_2CHOOC$ | 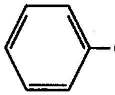 $-CH_2OCH_2CH_2$ | H | H | H | |
| 252 | 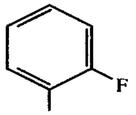 | $(CH_3)_2CHOOC$ | $CH_3-$ 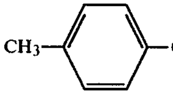 $-O(CH_2)_3$ | H | H | H | 134-136 |
| 253 | 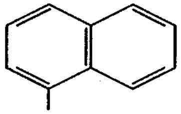 | $(CH_3)_2CHOOC$ | $CH_3$ | H | H | H | 194-195 |

-continued
| | | | | | | |
|---|---|---|---|---|---|---|
| 254 | 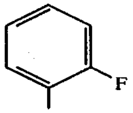 | $(CH_3)_2CHOOC$ | $CH_3$ | H | H | $CH_2F$ |
| 255 | 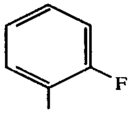 | $(CH_3)_3COOC$ | $CH_3$ | H | H | $CH_2CF_3$ |
| 256 | 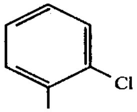 | $(CH_3)_2CHOOC$ | $CH_3$ | H | $CHF_2$ | H |
| 257 | 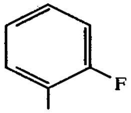 | 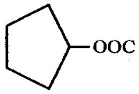 | $CH_3$ | H | H | $CH_2CH{=}CH_2$ |
| 258 | 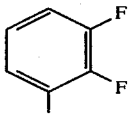 | $(CH_3)_2CHOOC$ | $CH_3$ | H | H | $C{\equiv}CH$ |
| 259 | 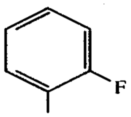 | $C_2H_5OOC$ | $CH_3$ | H | H | $CH_2OCH_2CH_3$ |
| 260 | 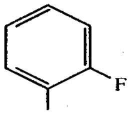 | $(CH_3)_2CHOOC$ | $CH_3$ | H | H | 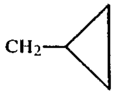 |

-continued
| | | | | | | |
|---|---|---|---|---|---|---|
| 261 | 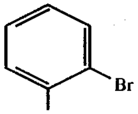 | $CH_3OOC$ | $CH_3$ | H | H | $(CH_2)_3CN$ |
| 262 | 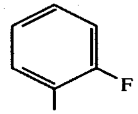 | 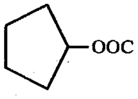 | $CH_3$ | H | H | $CH_2CH_2NO_2$ |
| 263 | 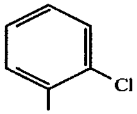 | $CH_3(CH_2)_3OOC$ | $CH_3$ | H | H | 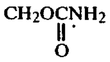 |
| 264 | 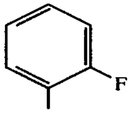 | $(CH_3)_2CHOOC$ | $CH_3$ | H | H | 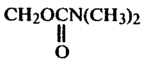 |
| 265 | 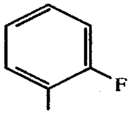 | $(CH_3)_2COOC$ | $CH_3$ | H | H | 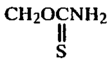 |
| 266 | 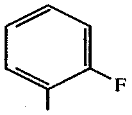 | $(CH_3)_2CHOOC$ | $CH_3$ | H | H | 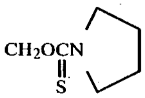 |
| 267 | 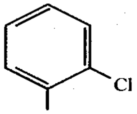 | $C_2H_5OOC$ | $CH_3$ | H | H | $CON(C_2H_5)_2$ |

-continued
| | | | | | | |
|---|---|---|---|---|---|---|
| 268 | 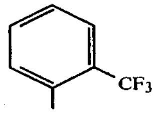 | $(CH_3)_2CHOOC$ | $CH_3$ | H | $CH_2CH{=}CH_2$ | H |
| 269 | 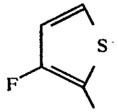 | $(CH_3)_2CHOOC$ | $CH_3$ | H | H | H |
| 270 | 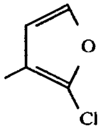 | $C_2H_5OOC$ | $CH_3$ | H | H | H |
| 271 | 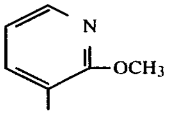 | $(CH_3)_2CHOOC$ | $CH_3$ | H | H | H |
| 272 | 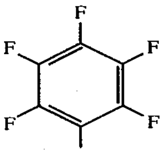 | $(CH_3)_2CHOOC$ | $CH_3$ | H | H | H |
| 273 | 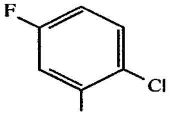 | $(CH_3)_3COOC$ | $CH_3$ | H | H | H |
| 274 | 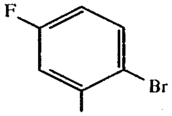 | $CH_3CH_2CH_2OOC$ | $CH_3$ | H | H | H |

-continued
| | | | | | | |
|---|---|---|---|---|---|---|
| 275 | 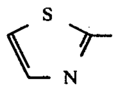 | $CH_3OOC$ | $CH_3$ | H | H | H |
| 276 | 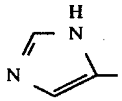 | 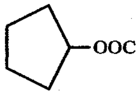 | $CH_3$ | H | H | H |
| 277 | 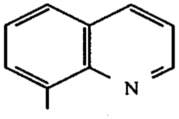 | $(CH_3)_2CHOOC$ | $CH_3$ | H | H | H |
| 278 | 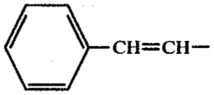 | $(CH_3)_2CHOOC$ | $CH_3$ | H | H | H |
| 279 | 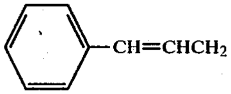 | $(CH_3)_3COOC$ | $CH_3$ | H | H | H |
| 280 | 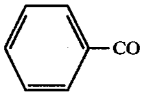 | $C_2H_5OOC$ | $CH_3$ | H | H | H |
| 281 | 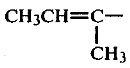 | $(CH_3)_2CHOOC$ | $CH_3$ | H | H | H |
| 282 | $CH\equiv C-CH_2-$ | $(CH_3)_3COOC$ | $CH_3$ | H | H | H |
| 283 | 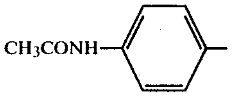 | $C_2H_5OOC$ | $CH_3$ | H | H | H |

-continued
| | | | | | | |
|---|---|---|---|---|---|---|
| 284 | 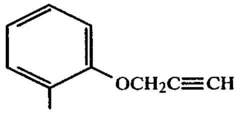 | $(CH_3)_2CHOOC$ | $CH_3$ | H | H | H |
| 285 | 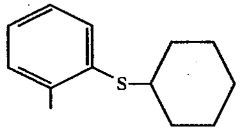 | $C_2H_5OOC$ | $CH_3$ | H | H | H |
| 286 | 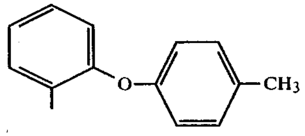 | $CH_3CH_2CH_2OOC$ | $CH_3$ | H | H | H |
| 287 | 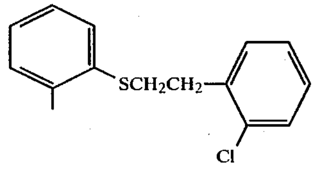 | $CH_3(CH_2)_3OOC$ | $CH_3$ | H | H | H |
| 288 | 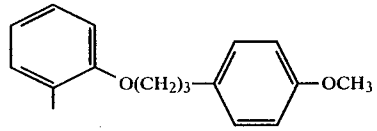 | 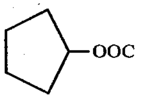 | $CH_3$ | H | H | H |
| 289 | 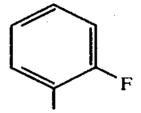 | $(CH_3)_2CHOOC$ | $CH_3$ | H | H | F |
| 290 | 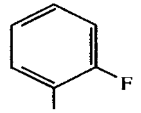 | $(CH_3)_2CHOOC$ | $(CH_2)_3OH$ | H | H | H |

-continued
| | | | | | | |
|---|---|---|---|---|---|---|
| 291 | 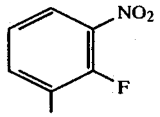 | $(CH_3)_2CHCH_2OOC$ | $CH_3$ | H | H | CN |
| 292 | 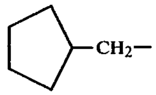 | $CH_3OOC$ | $CH_3$ | H | H | H |
| 293 | 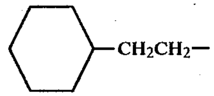 | 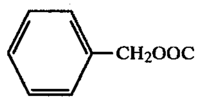 | $CH_3$ | H | H | H |
| 294 | 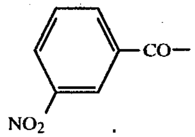 | $CH_3OCH_2CH_2OOC$ | $CH_3$ | H | H | H |
| 295 | 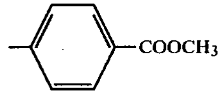 | $CH_3OOC$ | $CH_3$ | H | H | H |
| 296 | 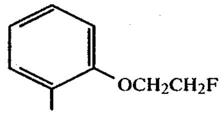 | $(CH_3)_2CHOOC$ | $CH_3$ | H | H | H |
| 297 | 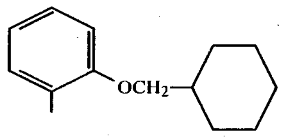 | 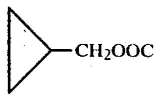 | $CH_3$ | H | H | H |
| 298 | 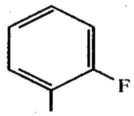 | $(CH_3)_2CHOSC$ | $CH_3$ | H | H | H |

-continued
| | | | | | | |
|---|---|---|---|---|---|---|
| 299 | 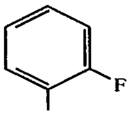 | $(CH_3)_2CHSSC$ | $CH_3$ | H | H | H |
| 300 | 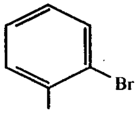 | $H_2NOC$ | $CH_3$ | H | H | H |
| 301 | 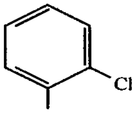 | 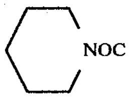 | $CH_3$ | H | H | H |
| 302 | 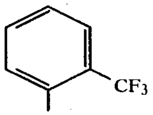 | $(CH_3)_2CHNHOC$ | $CH_3$ | H | H | H |
| 303 | 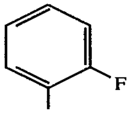 | $(C_2H_5)_2NOC$ | $CH_3$ | H | H | H |
| 304 | 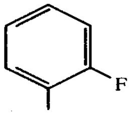 | $H_2NSC$ | $CH_3$ | H | H | H |
| 305 | 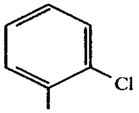 | 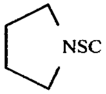 | $CH_3$ | H | H | H |

-continued
| | | | | | | |
|---|---|---|---|---|---|---|
| 306 | 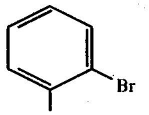 | (CH$_3$)$_3$CNHSC | CH$_3$ | H | H | H |
| 307 | 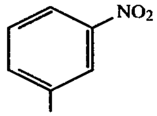 | 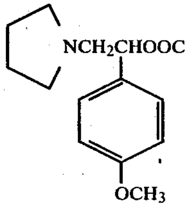 | CH$_3$ | H | H | H |
| 308 | 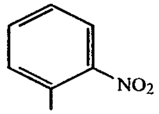 | 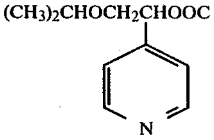 | CH$_3$ | H | H | H |
| 309 | 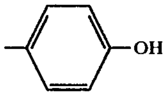 | 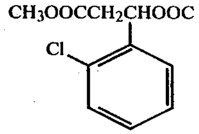 | CH$_3$ | H | H | H |
| 310 | 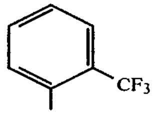 | 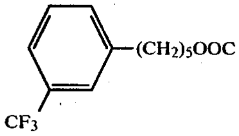 | CH$_3$ | H | H | H |
| 311 | 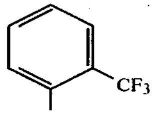 | C$_2$H$_5$OOC | 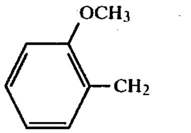 | H | H | H |
| 312 | 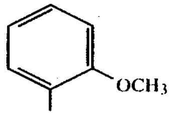 | CH$_3$OOC | 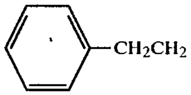 | H | H | H |
(d: decomposition)
*α: $[\alpha]_D$ — 144.4(C — 0.97,CHCl$_3$);
**β: $[\alpha]_D$ — 125.9(C — 1.05,CHCl$_3$)

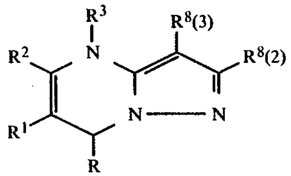
| No. | R | $R^1$ | $R^2$ | $R^3$ | $R^8(2)$ | $R^8(3)$ |
|---|---|---|---|---|---|---|
| 313 | 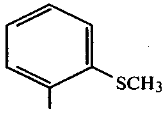 | $(CH_3)_2CHOOC$ | 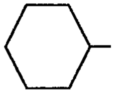 | H | H | H |
| 314 | 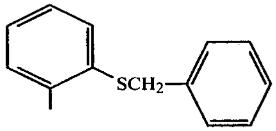 | $CH_3(CH_2)_2OOC$ | 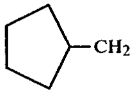 | H | H | H |
| 315 | 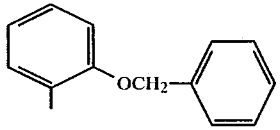 | $CH_3(CH_2)_3OOC$ | $H_2NCH_2CH_2$ | H | H | H |
| 316 | 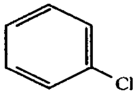 | $CH_3(CH_2)_3OOC$ | $CH_3CONHCH_2CH_2$ | H | H | H |
| 317 | 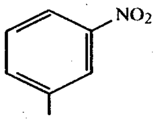 | $(CH_3)_2CHCH_2OOC$ | $HOCH_2CH_2OCH_2$ | H | H | H |
| 318 | 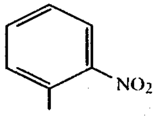 | $C_2H_5OOC$ | $H_2N(CH_2)_2OCH_2$ | H | H | H |

-continued
| | | | | | | |
|---|---|---|---|---|---|---|
| 319 | 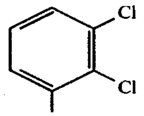 | $CH_3OOC$ | 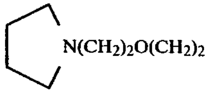 | H | H | H |
| 320 | 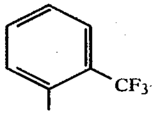 | $(CH_3)_2CHOOC$ | $CH_3$ | $C_3H_7$ | H | H |
| 321 | 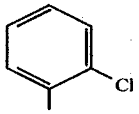 | $(CH_3)_3COOC$ | $CH_3$ | 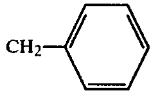 | H | H |
| 322 | 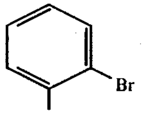 | $C_3H_7OOC$ | $CH_3$ | 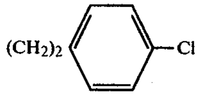 | H | H |
| 323 | 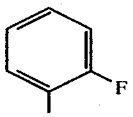 | 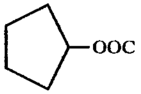 | $CH_3$ | 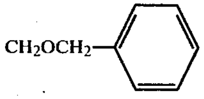 | H | H |
| 324 | 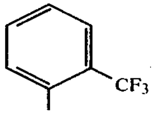 | $CH_3(CH_2)_3OOC$ | $CH_3$ | $COCH_3$ | H | H |
| 325 | 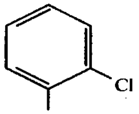 | $(CH_3)_2CHOOC$ | $CH_3$ | $CH_2CH_2Cl$ | H | H |

-continued
| | | | | | | |
|---|---|---|---|---|---|---|
| 326 | 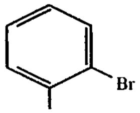 | $(CH_3)_3COOC$ | $CH_3$ | $(CH_2)_3OSO_2CH_3$ | H | H |
| 327 | 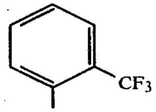 | 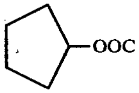 | $CH_3$ | $(CH_2)_4OSO_2$ 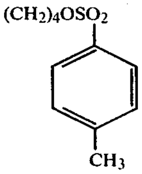 | H | H |
| 328 | 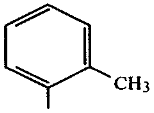 | $C_2H_5OOC$ | $CH_3$ | $CH_2CH_2OH$ | H | H |
| 329 | 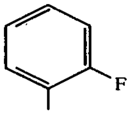 | $(CH_3)_2CHOOC$ | $CH_3$ | $CH_2CH_2N$ 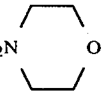 | H | H |
| 330 | 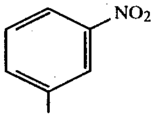 | $CH_3OOC$ | $CH_3$ | $(CH_2)_3N(C_2H_5)_2$ | H | H |
| 331 | 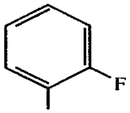 | 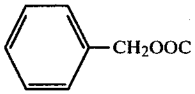 | $CH_3COO(CH_2)_3$ | H | H | H |
| 332 | 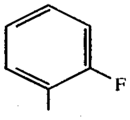 | 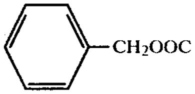 | $HO(CH_2)_3$ | H | H | H |

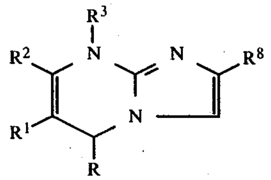
| No. | R | $R^1$ | $R^2$ | $R^3$ | $R^8$ | M.p. (°C.) |
|---|---|---|---|---|---|---|
| 333 | 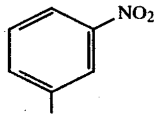 | $C_2H_5OOC$ | $CH_3$ | H | H | 242–243 |
| 334 | 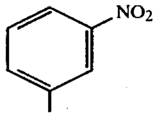 | $C_2H_5OOC$ | $CH_2Cl$ | H | H | 190–192(d) |
| 335 | 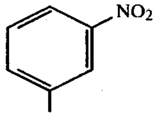 | $(CH_3)_3COOC$ | $CH_3$ | H | H | 219–222(d) |
| 336 | 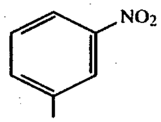 | $NCCH_2CH_2OOC$ | $CH_3$ | H | H | 230–237 |
| 337 | 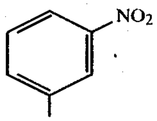 | $C_2H_5OOC$ | $CH_2OCONHCH_3$ | H | H | 207–208(d) |
| 338 | 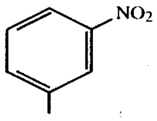 | $C_2H_5OOC$ | $CH_2OH$ | H | H | 196–197(d) |

-continued
| | | | | | | |
|---|---|---|---|---|---|---|
| 339 | 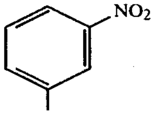 | $C_2H_5OOC$ | $CF_3$ | H | H | 240-242(d) |
| 340 | 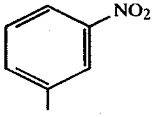 | 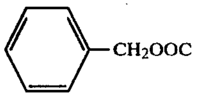 | $CH_3$ | H | H | 205 |
| 341 | 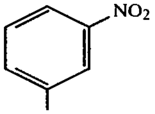 | $CH_3OCH_2CH_2OOC$ | $CH_3$ | H | H | 185-186 |
| 342 | 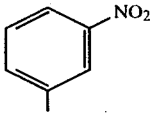 | $(CH_3)_2N(CH_2)_3OOC$ | $CH_3$ | H | H | |
| 343 | 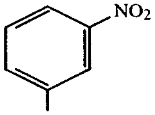 | $C_2H_5OOC$ | $C_3H_7$ | H | H | |
| 344 | 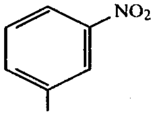 | HOOC | CHO | H | H | >350 |
| 345 | 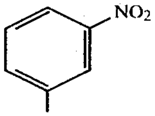 | H | $CH_3$ | H | H | 194-196(d) |

-continued
| | | | | | | |
|---|---|---|---|---|---|---|
| 346 | 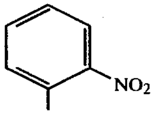 | $C_2H_5OOC$ | $CH_3$ | H | H | 253-254(d) |
| 347 | 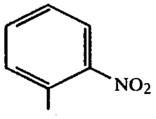 | $CH_3OOC$ | $CH_3$ | H | H | 256-258(d) |
| 348 | 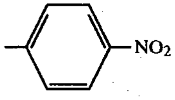 | $CH_3OOC$ | $CH_3$ | H | H | 249(d) |
| 349 | 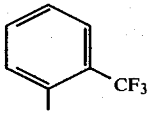 | $C_2H_5OOC$ | $CH_3$ | H | H | 276 |
| 350 | 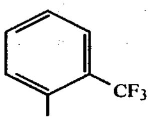 | $CH_3OOC$ | $CH_3$ | H | H | 285-286(d) |
| 351 | 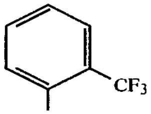 | $C_2H_5OOC$ | $CH_2OCOCH_3$ | H | H | 174-176 |
| 352 | 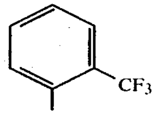 | 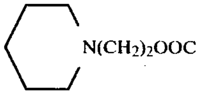 | $CH_3$ | H | H | 205-207(d) |

-continued
| | | | | | | |
|---|---|---|---|---|---|---|
| 353 | 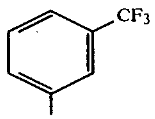 | $C_2H_5OOC$ | $CH_3$ | H | H | 193–194 |
| 354 | 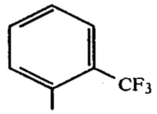 | $O_2NCH_2CH_2OOC$ | $CH_3$ | H | H | |
| 355 | 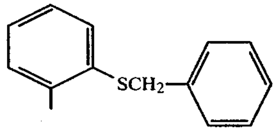 | $CH_3OOC$ | $CH_3$ | H | H | 196–198 |
| 356 | 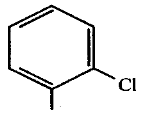 | $CH_3OOC$ | $CH_3$ | H | H | 257–258(d) |
| 357 | 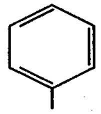 | $C_2H_5OOC$ | $CH_3$ | H | H | 183–184 |
| 358 | 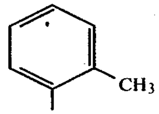 | $C_2H_5OOC$ | $CH_3$ | H | H | 215 |
| 359 | 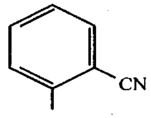 | $CH_3OOC$ | $CH_3$ | H | H | 268(d) |

-continued
| | | | | | | |
|---|---|---|---|---|---|---|
| 360 | 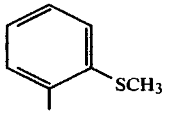 | $CH_3OOC$ | $CH_3$ | H | H | 259-260(d) |
| 361 | 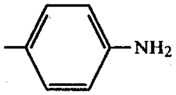 | $CH_3OOC$ | $CH_3$ | H | H | pale yellow crystals |
| 362 | 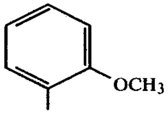 | $CH_3OOC$ | $CH_3$ | H | H | 242-245(d) |
| 363 | $C_3H_7$ | $C_2H_5OOC$ | $CH_3$ | H | H | 144-145 |
| 364 | 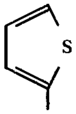 | $CH_3OOC$ | $CH_3$ | H | H | 230-232(d) |
| 365 | 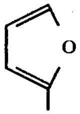 | $CH_3OOC$ | $CH_3$ | H | H | |
| 366 | H | $C_2H_5OOC$ | $CH_3$ | H | H | 248-249 |
| 367 | 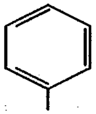 | H | $CH_3$ | H | H | |
| 368 | 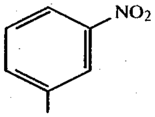 | $(C_4H_9)_2NCH_2CHOOC$ 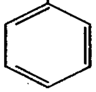 | $CH_3$ | H | H | α:146-147 β:174-175 |

-continued
| | | | | | | |
|---|---|---|---|---|---|---|
| 369 | 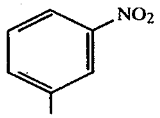 | 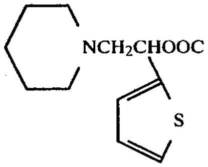 | $CH_3$ | H | H | α:204-206<br>β:182-183 |
| 370 | 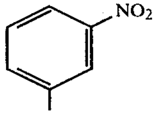 | 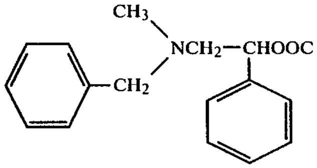 | $CH_3$ | H | H | α:193-194<br>β:188-190 |
| 371 | 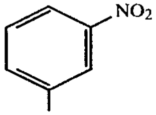 | 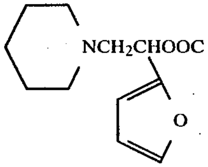 | $CH_3$ | H | H | α:199-200(d)<br>β:186-187(d) |
| 372 | 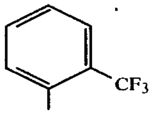 | $H_2NCO$ | $CH_3$ | H | H | 254-255 |
| 373 | 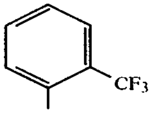 | NC | $CH_3$ | H | H | HCl<br>275-278 |
| 374 | 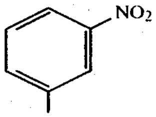 | 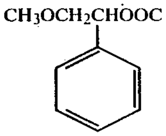 | $CH_3$ | H | H | α:194-195<br>β:184 |

-continued
| | | | | | | |
|---|---|---|---|---|---|---|
| | 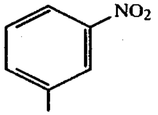 | $C_2H_5OOC$ | $CH_3$ | H | $CH_2OH$ | 220-221(d) |
| | 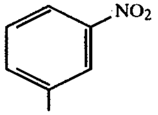 | $C_2H_5OOC$ | $CH_3$ | H | $CH_3$ | 246-247 |
| 375 | 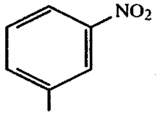 | $CH_3CO$ | $CH_3$ | H | H | |
| 376 | 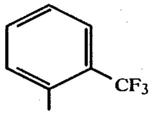 | 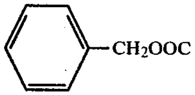 | $CH_3$ | H | H | |
| 377 | 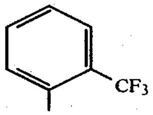 | HOOC | $CH_3$ | H | H | |
| 378 | 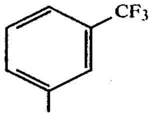 | $C_2H_5OOC$ | $CH_3$ | H | H | |
| 379 | 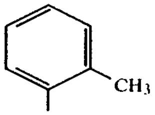 | $C_2H_5OOC$ | $CH_3$ | H | H | |

-continued
| | | | | | |
|---|---|---|---|---|---|
| 380 | 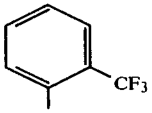 | $C_3H_7OOC$ | $CH_3$ | H | H |
| 381 | 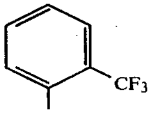 | $(CH_3)_2CHOOC$ | $CH_3$ | H | H |
| 382 | 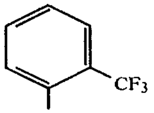 | $(CH_3)_2CHCH_2OOC$ | $CH_3$ | H | H |
| 383 | 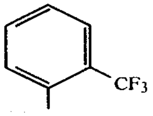 | $(CH_3)_3COOC$ | $CH_3$ | H | H |
| 384 | 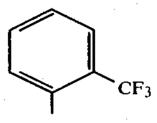 | 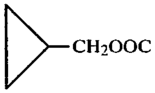 | $CH_3$ | H | H |
| 385 | 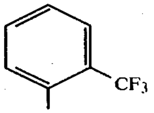 | 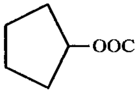 | $CH_3$ | H | H |
| 386 | 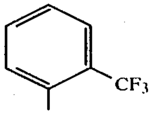 | $CH_3OCH_2CHOOC$ 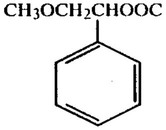 | $CH_3$ | H | H |

-continued
| | | | | | |
|---|---|---|---|---|---|
| 387 | 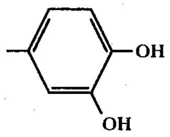 | $CH_3OOC$ | $CH_3$ | H | H |
| 388 | 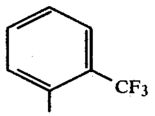 | $C_2H_5OOC$ | $CH_2OH$ | H | H |
| 389 | 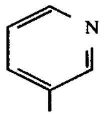 | $CH_3OOC$ | $CH_3$ | H | H |
| 390 | 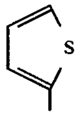 | $C_2H_5OOC$ | $C_3H_7$ | H | H |
| 391 | 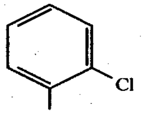 | $C_2H_5OOC$ | $CH_3$ | H | H |
| 392 | 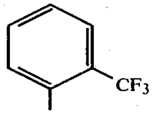 | $C_4H_9OOC$ | $CH_3$ | H | H |
| 393 | 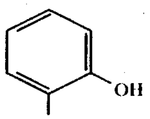 | $CH_3OOC$ | $CH_3$ | H | H |

-continued
| | | | | | |
|---|---|---|---|---|---|
| 394 | 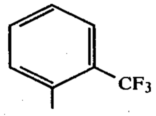 | $C_2H_5OOC$ | $CH_2Cl$ | H | H |
| 395 | 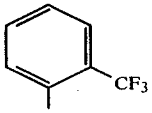 | $C_2H_5OOC$ | $CH_2F$ | H | H |
| 396 | 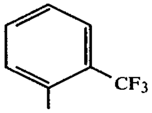 | 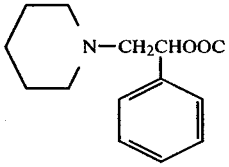 | $CH_3$ | H | H |
| 397 | 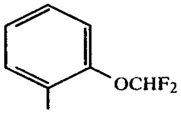 | $C_2H_5OOC$ | $CH_3$ | H | H |
| 398 | 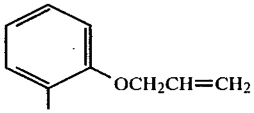 | $C_2H_5OOC$ | $CH_3$ | H | H |
| 399 | 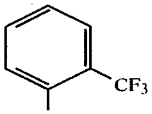 | $FCH_2CH_2OOC$ | $CH_3$ | H | H |
| 400 | 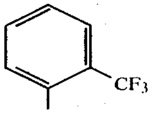 | $ClCH_2CH_2OOC$ | $CH_3$ | H | H |

-continued
| | | | | | |
|---|---|---|---|---|---|
| 401 | 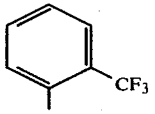 | $CF_3CH_2OOC$ | $CH_3$ | H | H |
| 402 | 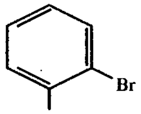 | $C_4H_9OOC$ | $CH_3$ | H | H |
| 403 | 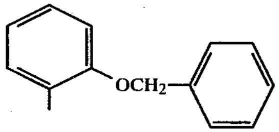 | 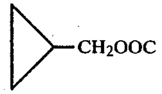 | $CH_3$ | H | H |
| 404 | 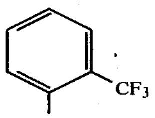 | 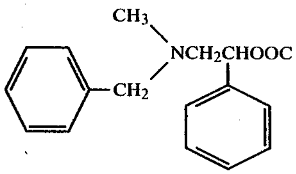 | $CH_3$ | H | H |
| 405 | 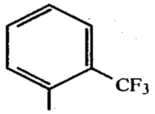 | $CH_3(CH_2)_7OOC$ | $CH_3$ | H | H |
| 406 | 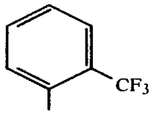 | $CH_3(CH_2)_5OOC$ | $CH_3$ | H | H |
| 407 | 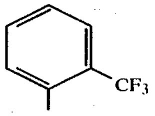 | $CH_2{=}CHCH_2OOC$ | $CH_3$ | H | H |

-continued
| | | | | | |
|---|---|---|---|---|---|
| 408 | 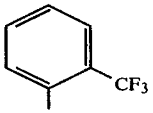 | 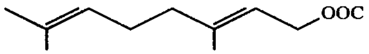 | $CH_3$ | H | H |
| 409 | 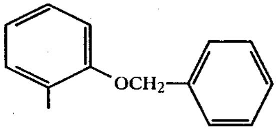 | $C_2H_5OOC$ | $CH_3$ | H | H |
| 410 | 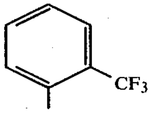 | $O_2N$ | $CH_3$ | H | H |
| 411 | 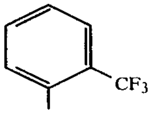 | 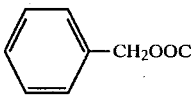 | $CH_3$ | $CH_2OC_2H_5$ | H |
| 412 | 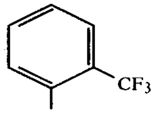 | HOOC | $CH_3$ | $CH_2OC_2H_5$ | H |
| 413 | 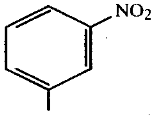 | $C_2H_5OOC$ | $(C_2H_5)_2NCH_2$ | H | H |
| 414 | 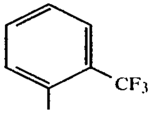 | $CH\equiv CCH_2OOC$ | $CH_3$ | H | H |

-continued
| | | | | | |
|---|---|---|---|---|---|
| 415 | 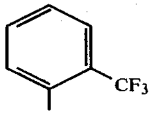 | $CH_3S(CH_2)_2OOC$ | $CH_3$ | H | H |
| 416 | 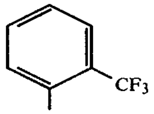 | $CH_3(CH_2)_4OOC$ | $CH_3$ | H | H |
| 417 | 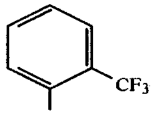 | 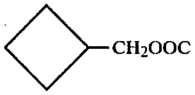 | $CH_3$ | H | H |
| 418 | 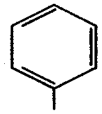 | $CH_3OOC$ | $CH_3$ | H | H |
| 419 | 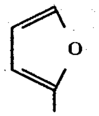 | $C_2H_5OOC$ | $C_3H_7$ | H | H |
| 420 | 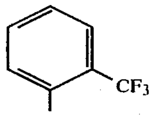 | $CH_3(CH_2)_{21}OOC$ | $CH_3$ | H | H |
| 421 | 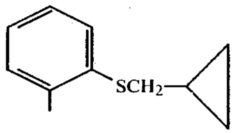 | $C_2H_5OOC$ | $CH_3$ | H | H |

-continued
| | | | | | |
|---|---|---|---|---|---|
| 422 | 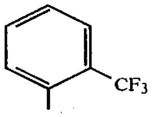 | 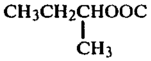 | $CH_3$ | H | H |
| 423 | 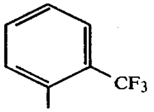 | 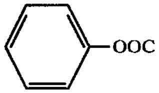 | $CH_3$ | H | H |
| 424 | 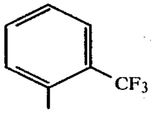 | 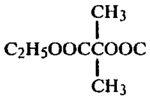 | $CH_3$ | H | H |
| 425 | 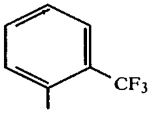 | $C_2H_5OOC$ | $CF_3$ | H | H |
| 426 | 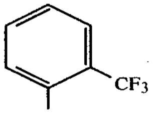 | $CH_3(CH_2)_{15}OOC$ | $CH_3$ | H | H |
| 427 | 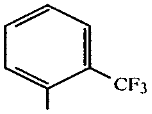 | 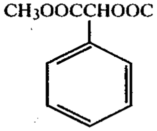 | $CH_3$ | H | H |
| 428 | 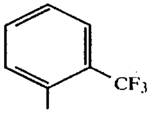 | 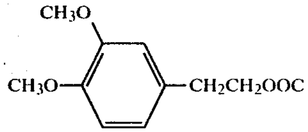 | $CH_3$ | H | H |

-continued
| | | | | | |
|---|---|---|---|---|---|
| 429 | 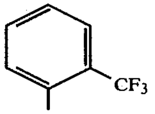 | 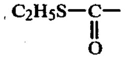 | $CH_3$ | H | H |
| 430 | 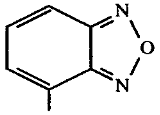 | $O_2N$ | $CH_3$ | H | H |
| 431 | 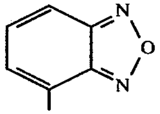 | $C_2H_5OOC$ | $CH_3$ | H | H |
| 432 | 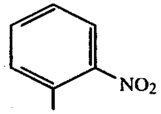 | $C_2H_5OOC$ | $CH_3$ | H | H |
| 433 | 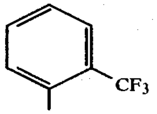 | 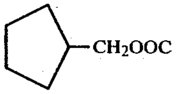 | $CH_3$ | H | H |
| 434 | 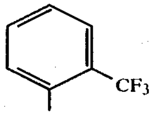 | 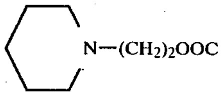 | $CH_3$ | H | H |
| 435 | 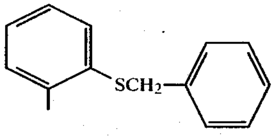 | $C_2H_5OOC$ | $CH_3$ | H | H |

-continued
| | | | | | |
|---|---|---|---|---|---|
| 436 | 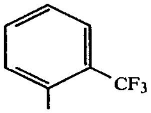 | 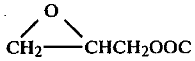 | $CH_3$ | H | H |
| 437 | 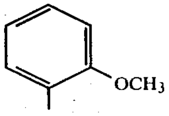 | $C_2H_5OOC$ | $CH_3$ | H | H |
| 438 | 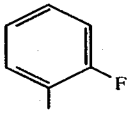 | $C_2H_5OOC$ | $CH_3$ | H | H |
| 439 | 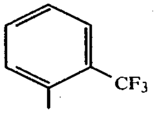 | 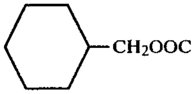 | $CH_3$ | H | H |
| 440 | 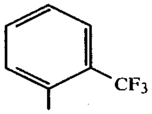 | $(CH_3)_3CCH_2OOC$ | $CH_3$ | H | H |
| 441 | 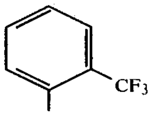 | 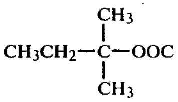 | $CH_3$ | H | H |
| 442 | 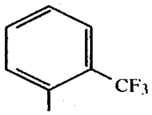 | 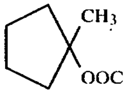 | $CH_3$ | H | H |

-continued
| | | | | | |
|---|---|---|---|---|---|
| 443 | 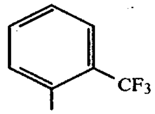 | $C_2H_5OOC$ | $C_3H_7$ | H | H |
| 444 | 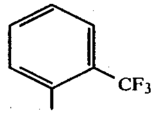 | $C_2H_5OOC$ | $C_2H_5OCH_2$ | H | H |
| 445 | 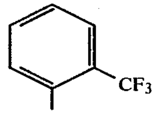 | $C_2H_5OOC$ | $CH_3$ | $CH_3$ | H |
| 446 | 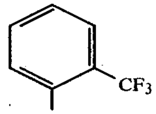 | $C_2H_5OOC$ | $CH_3$ | 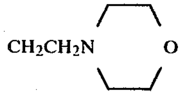 | H |
| 447 | 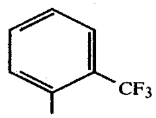 | 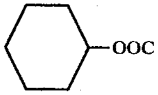 | $CH_3$ | H | H |
| 448 | 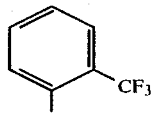 | $H_2NSC$ | $CH_3$ | H | H |
| 449 | 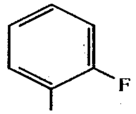 | $(CH_3)_2CHOOC$ | $CH_3$ | H | H |

-continued
| | | | | | |
|---|---|---|---|---|---|
| 450 | 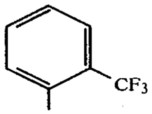 | $C_2H_5OOC$ | $CH_3$ | 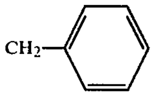 | H |
| 451 | 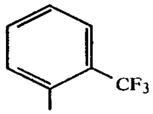 | $C_2H_5OOC$ | 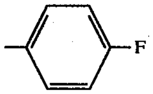 | H | H |
| 452 | 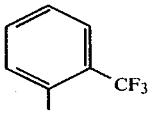 | $C_2H_5OOC$ | Cl | H | H |
| 453 | 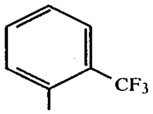 | $C_2H_5OOC$ | $(C_2H_5)_2NCH_2$ | H | H |
| 454 | 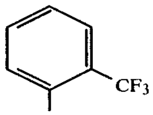 | $C_2H_5OOC$ | $CH_3NHCOOCH_2$ | H | H |
| 455 | 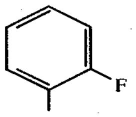 | $(CH_3)_2CHOOC$ | $C_2H_5$ | H | H |
| 456 | 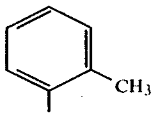 | $(CH_3)_2CHOOC$ | $CH_3$ | H | H |

-continued
| | | | | | |
|---|---|---|---|---|---|
| 457 | 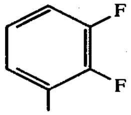 | $C_2H_5OOC$ | $CH_3$ | H | H |
| 458 | 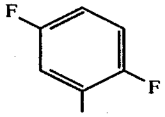 | $C_2H_5OOC$ | $CH_3$ | H | H |
| 459 | 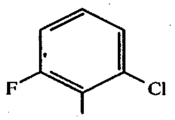 | $C_2H_5OOC$ | $CH_3$ | H | H |
| 460 | 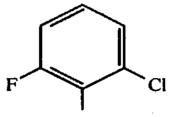 | $(CH_3)_2CHOOC$ | $CH_3$ | H | H |
| 461 | 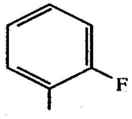 | $(CH_3)_2CHOOC$ | $CH(CH_3)_2$ | H | H |
| 462 | 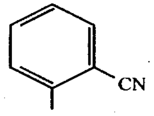 | $(CH_3)_2CHOOC$ | $CH_3$ | H | H |
| 463 | 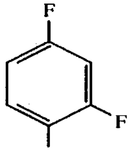 | $C_2H_5OOC$ | $CH_3$ | H | H |

-continued
| | | | | | |
|---|---|---|---|---|---|
| 464 | 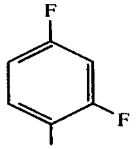 | $(CH_3)_2CHOOC$ | $CH_3$ | H | H |
| 465 | 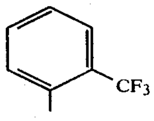 | $C_2H_5OOC$ | $(C_2H_5)_2N$ | H | H |
| 466 | 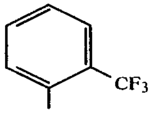 | $C_2H_5OOC$ | $(CH_3)_3C$ | H | H |
| 467 | 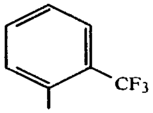 | $C_2H_5OOC$ | $CH_3NHCSOCH_2$ | H | H |
| 468 | 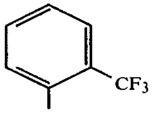 | $(CH_3)_2NCH_2CH_2OOC$ | $CH_3$ | H | H |
| 469 | 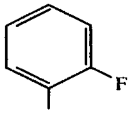 | 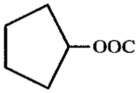 | $CH_3$ | H | H |
| 470 | 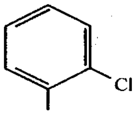 | $(CH_3)_2CHOOC$ | $CH_3$ | H | H |

-continued
| | | | | | |
|---|---|---|---|---|---|
| 471 | 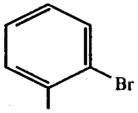 | $(CH_3)_2CHOOC$ | $CH_3$ | H | H |
| 472 | 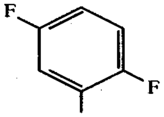 | $(CH_3)_2CHOOC$ | $CH_3$ | H | H |
| 473 | 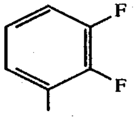 | $(CH_3)_2CHOOC$ | $CH_3$ | H | H |
| 474 | 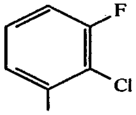 | $(CH_3)_2CHOOC$ | $CH_3$ | H | H |
| 475 | 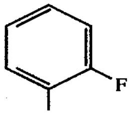 | $CH_3OCH_2CHOOC$ 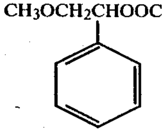 | $CH_3$ | H | H |
| 476 | 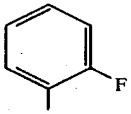 | $(CH_3)_2CHOOC$ | $CH_3$ | H | H |
| 477 | 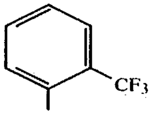 | $(C_2H_5)_2CHOOC$ | $CH_3$ | H | H |

-continued
| | | | | | |
|---|---|---|---|---|---|
| 478 | 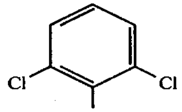 | $C_2H_5OOC$ | $CH_3$ | H | H |
| 479 | 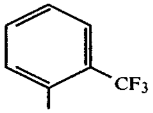 | $(CH_3)_2CHOOC$ | $CH_3$ | $CH_3$ | H |
| 480 | 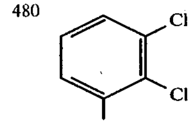 | $C_2H_5OOC$ | $CH_3$ | H | H |
d: decomposition

| | | | | | |
|---|---|---|---|---|---|
| 481 | 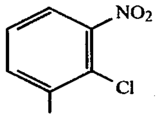 | $(CH_3)_2CHOOC$ | $CH_3$ | H | H |
| 482 | 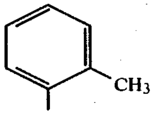 | $(CH_3)_2CHCH_2OOC$ | $CH_3$ | H | H |
| 483 | 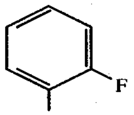 | $(CH_3)_2CHOOC$ | $CH_3$ | H | F |
| 484 | 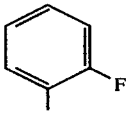 | $(CH_3)_2CHOOC$ | $CH_3$ | H | H |
| 485 | 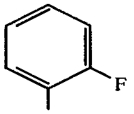 | $(CH_3)_2CHOOC$ | $CH_2F$ | H | H |
| 486 | 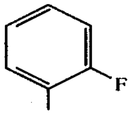 | $(CH_3)_2CHOOC$ | $CH_2CH_2OH$ | H | H |
| 487 | 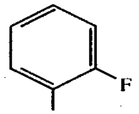 | $(CH_3)_2CHOOC$ | $(CH_2)_3OH$ | H | H |

-continued
| | | | | | |
|---|---|---|---|---|---|
| 488 | 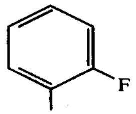 | $C_2H_5OOC$ | 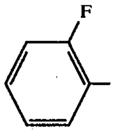 | H | H |
| 489 | 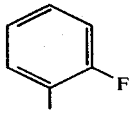 | CN | $CH_3$ | H | H |
| 490 | 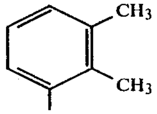 | $(CH_3)_2CHOOC$ | $CH_3$ | H | H |
| 491 | 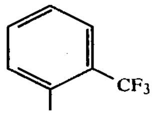 | $(CH_3)_2CHOOC$ | $C_4H_9$ | H | H |
| 492 | 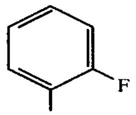 | $(CH_3)_2CHOOC$ | $CH_2OCOCH_3$ | H | H |
| 493 | 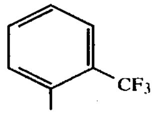 | $(CH_3)_2CHSC(=O)$ | $CH_3$ | H | H |
| 494 | 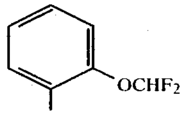 | $CH_3OOC$ | $CH_3$ | H | H |

-continued
| | | | | | |
|---|---|---|---|---|---|
| 495 | 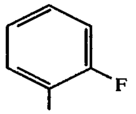 | $C_3H_7OOC$ | $CH_3$ | H | H |
| 496 | 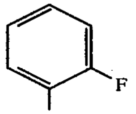 | $(CH_3)_3COOC$ | $CH_3$ | H | H |
| 497 | 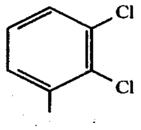 | $(CH_3)_3COOC$ | $CH_3$ | H | H |
| 498 | 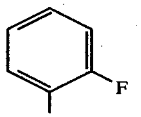 | $(CH_3)_2CHCH_2OOC$ | $CH_3$ | H | H |
| 499 | 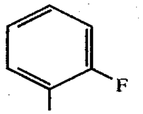 | $C_4H_9OOC$ | $CH_3$ | H | H |
| 500 | 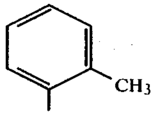 | 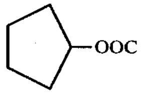 | $CH_3$ | H | H |
| 501 | 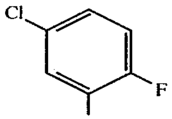 | $(CH_3)_2CHOOC$ | $CH_3$ | H | H |

-continued
| | | | | | |
|---|---|---|---|---|---|
| 502 | 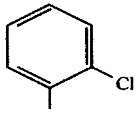 | 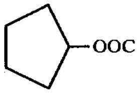 | $CH_3$ | H | H |
| 503 | 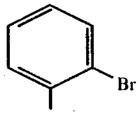 | 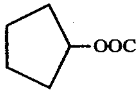 | $CH_3$ | H | H |
| 504 | 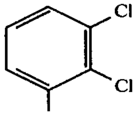 | $(CH_3)_3COOC$ | $CH_3$ | H | H |
| 505 | 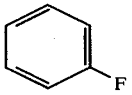 | $(CH_3)_2CHOOC$ | $Cl(CH_2)_3$ | H | H |
| 506 | 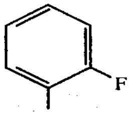 | $(CH_3)_2CHOOC$ | $CH_3COO(CH_2)_3$ | H | H |
| 507 | 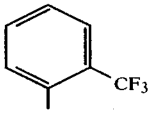 | $(ClCH_2)_2CHOOC$ | $CH_3$ | H | H |
| 508 | 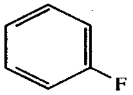 | $ClCH_2CH_2OOC$ | $CH_3$ | H | H |
| 509 | 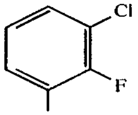 | $C_2H_5OOC$ | $CH_3$ | H | H |

-continued
| | | | | | |
|---|---|---|---|---|---|
| 510 | 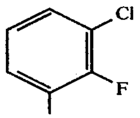 | $(CH_3)_2CHOOC$ | $CH_3$ | H | H |
| 511 | 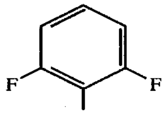 | $C_2H_5OOC$ | $CH_3$ | H | H |
| 512 | 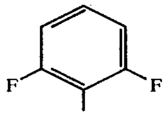 | $(CH_3)_2CHOOC$ | $CH_3$ | H | H |
| 513 | 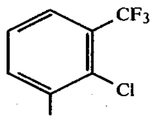 | $C_2H_5OOC$ | $CH_3$ | H | H |
| 514 | 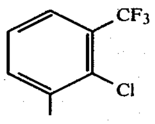 | $(CH_3)_2CHOOC$ | $CH_3$ | H | H |
| 515 | 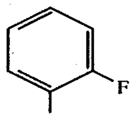 | $(CH_3)_2CHOOC$ | $CH_2OH$ | H | H |
| 516 | 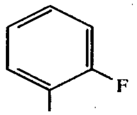 | $(CH_3)_2CHOOC$ | $C_4H_9$ | H | H |

-continued
| | | | | | |
|---|---|---|---|---|---|
| 517 | 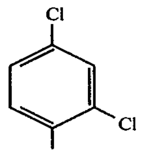 | $(CH_3)_2CHOOC$ | $CH_3$ | H | H |
| 518 | 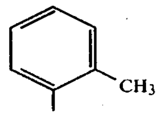 | $(CH_3)_2CHOOC$ | $CH_3$ | H | H |
| 519 | 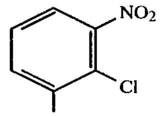 | $C_2H_5OOC$ | $CH_3$ | H | H |
| 520 | 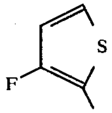 | $(CH_3)_2CHOOC$ | $CH_3$ | H | H |
| 521 | 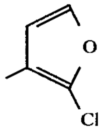 | $C_2H_5OOC$ | $CH_3$ | H | H |
| 522 | 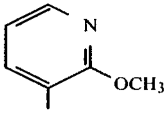 | $(CH_3)_2CHOOC$ | $CH_3$ | H | H |
| 523 | 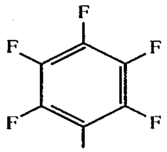 | $(CH_3)_2CHOOC$ | $CH_3$ | H | H |

-continued
| | | | | | |
|---|---|---|---|---|---|
| 524 | 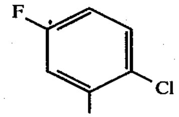 | $(CH_3)_3COOC$ | $CH_3$ | H | H |
| 525 | 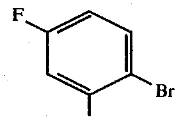 | $CH_3CH_2CH_2OOC$ | $CH_3$ | H | H |
| 526 | 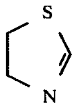 | $CH_3OOC$ | $CH_3$ | H | H |
| 527 | 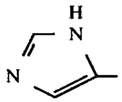 | 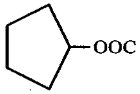 | $CH_3$ | H | H |
| 528 | 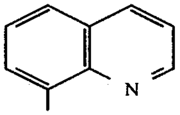 | $(CH_3)_2CHOOC$ | $CH_3$ | H | H |
| 529 | 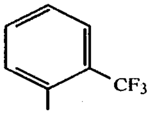 | $(CH_3)_2CHNHOC$ | $CH_3$ | H | H |
| 530 | 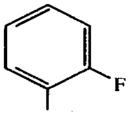 | $(C_2H_5)_2NOC$ | $CH_3$ | H | H |
| 531 | 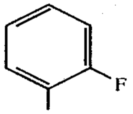 | $H_2NSC$ | $CH_3$ | H | H |

-continued
| | | | | | |
|---|---|---|---|---|---|
| 532 | 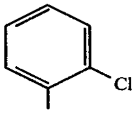 | 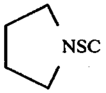 | $CH_3$ | H | H |
| 533 | 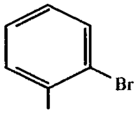 | $(CH_3)_3CNHSC$ | $CH_3$ | H | H |
| 534 | 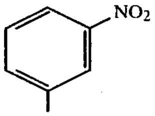 | 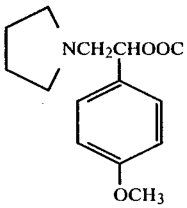 | $CH_3$ | H | H |
| 535 | 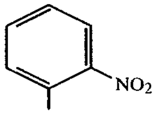 | 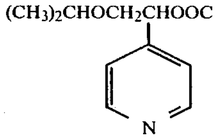 | $CH_3$ | H | H |
| 536 | 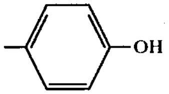 | 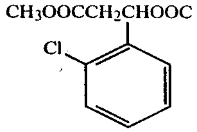 | $CH_3$ | H | H |
| 537 | 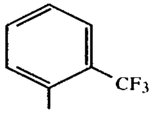 | 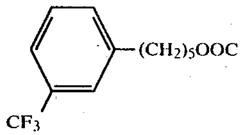 | $CH_3$ | H | H |

-continued
| | | | | | |
|---|---|---|---|---|---|
| 538 | 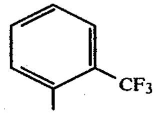 | $C_2H_5OOC$ | 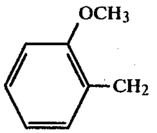 | H | H |
| 539 | 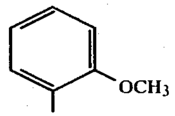 | $CH_3OOC$ | 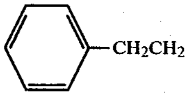 | H | H |
| 540 | 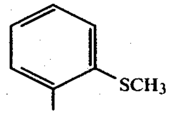 | $(CH_3)_2CHOOC$ | 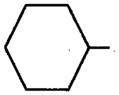 | H | H |
| 541 | 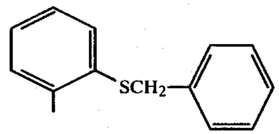 | $CH_3(CH_2)_2OOC$ | 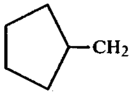 | H | H |
| 542 | 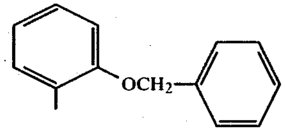 | $CH_3(CH_2)_3OOC$ | $H_2NCH_2CH_2$ | H | H |
| 543 | 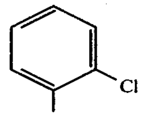 | $CH_3(CH_2)_3OOC$ | $CH_3CONHCH_2CH_2$ | H | H |
| 544 | 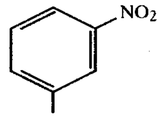 | $(CH_3)_2CHCH_2OOC$ | $HOCH_2CH_2OCH_2$ | H | H |

-continued
| | | | | | |
|---|---|---|---|---|---|
| 545 | 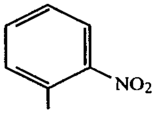 | $C_2H_5OOC$ | $H_2N(CH_2)_2OCH_2$ | H | H |
| 546 | 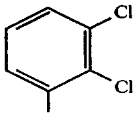 | $CH_3OOC$ | 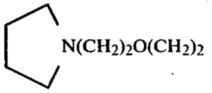 | H | H |
| 547 | 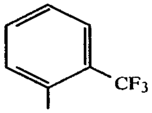 | $(CH_3)_2CHOOC$ | $CH_3$ | $C_3H_7$ | H |
| 548 | 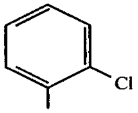 | $(CH_3)_3COOC$ | $CH_3$ | 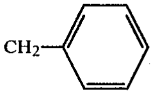 | H |
| 549 | 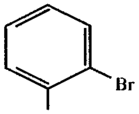 | $C_3H_7OOC$ | $CH_3$ | 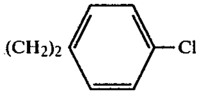 | H |
| 550 | 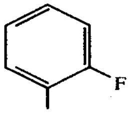 | 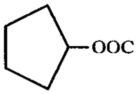 | $CH_3$ | 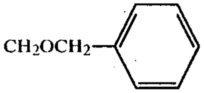 | H |
| 551 | 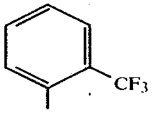 | $CH_3(CH_2)_3OOC$ | $CH_3$ | $COCH_3$ | H |

-continued
| | | | | |
|---|---|---|---|---|
| 552 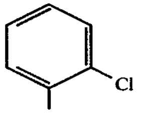 | $(CH_3)_2CHOOC$ | $CH_3$ | $CH_2CH_2Cl$ | H |
| 553 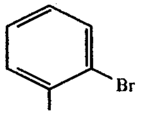 | $(CH_3)_3COOC$ | $CH_3$ | $(CH_2)_3OSO_2CH_3$ | H |
| 554 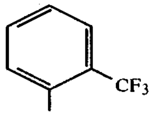 | 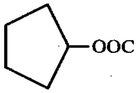 | $CH_3$ | $(CH_2)_4OSO_2$ 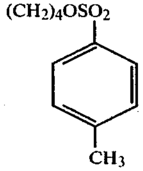 | H |
| 555 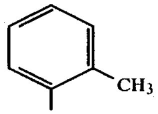 | $C_2H_5OOC$ | $CH_3$ | $CH_2CH_2OH$ | H |
| 556 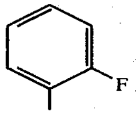 | $(CH_3)_2CHOOC$ | $CH_3$ | $CH_2CH_2N$ 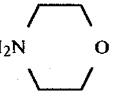 | H |
| 557 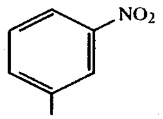 | $CH_3OOC$ | $CH_3$ | $(CH_2)_3NC_2H_5$ | H |
| 558 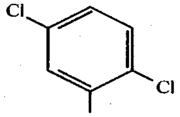 | $(CH_3)_2CHOOC$ | $CH_3$ | H | H |

-continued
| | | | | | |
|---|---|---|---|---|---|
| 559 | 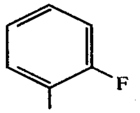 | $(CH_3)_2CHOOC$ | $CH_2Cl$ | H | H |
| 560 | 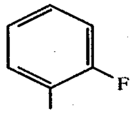 | $(CH_3)_2CHOOC$ | $CH_2N(C_2H_5)_2$ | H | H |
| 561 | 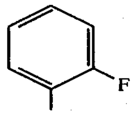 | 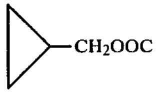 | $CH_3$ | H | H |
| 562 | 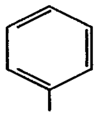 | $(CH_3)_2CHOOC$ | $CH_3$ | H | H |

| | | | | | |
|---|---|---|---|---|---|
| 563 | 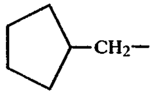 | $CH_3OOC$ | $CH_3$ | H | H |
| 564 | 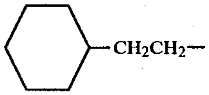 | 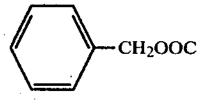 | $CH_3$ | H | H |
| 565 | 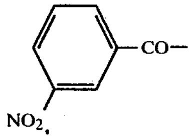 | $CH_3OCH_2CH_2OOC$ | $CH_3$ | H | H |
| 566 | 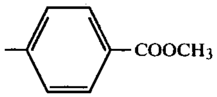 | $CH_3OOC$ | $CH_3$ | H | H |
| 567 | 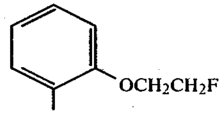 | $(CH_3)_2CHOOC$ | $CH_3$ | H | H |
| 568 | 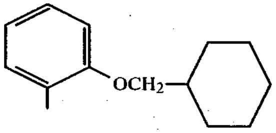 | 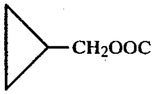 | $CH_3$ | H | H |
| 569 | 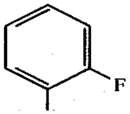 | $(CH_3)_2CHOSC$ | $CH_3$ | H | H |
| 570 | 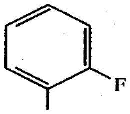 | $(CH_3)_2CHSSC$ | $CH_3$ | H H | |

-continued
| | | | | | |
|---|---|---|---|---|---|
| 571 | 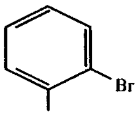 | $H_2NOC$ | $CH_3$ | H | H |
| 572 | 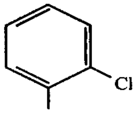 | 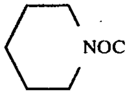 | $CH_3$ | H | H |
| 573 | 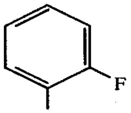 | 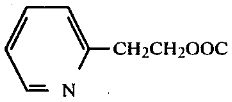 | $CH_3$ | H | H |
| 574 | 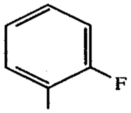 | 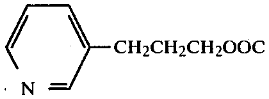 | $CH_3$ | H | H |
| 575 | 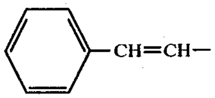 | $(CH_3)_2CHOOC$ | $CH_3$ | H | H |
| 576 | 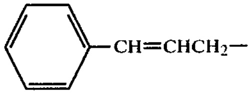 | $(CH_3)_3COOC$ | $CH_3$ | H | H |
| 577 | 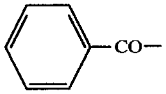 | $C_2H_5OOC$ | $CH_3$ | H | H |
| 578 | 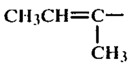 | $(CH_3)_2CHOOC$ | $CH_3$ | H | H |
| 579 | $CH{\equiv}C-CH_2$ | $(CH_3)_3COOC$ | $CH_3$ | H | H |

-continued
| | | | | | |
|---|---|---|---|---|---|
| 580 | 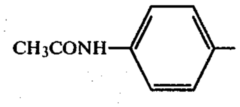 | $C_2H_5OOC$ | $CH_3$ | H | H |
| 581 | 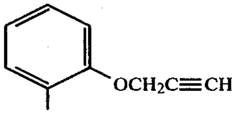 | $(CH_3)_2CHOOC$ | $CH_3$ | H | H |
| 582 | 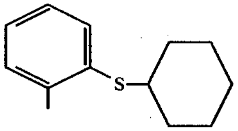 | $C_2H_5OOC$ | $CH_3$ | H | H |
| 583 | 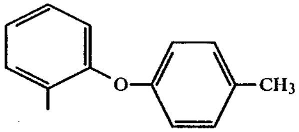 | $CH_3CH_2CH_2OOC$ | $CH_3$ | H | H |
| 584 | 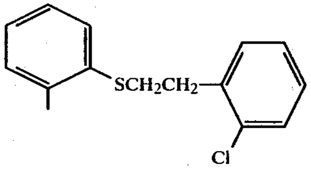 | $CH_3(CH_2)_3OOC$ | $CH_3$ | H | H |
| 585 | 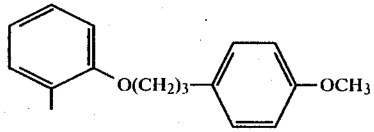 | 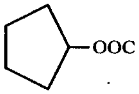 | $CH_3$ | H | H |
| 586 | 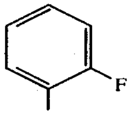 | 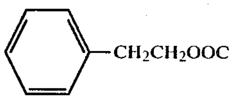 | $CH_3$ | H | H |

-continued
| | | | | | |
|---|---|---|---|---|---|
| 587 | 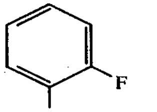 | 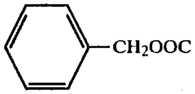 | $CH_3COO(CH_2)_3$ | H | H |
| 588 | 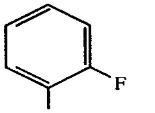 | 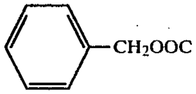 | $HO(CH_2)_3$ | H | H |
| 589 | 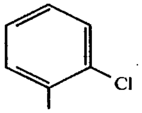 | $(CH_3)_3COOC$ | $CH_3$ | H | H |
| 590 | 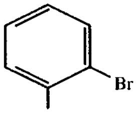 | $(CH_3)_3COOC$ | $CH_3$ | H | H |
| 591 | 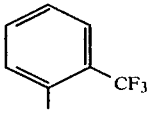 | $ClCH_2CH_2CH_2CH_2OOC$ | $CH_3$ | H | H |
| 592 | 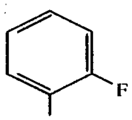 | $(ClCH_2)_2CHOOC$ | $CH_3$ | H | H |
| 593 | 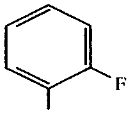 | $(CH_3)_2CHOOC$ | $CH_3COOCH_2$ | H | H |

-continued
| | | | | | |
|---|---|---|---|---|---|
| 594 | 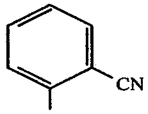 | $(CH_3)_3COOC$ | $CH_3$ | H | H |
| 595 | 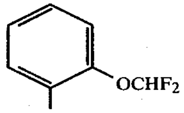 | $(CH_3)_3COOC$ | $CH_3$ | H | H |
| 596 | 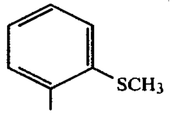 | $(CH_3)_2CHOOC$ | $CH_3$ | H | H |
| 597 | 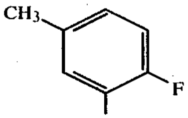 | $(CH_3)_2CHOOC$ | $CH_3$ | H | H |
| 598 | 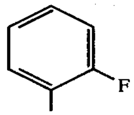 | 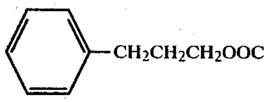 | $CH_3$ | H | H |
| 599 | 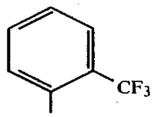 | $(CH_3)_2CHOOC$ | $CH_3$ | $COOC_2H_5$ | H |
| 600 | 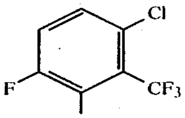 | $C_2H_5OOC$ | $CH_3$ | H | H |

-continued
| | | | | | |
|---|---|---|---|---|---|
| 601 | 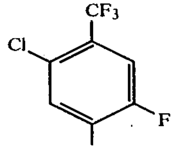 | $(CH_3)_2CHOOC$ | $CH_3$ | H | H |
| 602 | 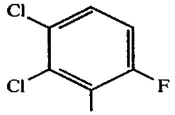 | $C_2H_5OOC$ | $CH_3$ | H | H |
| 603 | 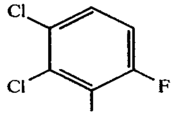 | $(CH_3)_2CHOOC$ | $CH_3$ | H | H |
| 604 | 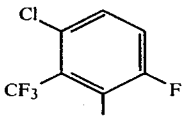 | $(CH_3)_2CHOOC$ | $CH_3$ | H | H |
| 605 | 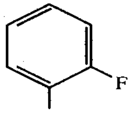 | $C_2H_5OOC$ | $H_2N$ | H | H |
| 606 | 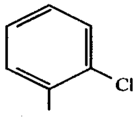 | H | $CH_3$ | H | H |
| 607 | 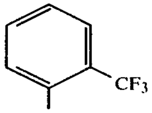 | $CH_3OCH_2CHOOC$ 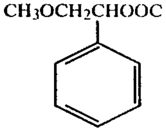 | $CH_3$ | H | H |

-continued
| | | | | | |
|---|---|---|---|---|---|
| 608 | 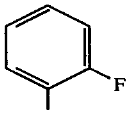 | $(CH_3)_2CHOOC$ | 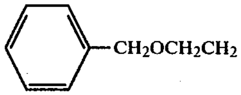 | H | H |
| 609 | 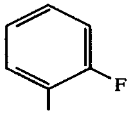 | $(CH_3)_2CHOOC$ | 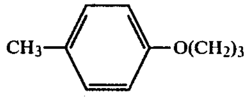 | H | H |
| 610 | 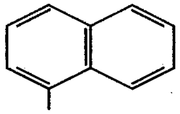 | $(CH_3)_2CHOOC$ | $CH_3$ | H | H |

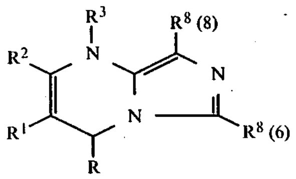
| No. | R | $R^1$ | $R^2$ | $R^3$ | $R^8(6)$ | $R^8(8)$ | M.p. (°C.) |
|---|---|---|---|---|---|---|---|
| 611 | 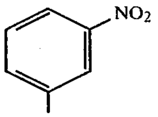 | $C_2H_5OOC$ | $CH_3$ | H | H | $COOC_2H_5$ | 160-162 |
| 612 | 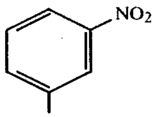 | $C_2H_5OOC$ | $CH_3$ | H | $CH_2N(C_2H_5)_2$ | $COOC_2H_5$ | HCl.3/2 $H_2O$ 193-194(d) |
| 613 | 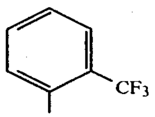 | $C_2H_5OOC$ | $CH_3$ | H | H | $COOC_2H_5$ | 192-193 |
| 614 | 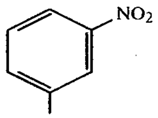 | $C_2H_5OOC$ | $CH_3$ | H | H | COOH | 222(d) |
| 615 | 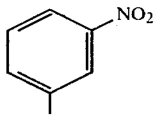 | $C_2H_5OOC$ | $CH_3$ | H | $CH_2N(C_2H_5)_2$ | H | 198-200(d) |
| 616 | $CH_3$ | $C_2H_5OOC$ | $CH_3$ | H | H | H | |

-continued
| | | | | | | |
|---|---|---|---|---|---|---|
| 617 | 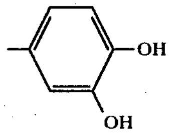 | $CH_3OOC$ | $CH_3$ | H | H | H |
| 618 | 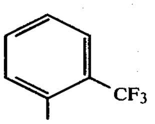 | $C_2H_5OOC$ | $CH_2OCOCH_3$ | H | H | H |
| 619 | 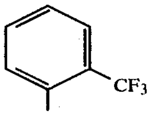 | $C_2H_5OOC$ | $CH_2OH$ | H | H | H |
| 620 | 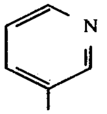 | $CH_3OOC$ | $CH_3$ | H | H | H |
| 621 | 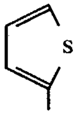 | $C_2H_5OOC$ | $C_3H_7$ | H | H | H |
| 622 | 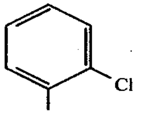 | $C_2H_5OOC$ | $CH_3$ | H | H | H |
| 623 | 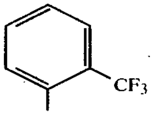 | $C_4H_9OOC$ | $CH_3$ | H | H | H |

-continued
| | | | | | | |
|---|---|---|---|---|---|---|
| 624 | 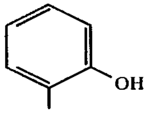 | $CH_3OOC$ | $CH_3$ | H | H | H |
| 625 | 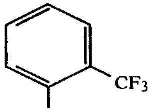 | $C_2H_5OOC$ | $CH_2Cl$ | H | H | H |
| 626 | 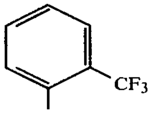 | $C_2H_5OOC$ | $CH_2F$ | H | H | H |
| 627 | 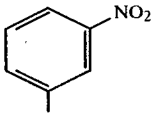 | $CH_3CO$ | $CH_3$ | H | H | H |
| 628 | 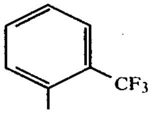 | 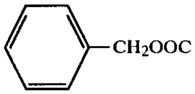 | $CH_3$ | H | H | H |
| 629 | 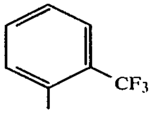 | HOOC | $CH_3$ | H | H | H |
| 630 | 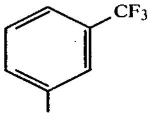 | $C_2H_5OOC$ | $CH_3$ | H | H | H |

-continued
| | | | | | | |
|---|---|---|---|---|---|---|
| 631 | 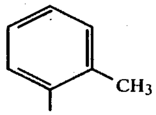 | $C_2H_5OOC$ | $CH_3$ | H | H | H |
| 632 | 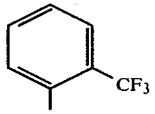 | $C_3H_7OOC$ | $CH_3$ | H | H | H |
| 633 | 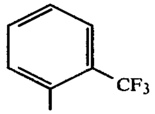 | $(CH_3)_2CHOOC$ | $CH_3$ | H | H | H |
| 634 | 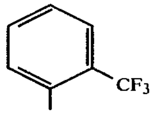 | $(CH_3)_2CHCH_2OOC$ | $CH_3$ | H | H | H |
| 635 | 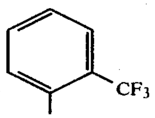 | $(CH_3)_3COOC$ | $CH_3$ | H | H | H |
| 636 | 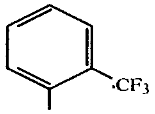 | 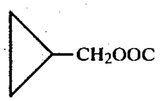 | $CH_3$ | H | H | H |
| 637 | 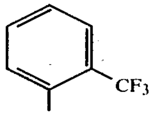 | 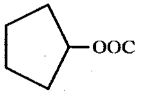 | $CH_3$ | H | H | H |

-continued
| | | | | | | |
|---|---|---|---|---|---|---|
| 638 | 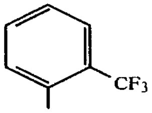 | $CH_3OCH_2CHOOC$ 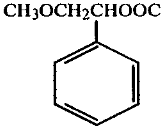 | $CH_3$ | H | H | H |
| 639 | 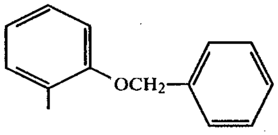 | $C_2H_5OOC$ | $CH_3$ | H | H | H |
| 640 | 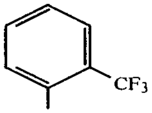 | $O_2N$ | $CH_3$ | H | H | H |
| 641 | 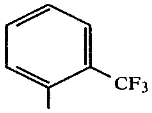 | 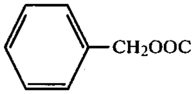 | $CH_3$ | $CH_2OC_2H_5$ | H | H |
| 642 | 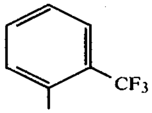 | HOOC | $CH_3$ | $CH_2OC_2H_5$ | H | H |
| 643 | 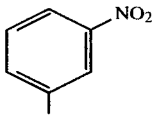 | $C_2H_5OOC$ | $(C_2H_5)_2NCH_2$ | H | H | H |
| 644 | 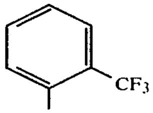 | 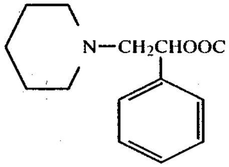 | $CH_3$ | H | H | H |

-continued
| | | | | | | |
|---|---|---|---|---|---|---|
| 645 | 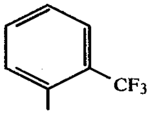 | $C_2H_5OOC$ | $CH_3$ | H | H | H |
| 646 | 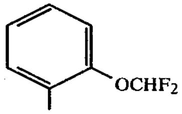 | $C_2H_5OOC$ | $CH_3$ | H | H | H |
| 647 | 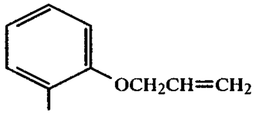 | $C_2H_5OOC$ | $CH_3$ | H | H | H |
| 648 | 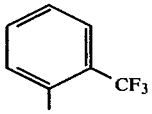 | $FCH_2CH_2OOC$ | $CH_3$ | H | H | H |
| 649 | 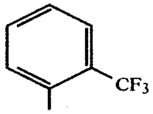 | $CH_3OOC$ | $CH_3$ | H | H | COOH |
| 650 | 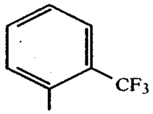 | $CH_3OCH_2CH_2OOC$ | $CH_3$ | H | H | H |
| 651 | 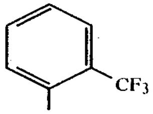 | $O_2N$ | $CH_3$ | H | H | $COOC_2H_5$ |

-continued
| | | | | | | |
|---|---|---|---|---|---|---|
| 652 | 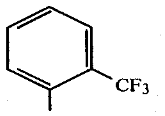 | $ClCH_2CH_2OOC$ | $CH_3$ | H | H | H |
| 653 | 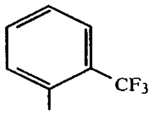 | $CF_3CH_2OOC$ | $CH_3$ | H | H | H |
| 654 | 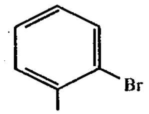 | $C_4H_9OOC$ | $CH_3$ | H | H | H |
| 655 | 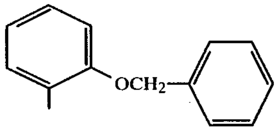 | 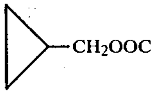 | $CH_3$ | H | H | H |
| 656 | 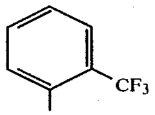 | 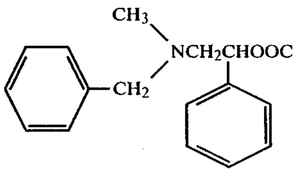 | $CH_3$ | H | H | H |
| 657 | 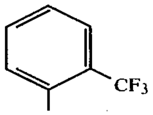 | $CH_3(CH_2)_7OOC$ | $CH_3$ | H | H | H |
| 658 | 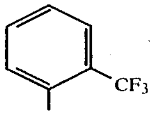 | $CH_3(CH_2)_5OOC$ | $CH_3$ | H | H | H |

-continued
| | | | | | | |
|---|---|---|---|---|---|---|
| 659 | 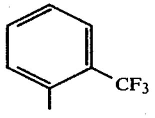 | $CH_2{=}CHCH_2OOC$ | $CH_3$ | H | H | H |
| 660 | 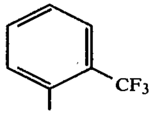 | 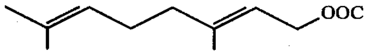 | $CH_3$ | H | H | H |
| 661 | 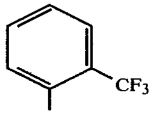 | $CH{\equiv}CCH_2OOC$ | $CH_3$ | H | H | H |
| 662 | 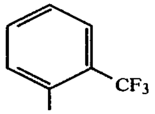 | $CH_3S(CH_2)_2OOC$ | $CH_3$ | H | H | H |
| 663 | 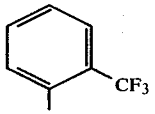 | $CH_3(CH_2)_4OOC$ | $CH_3$ | H | H | H |
| 664 | 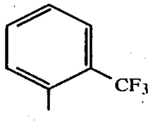 | 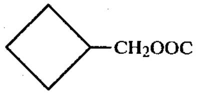 | $CH_3$ | H | H | H |
| 665 | 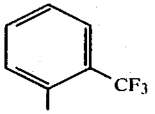 | 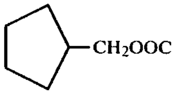 | $CH_3$ | H | H | H |

-continued
| | | | | | | |
|---|---|---|---|---|---|---|
| 666 | 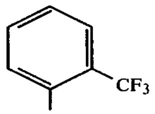 | 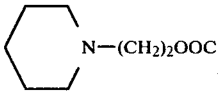 | $CH_3$ | H | H | H |
| 667 | 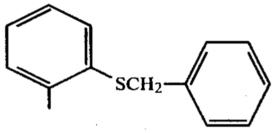 | $C_2H_5OOC$ | $CH_3$ | H | H | H |
| 668 | 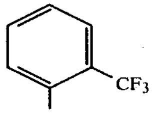 | 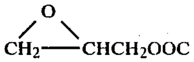 | $CH_3$ | H | H | H |
| 669 | 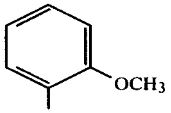 | $C_2H_5OOC$ | $CH_3$ | H | H | H |
| 670 | 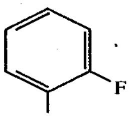 | $C_2H_5OOC$ | $CH_3$ | H | H | H |
| 671 | 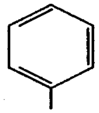 | $CH_3OOC$ | $CH_3$ | H | H | H |
| 672 | 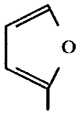 | $C_2H_5OOC$ | $C_3H_7$ | H | H | H |

-continued
| | | | | | | |
|---|---|---|---|---|---|---|
| 673 | 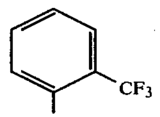 | $CH_3(CH_2)_{21}OOC$ | $CH_3$ | H | H | H |
| 674 | 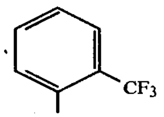 | 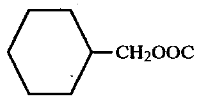 | $CH_3$ | H | H | H |
| 675 | 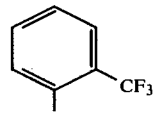 | $(CH_3)_3CCH_2OOC$ | $CH_3$ | H | H | H |
| 676 | 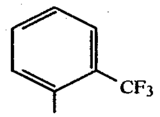 | 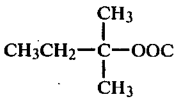 | $CH_3$ | H | H | H |
| 677 | 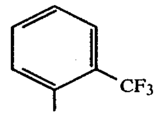 | 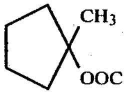 | $CH_3$ | H | H | H |
| 678 | 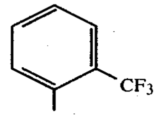 | $C_2H_5OOC$ | $C_3H_7$ | H | H | H |
| 679 | 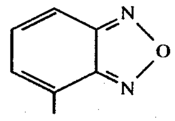 | $C_2H_5OOC$ | $CH_3$ | H | H | H |

-continued
| | | | | | | |
|---|---|---|---|---|---|---|
| 680 | 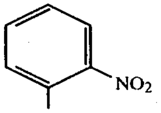 | $C_2H_5OOC$ | $CH_3$ | H | H | H |
| 681 | 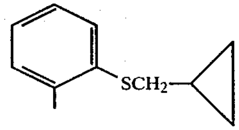 | $C_2H_5OOC$ | $CH_3$ | H | H | H |
| 682 | 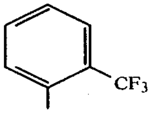 | $CH_3CH_2CHOOC$<br>$CH_3$ | $CH_3$ | H | H | H |
| 683 | 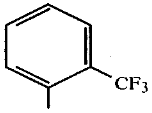 | 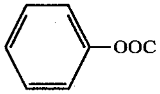 | $CH_3$ | H | H | H |
| 684 | 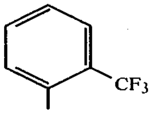 | $CH_3$<br>$C_2H_5OOCCOOC$<br>$CH_3$ | $CH_3$ | H | H | H |
| 685 | 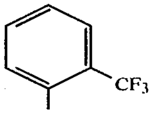 | CN | $CH_3$ | H | H | H |
| 686 | 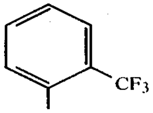 | $C_2H_5OOC$ | $CF_3$ | H | H | H |

-continued
| | | | | | | |
|---|---|---|---|---|---|---|
| 687 | 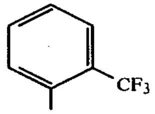 | $CH_3(CH_2)_{15}OOC$ | $CH_3$ | H | H | H |
| 688 | 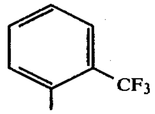 | 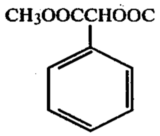 | $CH_3$ | H | H | H |
| 689 | 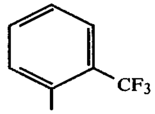 | 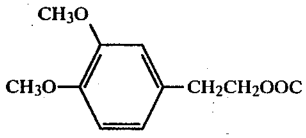 | $CH_3$ | H | H | H |
| 690 | 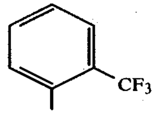 | 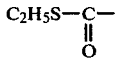 | $CH_3$ | H | H | H |
| 691 | 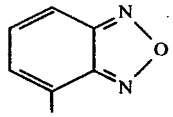 | $O_2N$ | $CH_3$ | H | H | H |
| 692 | 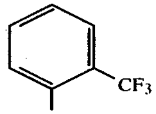 | $C_2H_5OOC$ | Cl | H | H | H |
| 693 | 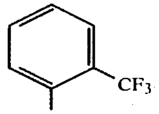 | $C_2H_5OOC$ | $(C_2H_5)_2NCH_2$ | H | H | H |

-continued
| | | | | | | |
|---|---|---|---|---|---|---|
| 694 | 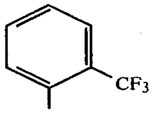 | $C_2H_5OOC$ | $CH_3NHCOOCH_2$ | H | H | H |
| 695 | 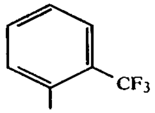 | $C_2H_5OOC$ | $(C_2H_5)_2N$ | H | H | H |
| 696 | 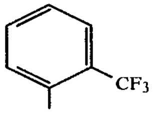 | $C_2H_5OOC$ | $(CH_3)_3C$ | H | H | H |
| 697 | 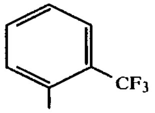 | $C_2H_5OOC$ | $CH_3NHCSOCH_2$ | H | H | H |
| 698 | 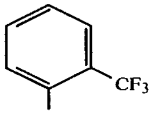 | $C_2H_5OOC$ | $CH_3$ | H | F | H |
| 699 | 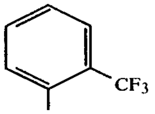 | $C_2H_5OOC$ | $CH_3$ | $CH_3$ | H | H |
| 700 | 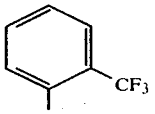 | $C_2H_5OOC$ | $CH_3$ | $CH_2CH_2N$ 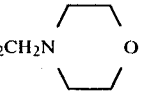 | H | H |

-continued
| | | | | | | |
|---|---|---|---|---|---|---|
| 701 | 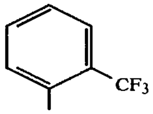 | 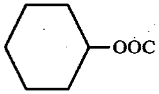 | $CH_3$ | H | H | H |
| 702 | 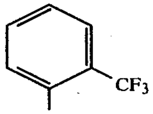 | $C_2H_5OOC$ | $C_2H_5OCH_2$ | H | H | H |
| 703 | 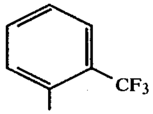 | $C_2H_5OOC$ | $CH_3$ | H | $CH_3$ | H |
| 704 | 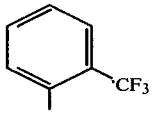 | $C_2H_5OOC$ | $CH_3$ | 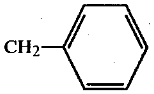 | H | H |
| 705 | 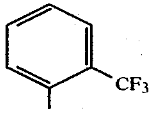 | $C_2H_5OOC$ | 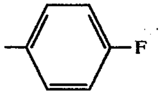 | H | H | H |
| 706 | 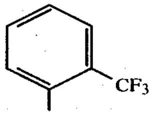 | $H_2NOC$ | $CH_3$ | H | H | H |
| 707 | 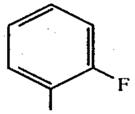 | 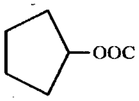 | $CH_3$ | H | H | H |

-continued
| | | | | | | |
|---|---|---|---|---|---|---|
| 708 | 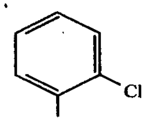 | $(CH_3)_2CHOOC$ | $CH_3$ | H | H | H |
| 709 | 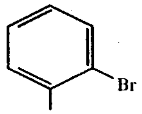 | $(CH_3)_2CHOOC$ | $CH_3$ | H | H | H |
| 710 | 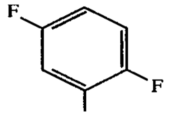 | $(CH_3)_2CHOOC$ | $CH_3$ | H | H | H |
| 711 | 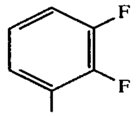 | $(CH_3)_2CHOOC$ | $CH_3$ | H | H | H |
| 712 | 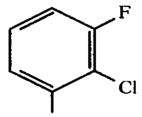 | $(CH_3)_2CHOOC$ | $CH_3$ | H | H | H |
| 713 | 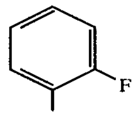 | $CH_3OCH_2CHOOC$ 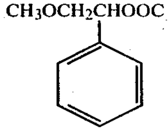 | $CH_3$ | H | H | H |
| 714 | 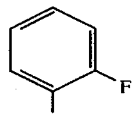 | $(CH_3)_2CHOOC$ | $CH_3$ | H | H | H |

-continued
| | | | | | | |
|---|---|---|---|---|---|---|
| 715 | 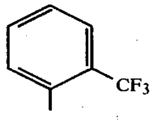 | $(C_2H_5)_2CHOOC$ | $CH_3$ | H | H | H |
| 716 | 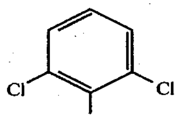 | $C_2H_5OOC$ | $CH_3$ | H | H | H |
| 717 | 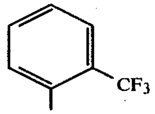 | $(CH_3)_2CHOOC$ | $CH_3$ | $CH_3$ | H | H |
| 718 | 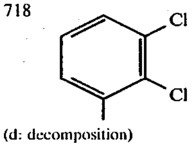 | $C_2H_5OOC$ | $CH_3$ | H | H | H |
(d: decomposition)

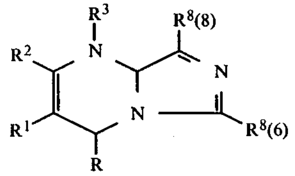
| No. | R | $R^1$ | $R^2$ | $R^3$ | $R^8(6)$ | $R^8(8)$ |
|---|---|---|---|---|---|---|
| 719 | 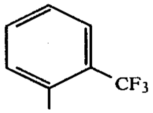 | $H_2NSC$ | $CH_3$ | H | H | H |
| 720 | 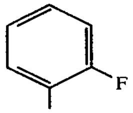 | $(CH_3)_2CHOOC$ | $CH_3$ | H | H | H |
| 721 | 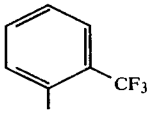 | $(CH_3)_2CHS\overset{\overset{\Large O}{\|}}{C}$ | $CH_3$ | H | H | H |
| 722 | 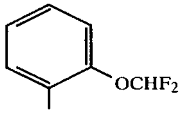 | $CH_3OOC$ | $CH_3$ | H | H | H |
| 723 | 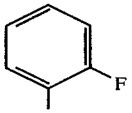 | $C_3H_7OOC$ | $CH_3$ | H | H | H |
| 724 | 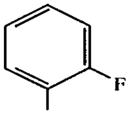 | $(CH_3)_3COOC$ | $CH_3$ | H | H | H |

-continued
| | | | | | | |
|---|---|---|---|---|---|---|
| 725 | 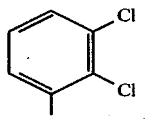 | $(CH_3)_3COOC$ | $CH_3$ | H | H | H |
| 726 | 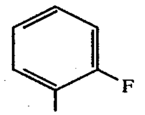 | $(CH_3)_2CHCH_2OOC$ | $CH_3$ | H | H | H |
| 727 | 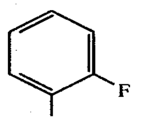 | $C_4H_9OOC$ | $CH_3$ | H | H | H |
| 728 | 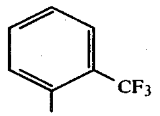 | $(CH_3)_2NCH_2CH_2OOC$ | $CH_3$ | H | H | H |
| 729 | 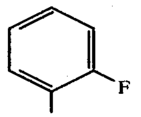 | $(CH_3)_2CHOOC$ | $C_2H_5$ | H | H | H |
| 730 | 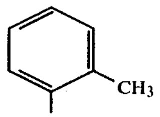 | $(CH_3)_2CHOOC$ | $CH_3$ | H | H | H |
| 731 | 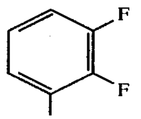 | $C_2H_5OOC$ | $CH_3$ | H | H | H |

-continued
| | | | | | | |
|---|---|---|---|---|---|---|
| 732 | 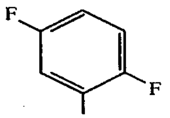 | $C_2H_5OOC$ | $CH_3$ | H | H | H |
| 733 | 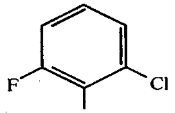 | $C_2H_5OOC$ | $CH_3$ | H | H | H |
| 734 | 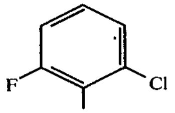 | $(CH_3)_2CHOOC$ | $CH_3$ | H | H | H |
| 735 | 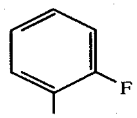 | $(CH_3)_2CHOOC$ | $CH(CH_3)_2$ | H | H | H |
| 736 | 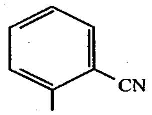 | $(CH_3)_2CHOOC$ | $CH_3$ | H | H | H |
| 737 | 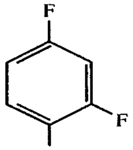 | $C_2H_5OOC$ | $CH_3$ | H | H | H |
| 738 | 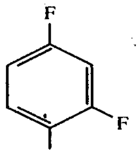 | $(CH_3)_2CHOOC$ | $CH_3$ | H | H | H |

-continued
| | | | | | | |
|---|---|---|---|---|---|---|
| 739 | 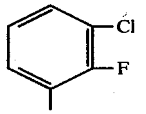 | $C_2H_5OOC$ | $CH_3$ | H | H | H |
| 740 | 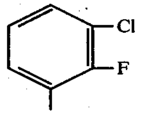 | $(CH_3)_2CHOOC$ | $CH_3$ | H | H | H |
| 741 | 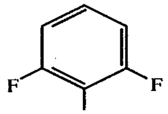 | $C_2H_5OOC$ | $CH_3$ | H | H | H |
| 742 | 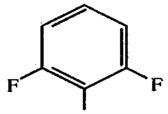 | $(CH_3)_2CHOOC$ | $CH_3$ | H | H | H |
| 743 | 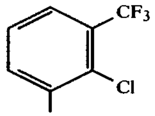 | $C_2H_5OOC$ | $CH_3$ | H | H | H |
| 744 | 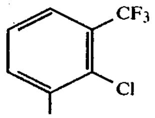 | $(CH_3)_2CHOOC$ | $CH_3$ | H | H | H |
| 745 | 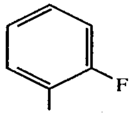 | $(CH_3)_2CHOOC$ | $CH_2OH$ | H | H | H |

-continued
| | | | | | | |
|---|---|---|---|---|---|---|
| 746 | 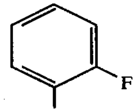 | $(CH_3)_2CHOOC$ | $C_4H_9$ | H | H | H |
| 747 | 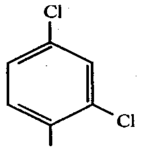 | $(CH_3)_2CHOOC$ | $CH_3$ | H | H | H |
| 748 | 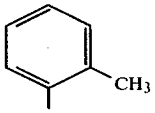 | $(CH_3)_2CHOOC$ | $CH_3$ | H | H | H |
| 749 | 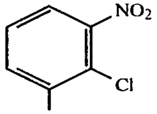 | $C_2H_5OOC$ | $CH_3$ | H | H | H |
| 750 | 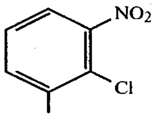 | $(CH_3)_2CHOOC$ | $CH_3$ | H | H | H |
| 751 | 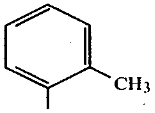 | $(CH_3)_2CHCH_2OOC$ | $CH_3$ | H | H | H |
| 752 | 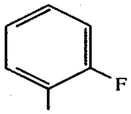 | $(CH_3)_2CHOOC$ | $CH_2F$ | H | H | H |

-continued
| | | | | | | |
|---|---|---|---|---|---|---|
| 753 | 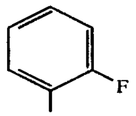 | $(CH_3)_2CHOOC$ | $CH_2CH_2OH$ | H | H | H |
| 754 | 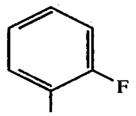 | $(CH_3)_2CHOOC$ | $(CH_2)_3OH$ | H | H | H |
| 755 | 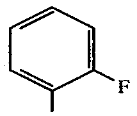 | $C_2H_5OOC$ | 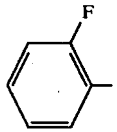 | H | H | H |
| 756 | 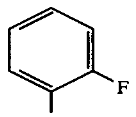 | CN | $CH_3$ | H | H | H |
| 757 | 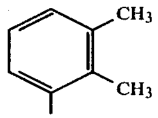 | $(CH_3)_2CHOOC$ | $CH_3$ | H | H | H |
| 758 | 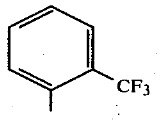 | $(CH_3)_2CHOOC$ | $C_4H_9$ | H | H | H |
| 759 | 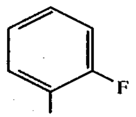 | $(CH_3)_2CHOOC$ | $CH_2OCOCH_3$ | H | H | H |

-continued
| | | | | | | |
|---|---|---|---|---|---|---|
| 760 | 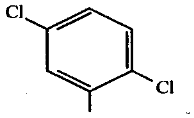 | $(CH_3)_2CHOOC$ | $CH_3$ | H | H | H |
| 761 | 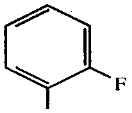 | $(CH_3)_2CHOOC$ | $CH_2Cl$ | H | H | H |
| 762 | 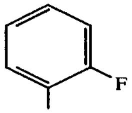 | $(CH_3)_2CHOOC$ | $CH_2N(C_2H_5)_2$ | H | H | H |
| 763 | 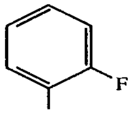 | 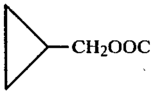 | $CH_3$ | H | H | H |
| 764 | 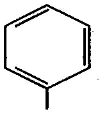 | $(CH_3)_2CHOOC$ | $CH_3$ | H | H | H |
| 765 | 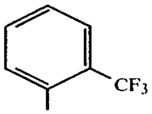 | $(CH_3)_2CHOOC$ | $CH_3$ | $COOC_2H_5$ | H | H |
| 766 | 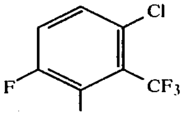 | $C_2H_5OOC$ | $CH_3$ | H | H | H |

-continued
| | | | | | | |
|---|---|---|---|---|---|---|
| 767 | 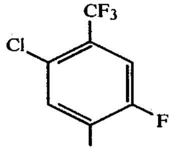 | $(CH_3)_2CHOOC$ | $CH_3$ | H | H | H |
| 768 | 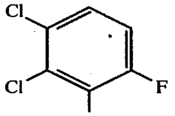 | $C_2H_5OOC$ | $CH_3$ | H | H | H |
| 769 | 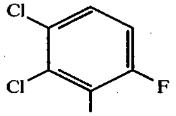 | $(CH_3)_2CHOOC$ | $CH_3$ | H | H | H |
| 770 | 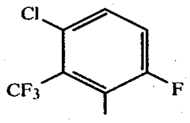 | $(CH_3)_2CHOOC$ | $CH_3$ | H | H | H |
| 771 | 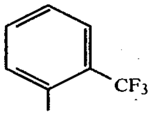 | $(ClCH_2)_2CHOOC$ | $CH_3$ | H | H | H |
| 772 | 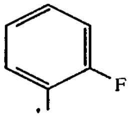 | $ClCH_2CH_2OOC$ | $CH_3$ | H | H | H |
| 773 | 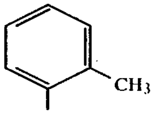 | 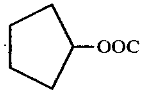 | $CH_3$ | H | H | H |

-continued
| | | | | | | |
|---|---|---|---|---|---|---|
| 774 | 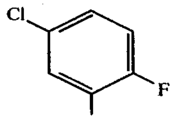 | $(CH_3)_2CHOOC$ | $CH_3$ | H | H | H |
| 775 | 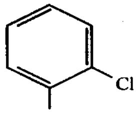 | 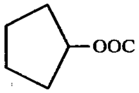 | $CH_3$ | H | H | H |
| 776 | 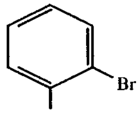 | 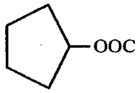 | $CH_3$ | H | H | H |
| 777 | 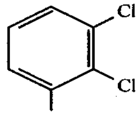 | $(CH_3)_3COOC$ | $CH_3$ | H | H | H |
| 778 | 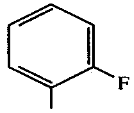 | $(CH_3)_2CHOOC$ | $Cl(CH_2)_3$ | H | H | H |
| 779 | 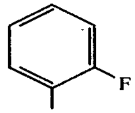 | $(CH_3)_2CHOOC$ | $CH_3COO(CH_2)_3$ | H | H | H |
| 780 | 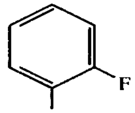 | 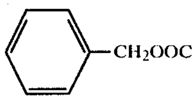 | $CH_3COO(CH_2)_3$ | H | H | H |

-continued
| | | | | | | |
|---|---|---|---|---|---|---|
| 781 | 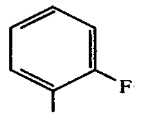 | 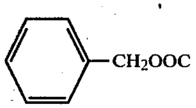 | $HO(CH_2)_3$ | H | H | H |
| 782 | 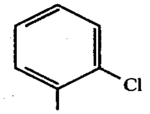 | $(CH_3)_3COOC$ | $CH_3$ | H | H | H |
| 783 | 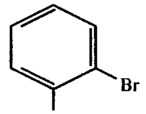 | $(CH_3)_3COOC$ | $CH_3$ | H | H | H |
| 784 | 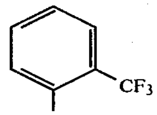 | $ClCH_2CH_2CH_2CH_2OOC$ | $CH_3$ | H | H | H |
| 785 | 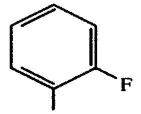 | $(ClCH_2)_2CHOOC$ | $CH_3$ | H | H | H |
| 786 | 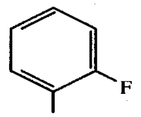 | $(CH_3)_2CHOOC$ | $CH_3COOCH_2$ | H | H | H |
| 787 | 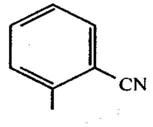 | $(CH_3)_3COOC$ | $CH_3$ | H | H | H |

-continued
| | | | | | |
|---|---|---|---|---|---|
| 788 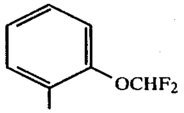 | $(CH_3)_3COOC$ | $CH_3$ | H | H | H |
| 789 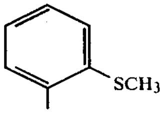 | $(CH_3)_2CHOOC$ | $CH_3$ | H | H | H |
| 790 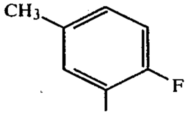 | $(CH_3)_2CHOOC$ | $CH_3$ | H | H | H |
| 791 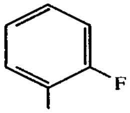 | 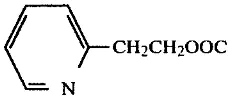 | $CH_3$ | H | H | H |
| 792 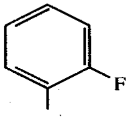 | 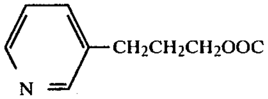 | $CH_3$ | H | H | H |
| 793 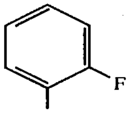 | 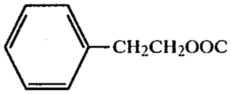 | $CH_3$ | H | H | H |
| 794 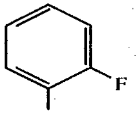 | 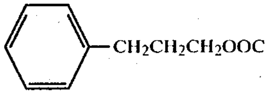 | $CH_3$ | H | H | H |

-continued
| | | | | | | |
|---|---|---|---|---|---|---|
| 795 | 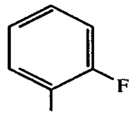 | $C_2H_5OOC$ | $H_2N$ | H | H | H |
| 796 | 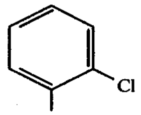 | H | $CH_3$ | H | H | H |
| 797 | 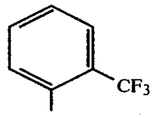 | $CH_3OCH_2CHOOC$ 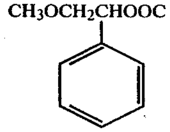 | $CH_3$ | H | H | H |
| 798 | 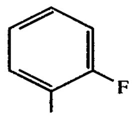 | $(CH_3)_2CHOOC$ | 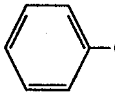 $-CH_2OCH_2CH_2$ | H | H | H |
| 799 | 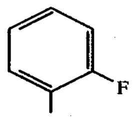 | $(CH_3)_2CHOOC$ | $CH_3-$ 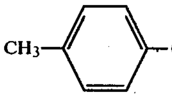 $-O(CH_2)_3$ | H | H | H |
| 800 | 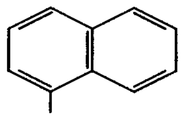 | $(CH_3)_2CHOOC$ | $CH_3$ | H | H | H |
| 801 | 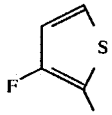 | $(CH_3)_2CHOOC$ | $CH_3$ | H | H | H |

-continued
| | | | | | | |
|---|---|---|---|---|---|---|
| 802 | 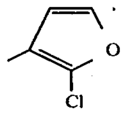 | $C_2H_5OOC$ | $CH_3$ | H | H | H |
| 803 | 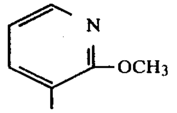 | $(CH_3)_2CHOOC$ | $CH_3$ | H | H | H |
| 804 | 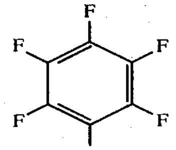 | $(CH_3)_2CHOOC$ | $CH_3$ | H | H | H |
| 805 | 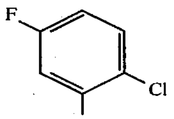 | $(CH_3)_3COOC$ | $CH_3$ | H | H | H |
| 806 | 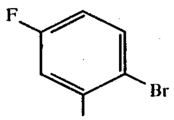 | $CH_3CH_2CH_2OOC$ | $CH_3$ | H | H | H |
| 807 | 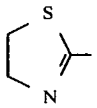 | $CH_3OOC$ | $CH_3$ | H | H | H |
| 808 | 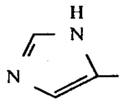 | 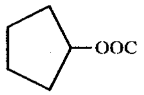 | $CH_3$ | H | H | H |

-continued
| | | | | | | |
|---|---|---|---|---|---|---|
| 809 | 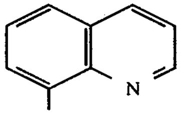 | $(CH_3)_2CHOOC$ | $CH_3$ | H | H | H |
| 810 | 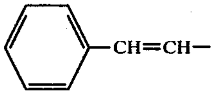 | $(CH_3)_2CHOOC$ | $CH_3$ | H | H | H |
| 811 | 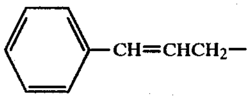 | $(CH_3)_3COOC$ | $CH_3$ | H | H | H |
| 812 | 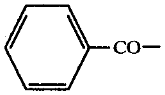 | $C_2H_5OOC$ | $CH_3$ | H | H | H |
| 813 | $CH_3CH{=}C-$<br>$CH_3$ | $(CH_3)_2CHOOC$ | $CH_3$ | H | H | H |
| 814 | $CH{\equiv}C-CH_2-$ | $(CH_3)_3COOC$ | $CH_3$ | H | H | H |
| 815 | 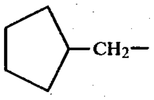 | $CH_3OOC$ | $CH_3$ | H | H | H |
| 816 | 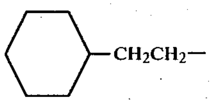 | 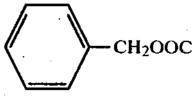 | $CH_3$ | H | H | H |
| 817 | 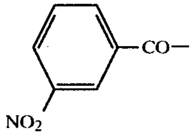 | $CH_3OCH_2CH_2OOC$ | $CH_3$ | H | H | H |

-continued
| | | | | | | |
|---|---|---|---|---|---|---|
| 818 | 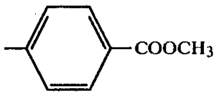 | $CH_3OOC$ | $CH_3$ | H | H | H |
| 819 | 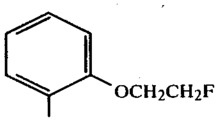 | $(CH_3)_2CHOOC$ | $CH_3$ | H | H | H |
| 820 | 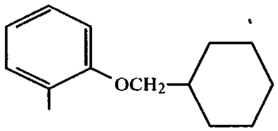 | 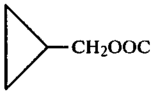 | $CH_3$ | H | H | H |
| 821 | 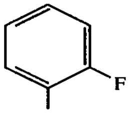 | $(CH_3)_2CHOSC$ | $CH_3$ | H | H | H |
| 822 | 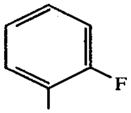 | $(CH_3)_2CHSSC$ | $CH_3$ | H | H | H |
| 823 | 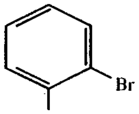 | $H_2NOC$ | $CH_3$ | H | H | H |
| 824 | 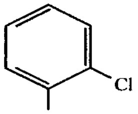 | 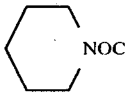 | $CH_3$ | H | H | H |

-continued
| | | | | | | |
|---|---|---|---|---|---|---|
| 825 | 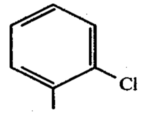 | $(CH_3)_2CHOOC$ | $CH_3$ | $CH_2CH_2Cl$ | H | H |
| 826 | 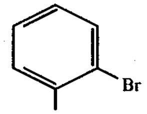 | $(CH_3)_3COOC$ | $CH_3$ | $(CH_2)_3OSO_2CH_3$ | H | H |

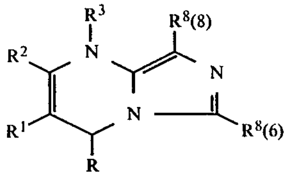
| No. | R | $R^1$ | $R^2$ | $R^3$ | $R^8(6)$ | $R^8(8)$ |
|---|---|---|---|---|---|---|
| 827 | 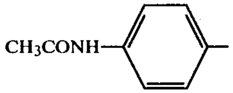 | $C_2H_5OOC$ | $CH_3$ | H | H | H |
| 828 | 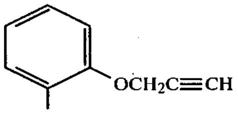 | $(CH_3)_2CHOOC$ | $CH_3$ | H | H | H |
| 829 | 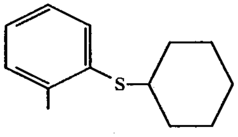 | $C_2H_5OOC$ | $CH_3$ | H | H | H |
| 830 | 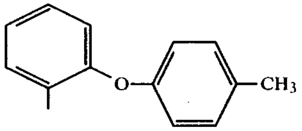 | $CH_3CH_2CH_2OOC$ | $CH_3$ | H | H | H |
| 831 | 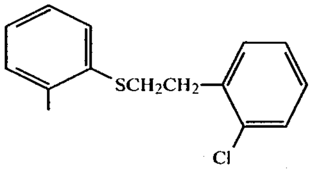 | $CH_3(CH_2)_3OOC$ | $CH_3$ | H | H | H |

-continued
| | | | | | | |
|---|---|---|---|---|---|---|
| 832 | 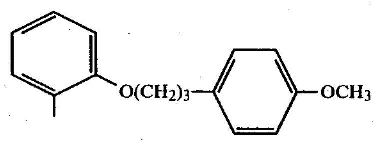 | 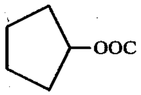 | $CH_3$ | H | H | H |
| 833 | 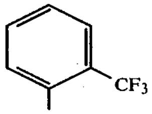 | 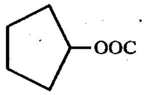 | $CH_3$ | 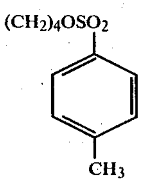 | H | H |
| 834 | 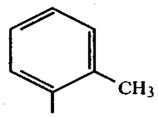 | $C_2H_5OOC$ | $CH_3$ | $CH_2CH_2OH$ | H | H |
| 835 | 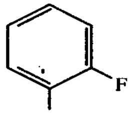 | $(CH_3)_2CHOOC$ | $CH_3$ | 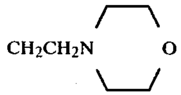 | H | H |
| 836 | 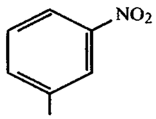 | $CH_3OOC$ | $CH_3$ | $(CH_2)_3NC_2H_5$ | H | H |
| 837 | 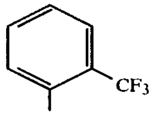 | $(CH_3)_2CHNHOC$ | $CH_3$ | H | H | H |
| 838 | 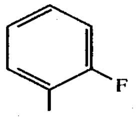 | $(C_2H_5)_2NOC$ | $CH_3$ | H | H | H |

-continued
| | | | | | | |
|---|---|---|---|---|---|---|
| 839 | 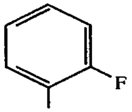 | $H_2NSC$ | $CH_3$ | H | H | H |
| 840 | 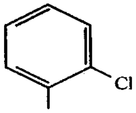 | 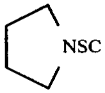 | $CH_3$ | H | H | H |
| 841 | 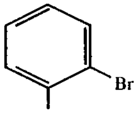 | $(CH_3)_3CNHSC$ | $CH_3$ | H | H | H |
| 842 | 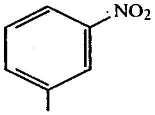 | 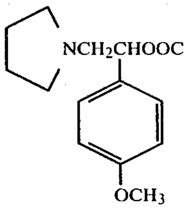 | $CH_3$ | H | H | H |
| 843 | 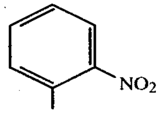 | $(CH_3)_2CHOCH_2CHOOC$ 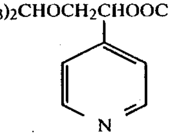 | $CH_3$ | H | H | H |
| 844 | 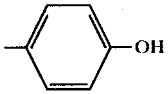 | $CH_3OOCCH_2CHOOC$ 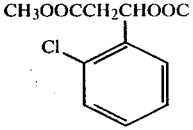 | $CH_3$ | H | H | H |

-continued
| | | | | | |
|---|---|---|---|---|---|
| 845 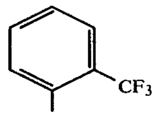 | 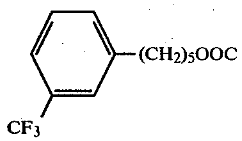 | $CH_3$ | H | H | H |
| 846 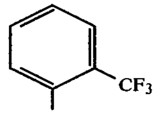 | $C_2H_5OOC$ | 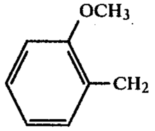 | H | H | H |
| 847 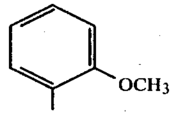 | $CH_3OOC$ | 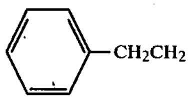 | H | H | H |
| 848 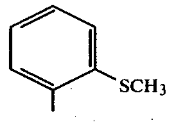 | $(CH_3)_2CHOOC$ | 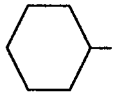 | H | H | H |
| 849 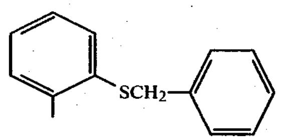 | $CH_3(CH_2)_2OOC$ | 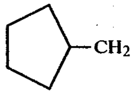 | H | H | H |
| 850 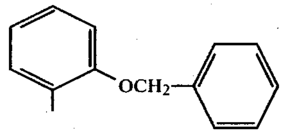 | $CH_3(CH_2)_3OOC$ | $H_2NCH_2CH_2$ | H | H | H |
| 851 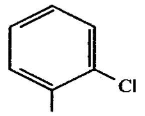 | $CH_3(CH_2)_3OOC$ | $CH_3CONHCH_2CH_2$ | H | H | H |

-continued
| | | | | | | |
|---|---|---|---|---|---|---|
| 852 | 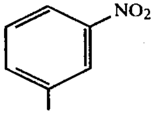 | $(CH_3)_2CHCH_2OOC$ | $HOCH_2CH_2OCH_2$ | H | H | H |
| 853 | 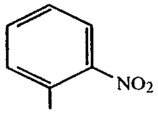 | $C_2H_5OOC$ | $H_2N(CH_2)_2OCH_2$ | H | H | H |
| 854 | 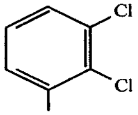 | $CH_3OOC$ | 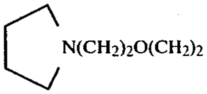 | H | H | H |
| 855 | 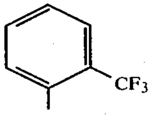 | $(CH_3)_2CHOOC$ | $CH_3$ | $C_3H_7$ | H | H |
| 856 | 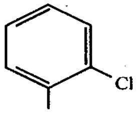 | $(CH_3)_3COOC$ | $CH_3$ | 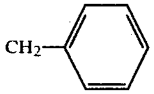 | H | H |
| 857 | 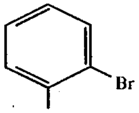 | $C_3H_7OOC$ | $CH_3$ | 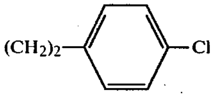 | H | H |
| 858 | 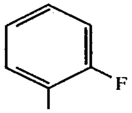 | 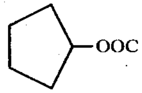 | $CH_3$ | 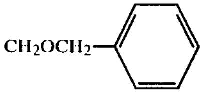 | H | H |

-continued
| | | | | | | |
|---|---|---|---|---|---|---|
| 859 | 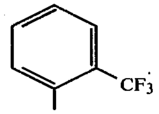 | $CH_3(CH_2)_3OOC$ | $CH_3$ | $COCH_3$ | H | H |
| 860 | 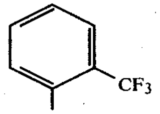 | $C_2H_5OOC$ | $CH_3$ | H | H | Cl |
| 861 | 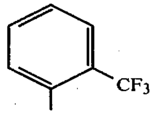 | 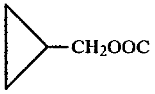 | $CH_3$ | H | H | CN |
| 862 | 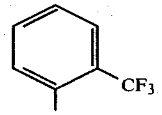 | $C_2H_5OOC$ | $CH_3$ | H | 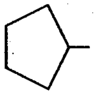 | H |
| 863 | 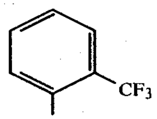 | $C_2H_5OOC$ | $CH_3$ | H | H | $CH_2N(C_2H_5)_2$ |
| 864 | 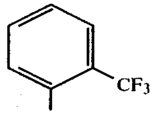 | $CH_3OOC$ | $CH_3$ | H | H | Br |
| 865 | 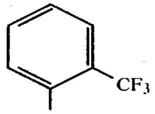 | $CH_3OOC$ | $CH_3$ | H | H | $NO_2$ |

-continued
| | | | | | | |
|---|---|---|---|---|---|---|
| 866 | 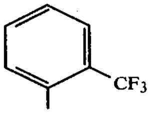 | $CH_3OOC$ | $CH_3$ | H | H | CN |
| 867 | 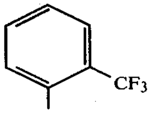 | $CH_3OOC$ | $CH_3$ | H | H | $CONH_2$ |
| 868 | 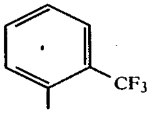 | $C_2H_5OOC$ | $CH_3$ | H | H | 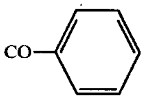 |
| 869 | 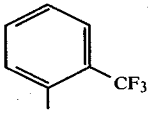 | 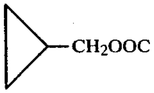 | $CH_3$ | H | H | $NO_2$ |
| 870 | 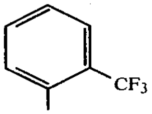 | $C_2H_5OOC$ | $CH_3$ | H | H | Br |
| 871 | 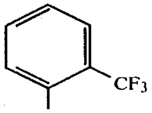 | $C_2H_5OOC$ | $CH_3$ | H | H | CN |
| 872 | 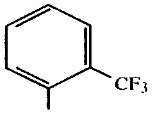 | 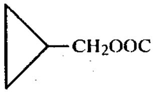 | $CH_3$ | H | H | $NH_2$ |

-continued
| | | | | | | |
|---|---|---|---|---|---|---|
| 873 | 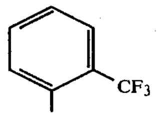 | $C_2H_5OOC$ | $CH_3$ | H | H | $NO_2$ |
| 874 | 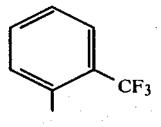 | $C_2H_5OOC$ | $CH_3$ | H | H | $CONH_2$ |
| 875 | 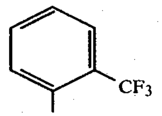 | 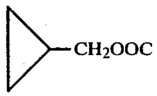 | $CH_3$ | H | H | $NHCOCH_3$ |
| 876 | 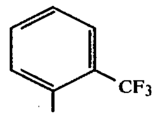 | $C_2H_5OOC$ | $CH_3$ | H | H | F |
| 877 | 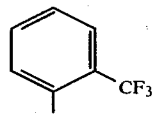 | $C_2H_5OOC$ | $CH_3$ | H | H | $CH_2OH$ |
| 878 | 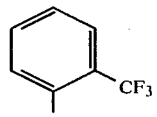 | $C_2H_5OOC$ | $CH_3$ | H | H | $C_3H_7$ |
| 879 | 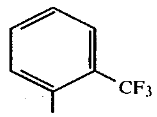 | $C_2H_5OOC$ | $CH_3$ | H | H | $CH_3$ |

-continued
| | | | | | | |
|---|---|---|---|---|---|---|
| 880 | 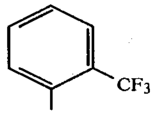 | $C_2H_5OOC$ | $CH_3$ | H | H | $NHCOCH_3$ |
| 881 | 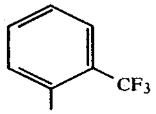 | $C_2H_5OOC$ | $CH_3$ | H | $CH_3$ | $CH_3$ |
| 882 | 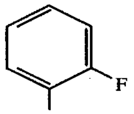 | $(CH_3)_2CHOOC$ | $CH_3$ | H | H | CN |
| 883 | 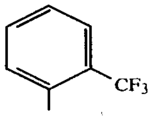 | $(CH_3)_2CHOOC$ | $CH_3$ | H | H | Cl |
| 884 | 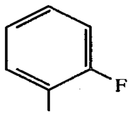 | $(CH_3)_2CHOOC$ | $CH_3$ | H | H | $CH_3$ |
| 885 | 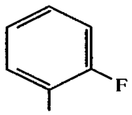 | $(CH_3)_2CHOOC$ | $CH_3$ | H | H | $CH(CH_3)_2$ |
| 886 | 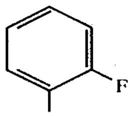 | $(CH_3)_2CHOOC$ | $CH_3$ | H | F | H |

-continued
| | | | | | | |
|---|---|---|---|---|---|---|
| 887 | 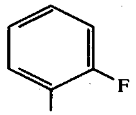 | $(CH_3)_2CHOOC$ | $CH_3$ | H | H | F |
| 888 | 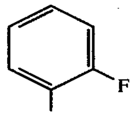 | $(CH_3)_2CHOOC$ | $CH_3$ | H | H | $NO_2$ |
| 889 | 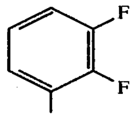 | $(CH_3)_2CHOOC$ | $CH_3$ | H | H | CN |
| 890 | 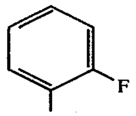 | $(CH_3)_2CHOOC$ | $CH_3$ | H | H | $CH_2OH$ |
| 891 | 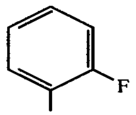 | $(CH_3)_2CHOOC$ | $CH_3$ | H | H | $CH_2OCOCH_3$ |
| 892 | 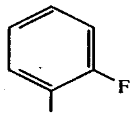 | $(CH_3)_2CHOOC$ | $CH_3$ | H | H | COOH |
| 893 | 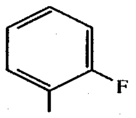 | $(CH_3)_2CHOOC$ | $CH_3$ | H | H | $COCH_3$ |

-continued
| | | | | | | |
|---|---|---|---|---|---|---|
| 894 | 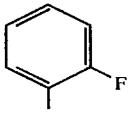 | $(CH_3)_2CHOOC$ | $CH_3$ | H | H | 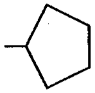 |
| 895 | 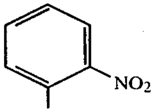 | $(CH_3)_2CHOOC$ | $CH_3$ | H | H | CN |
| 896 | 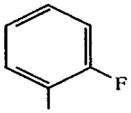 | $(CH_3)_2CHOOC$ | $CH_3$ | H | H | $CH_2F$ |
| 897 | 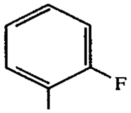 | $(CH_3)_3COOC$ | $CH_3$ | H | H | $-CH_2CF_3$ |
| 898 | 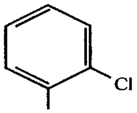 | $(CH_3)_2CHOOC$ | $CH_3$ | H | $CHF_2$ | H |
| 899 | 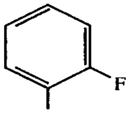 | 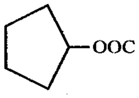 | $CH_3$ | H | H | $-CH_2CH=CH_2$ |
| 900 | 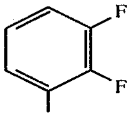 | $(CH_3)_2CHOOC$ | $CH_3$ | H | H | $-C\equiv CH$ |

-continued
| | | | | | | |
|---|---|---|---|---|---|---|
| 901 | 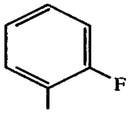 | $C_2H_5OOC$ | $CH_3$ | H | H | $-CH_2OCH_2CH_3$ |
| 902 | 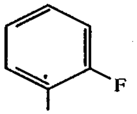 | $(CH_3)_2CHOOC$ | $CH_3$ | H | H | 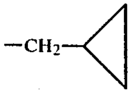 |
| 903 | 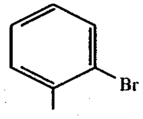 | $CH_3OOC$ | $CH_3$ | H | H | $-(CH_2)_3CN$ |
| 904 | 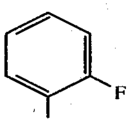 | 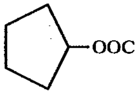 | $CH_3$ | H | H | $-CH_2CH_2NO_2$ |
| 905 | 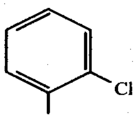 | $CH_3(CH_2)_3OOC$ | $CH_3$ | H | H | $CH_2O\overset{O}{\overset{\|}{C}}NH_2$ |
| 906 | 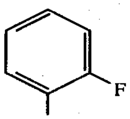 | $(CH_3)_2CHOOC$ | $CH_3$ | H | H | $CH_2O\overset{O}{\overset{\|}{C}}N(CH_3)_2$ |
| 907 | 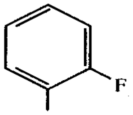 | $(CH_3)_2COOC$ | $CH_3$ | H | H | $-CH_2O\overset{S}{\overset{\|}{C}}NH_2$ |

-continued
| | | | | | | |
|---|---|---|---|---|---|---|
| 908 | 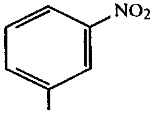 | $(CH_3)_2CHOOC$ | $CH_3$ | H | H | CN |
| 909 | 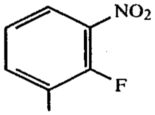 | $(CH_3)_2CHCH_2OOC$ | $CH_3$ | H | H | CN |
| 910 | 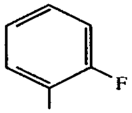 | $(CH_3)_2CHOOC$ | $CH_3$ | H | H | 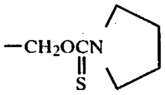 |
| 911 | 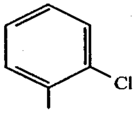 | $C_2H_5OOC$ | $CH_3$ | H | H | $-CON(C_2H_5)_2$ |
| 912 | 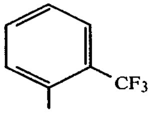 | $(CH_3)_2CHOOC$ | $CH_3$ | H | $CH_2CH{=}CH_2$ | H |
| 913 | 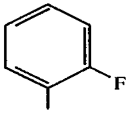 | $(CH_3)_3COOC$ | $CH_3$ | H | H | Br |
| 914 | 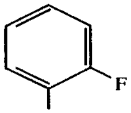 | $(CH_3)_3COOC$ | $CH_3$ | H | $CH_3$ | H |
| 915 | 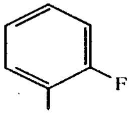 | $(CH_3)_3COOC$ | $CH_3$ | H | H | Cl |

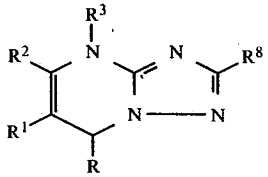
| No. | R | $R^1$ | $R^2$ | $R^3$ | $R^8$ | M.p. (°C.) |
|---|---|---|---|---|---|---|
| 916 | 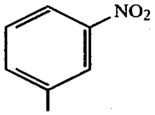 | $C_2H_5OOC$ | $CH_3$ | H | H | 222–224 |
| 917 | 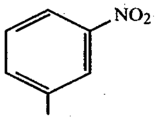 | $C_2H_5OOC$ | $CH_2OCOCH_3$ | H | H | 169–171 |
| 918 | 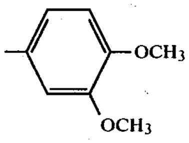 | $CH_3OOC$ | $CH_3$ | H | H | 211–213 |
| 919 | 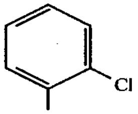 | $CH_3OOC$ | $CH_3$ | H | H | 268–271(d) |
| 920 | 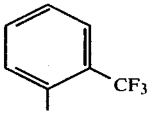 | $CH_3OOC$ | $CH_3$ | H | H | 242 |
| 921 | 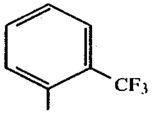 | $CH_3OOC$ | $CH_2Br$ | H | H | 160–170 |

-continued
| | | | | | | |
|---|---|---|---|---|---|---|
| 922 | 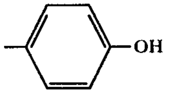 | $CH_3OOC$ | $CH_2Cl$ | H | H | 290(d) |
| 923 | 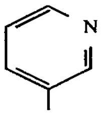 | $C_2H_5OOC$ | $CH_3$ | H | H | 221-223 |
| 924 | 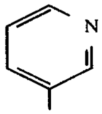 | H | $C(CH_3)_3$ | H | H | 179-181 |
| 925 | 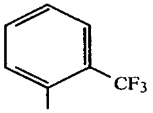 | $C_4H_9OOC$ | $CH_3$ | H | H | 193-195 |
| 926 | 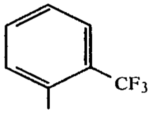 | $C_2H_5OOC$ | $CH_3$ | H | H | 250-252 |
| 927 | 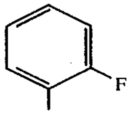 | $(CH_3)_2CHOOC$ | $CH_3$ | H | H | 188-189 |
| 928 | 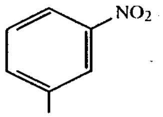 | $C_2H_5OOC$ | $(C_2H_5)_2NCH_2$ | H | H | HCl 199-200(d) |

-continued
| | | | | | | |
|---|---|---|---|---|---|---|
| 929 | 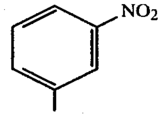 | $C_2H_5OOC$ | $CH_3$ | H | 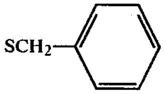 | 208-210 |
| 930 | 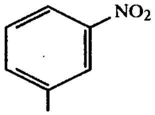 | $C_2H_5OOC$ | 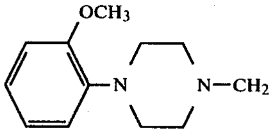 | H | H | HCl<br>122-123(d) |
| 931 | 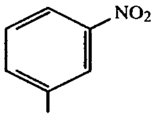 | $C_2H_5OOC$ | 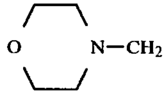 | H | H | HCl<br>244(d) |
| 932 | 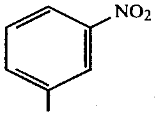 | $C_2H_5OOC$ | $(CH_3)_2CHNHCH_2$ | H | H | 55-57 |
| 933 | 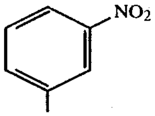 | $C_2H_5OOC$ | $(C_2H_5)_2NCH_2CH_2$ | H | H | $HCl.\frac{1}{2}H_2O$<br>209-211(d) |
| 934 | 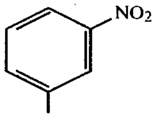 | $C_2H_5OOC$ | 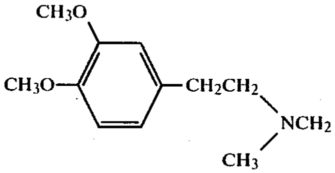 | H | H | 122-124 |
| 935 | 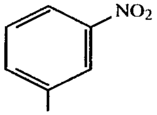 | $C_2H_5OOC$ | 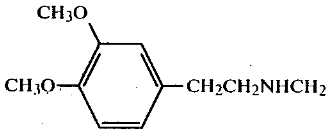 | H | H | 200-201 |

-continued
| | | | | | | |
|---|---|---|---|---|---|---|
| 936 | 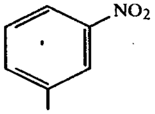 | $C_2H_5OOC$ | 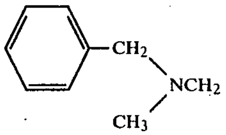 | H | H | 135-137 |
| 937 | 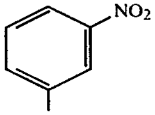 | $C_2H_5OOC$ | $(CH_3)_2NCH_2$ | H | H | HCl<br>229-230(d) |
| 938 | 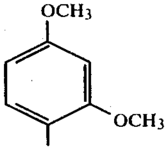 | $CH_3OOC$ | $(C_2H_5)_2NCH_2$ | H | H | HCl<br>206-208 |
| 939 | 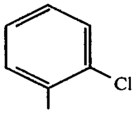 | $CH_3OOC$ | $(C_2H_5)_2NCH_2$ | H | H | HCl<br>217-218 |
| 940 | $CH_3$ | $C_2H_5OOC$ | $(C_2H_5)_2NCH_2$ | H | H | 100-102 |
| 941 | 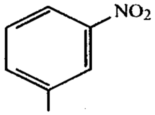 | $C_2H_5OOC$ | $(C_2H_5)_2NCH_2$ | H | 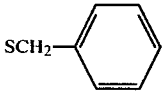 | HCl<br>155-157(d) |
| 942 | 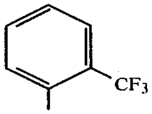 | $C_2H_5OOC$ | $(C_2H_5)_2NCH_2$ | H | H | HCl<br>206-207(d) |
| 943 | 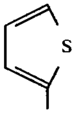 | $CH_3OOC$ | $(C_2H_5)_2NCH_2$ | H | H | HCl<br>186-188(d) |

-continued
| | | | | | | |
|---|---|---|---|---|---|---|
| 944 | 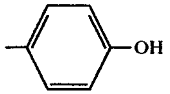 | $C_2H_5OOC$ | $(C_2H_5)_2NCH_2$ | H | H | $HCl\ H_2O$ 167-169(d) |
| 945 | 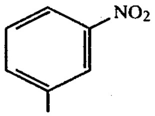 | $C_2H_5OOC$ | 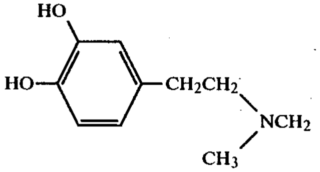 | H | H | $HCl \cdot \frac{1}{3}H_2O$ 179-181(d) |
| | 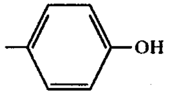 | $C_2H_5OOC$ | 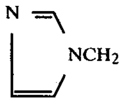 | H | H | $HCl\ \frac{1}{3}H_2O$ 228-230(d) |
| 946 | 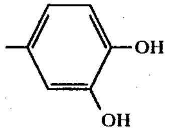 | $CH_3OOC$ | $CH_3$ | H | H | |
| 947 | 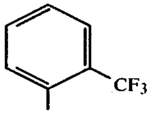 | $C_2H_5OOC$ | $CH_2OCOCH_3$ | H | H | |
| 948 | 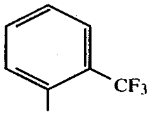 | $C_2H_5OOC$ | $CH_2OH$ | H | H | |
| 949 | 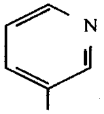 | $CH_3OOC$ | $CH_3$ | H | H | |

-continued
| | | | | | |
|---|---|---|---|---|---|
| 950 | 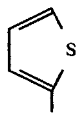 | $C_2H_5OOC$ | $C_3H_7$ | H | H |
| 951 | 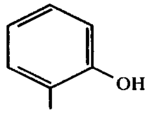 | $CH_3OOC$ | $CH_3$ | H | H |
| 952 | 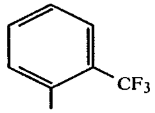 | $C_2H_5OOC$ | $CH_2Cl$ | H | H |
| 953 | 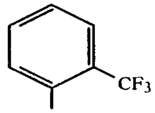 | $C_2H_5OOC$ | $CH_2F$ | H | H |
| 954 | 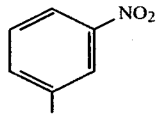 | $CH_3CO$ | $CH_3$ | H | H |
| 955 | 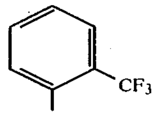 | 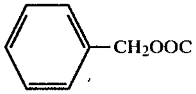 | $CH_3$ | H | H |
| 956 | 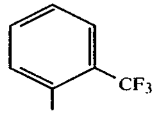 | HOOC | $CH_3$ | H | H |

-continued
| | | | | | |
|---|---|---|---|---|---|
| 957 | 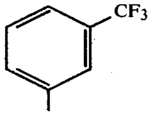 | $C_2H_5OOC$ | $CH_3$ | H | H |
| 958 | 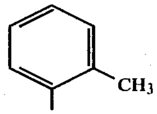 | $C_2H_5OOC$ | $CH_3$ | H | H |
| 959 | 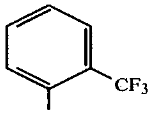 | $C_3H_7OOC$ | $CH_3$ | H | H |
| 960 | 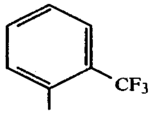 | $(CH_3)_2CHOOC$ | $CH_3$ | H | H |
| 961 | 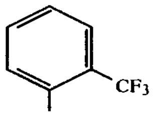 | $(CH_3)_2CHCH_2OOC$ | $CH_3$ | H | H |
| 962 | 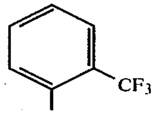 | $(CH_3)_3COOC$ | $CH_3$ | H | H |
| 963 | 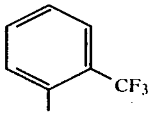 | 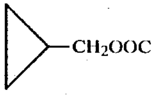 | $CH_3$ | H | H |

-continued
| | | | | | |
|---|---|---|---|---|---|
| 964 | 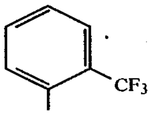 | 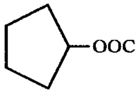 | $CH_3$ | H | H |
| 965 | 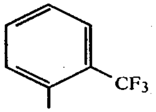 | 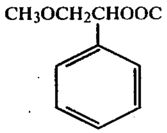 | $CH_3$ | H | H |
| 966 | 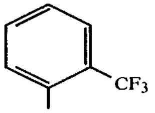 | $C_2H_5OOC$ | $CH_3$ | H | Cl |
| 967 | 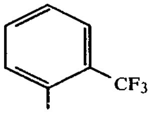 | 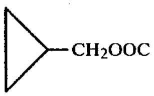 | $CH_3$ | H | CN |
| 968 | 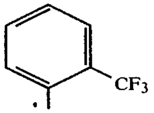 | $C_2H_5OOC$ | $CH_3$ | H | 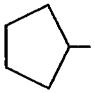 |
| 969 | 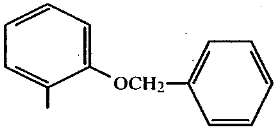 | $C_2H_5OOC$ | $CH_3$ | H | H |
| 970 | 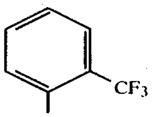 | $O_2N$ | $CH_3$ | H | H |

-continued
| | | | | | |
|---|---|---|---|---|---|
| 971 | 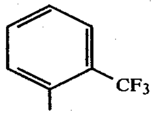 | 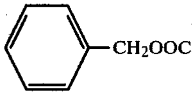 | $CH_3$ | $CH_2OC_2H_5$ | H |
| 972 | 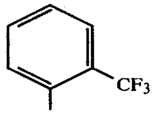 | HOOC | $CH_3$ | $CH_2OC_2H_5$ | H |
| 973 | 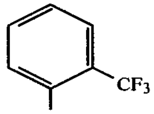 | $C_2H_5OOC$ | $CH_3$ | H | $CH_2N(C_2H_5)_2$ |
| 974 | 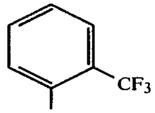 | 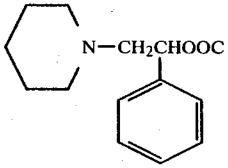 | $CH_3$ | H | H |
| 975 | 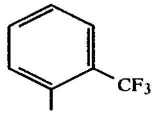 | $C_2H_5OOC$ | $CH_3$ | H | H |
| 976 | 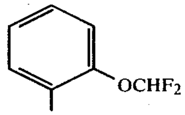 | $C_2H_5OOC$ | $CH_3$ | H | H |
| 977 | 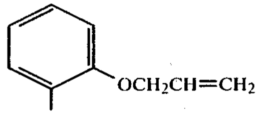 | $C_2H_5OOC$ | $CH_3$ | H | H |

-continued
| | | | | | |
|---|---|---|---|---|---|
| 978 | 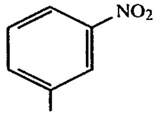 | $C_2H_5OOC$ | $CH_3$ | H | $COOC_2H_5$ |
| 979 | 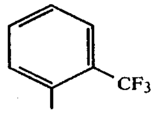 | $CH_3OOC$ | $CH_3$ | H | Br |
| 980 | 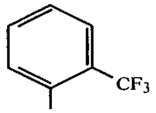 | $CH_3OOC$ | $CH_3$ | H | $NO_2$ |
| 981 | 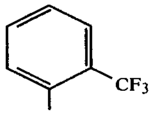 | $CH_3OOC$ | $CH_3$ | H | CN |
| 982 | 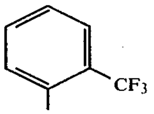 | $CH_3OOC$ | $CH_3$ | H | $CONH_2$ |
| 983 | 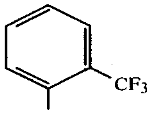 | $FCH_2CH_2OOC$ | $CH_3$ | H | H |
| 984 | 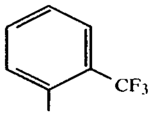 | $CH_3OOC$ | $CH_3$ | H | COOH |

-continued
| | | | | | |
|---|---|---|---|---|---|
| 985 | 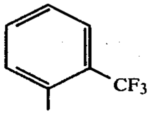 | $CH_3OCH_2CH_2OOC$ | $CH_3$ | H | H |
| 986 | 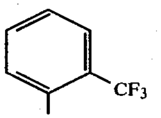 | $O_2N$ | $CH_3$ | H | $COOC_2H_5$ |
| 987 | 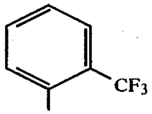 | $ClCH_2CH_2OOC$ | $CH_3$ | H | H |
| 988 | 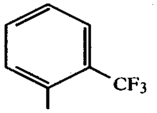 | $C_2H_5OOC$ | $CH_3$ | H | 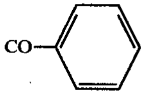 |
| 989 | 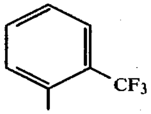 | $CF_3CH_2OOC$ | $CH_3$ | H | H |
| 990 | 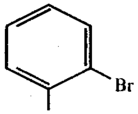 | $C_4H_9OOC$ | $CH_3$ | H | H |

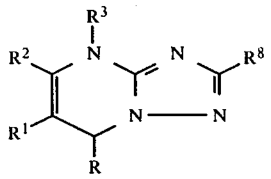
| No. | R | $R^1$ | $R^2$ | $R^3$ | $R^8$ |
|---|---|---|---|---|---|
| 991 | 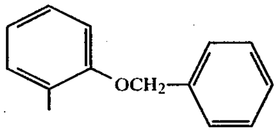 | 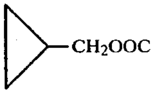 | $CH_3$ | H | H |
| 992 | 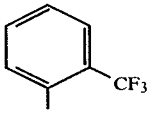 | 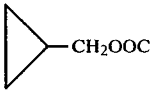 | $CH_3$ | H | $NO_2$ |
| 993 | 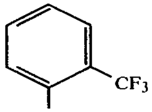 | 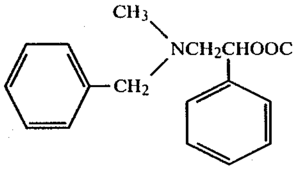 | $CH_3$ | H | H |
| 994 | 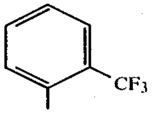 | $C_2H_5OOC$ | $CH_3$ | H | Br |
| 995 | 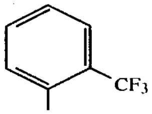 | $CH_3(CH_2)_7OOC$ | $CH_3$ | H | H |

-continued
| | | | | | |
|---|---|---|---|---|---|
| 996 | 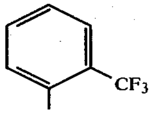 | $CH_3(CH_2)_5OOC$ | $CH_3$ | H | H |
| 997 | 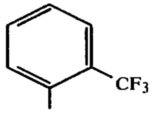 | $C_2H_5OOC$ | $CH_3$ | H | $COOC_2H_5$ |
| 998 | 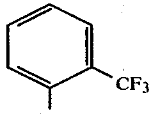 | $CH_2{=}CHCH_2OOC$ | $CH_3$ | H | H |
| 999 | 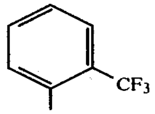 | 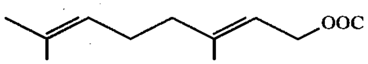 | $CH_3$ | H | H |
| 1000 | 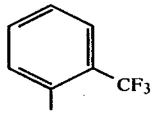 | $CH{\equiv}CCH_2OOC$ | $CH_3$ | H | H |
| 1001 | 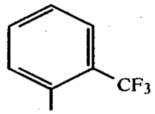 | $CH_3S(CH_2)_2OOC$ | $CH_3$ | H | H |
| 1002 | 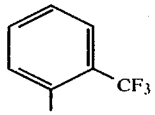 | $CH_3(CH_2)_4OOC$ | $CH_3$ | H | H |

-continued
| | | | | | |
|---|---|---|---|---|---|
| 1003 | 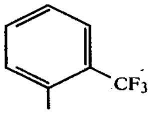 | 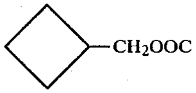 | $CH_3$ | H | H |
| 1004 | 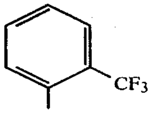 | $C_2H_5OOC$ | $CH_3$ | H | CN |
| 1005 | 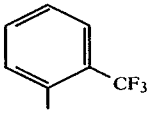 | 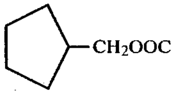 | $CH_3$ | H | H |
| 1006 | 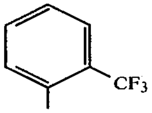 | 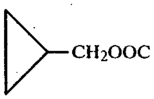 | $CH_3$ | H | $NH_2$ |
| 1007 | 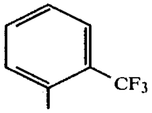 | 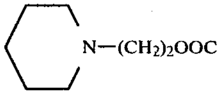 | $CH_3$ | H | H |
| 1008 | 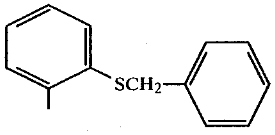 | $C_2H_5OOC$ | $CH_3$ | H | H |
| 1009 | 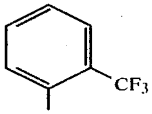 | 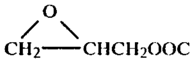 | $CH_3$ | H | H |

-continued
| | | | | | |
|---|---|---|---|---|---|
| 1010 | 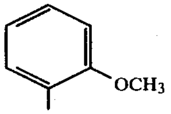 | $C_2H_5OOC$ | $CH_3$ | H | H |
| 1011 | 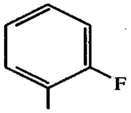 | $C_2H_5OOC$ | $CH_3$ | H | H |
| 1012 | 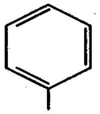 | $CH_3OOC$ | $CH_3$ | H | H |
| 1013 | 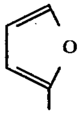 | $C_2H_5OOC$ | $C_3H_7$ | H | H |
| 1014 | 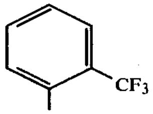 | $CH_3(CH_2)_{21}OOC$ | $CH_3$ | H | H |
| 1015 | 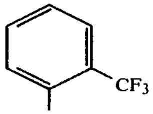 | 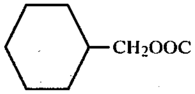 | $CH_3$ | H | H |
| 1016 | 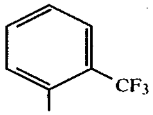 | $(CH_3)_3CCH_2OOC$ | $CH_3$ | H | H |

-continued
| | | | | |
|---|---|---|---|---|
| 1017 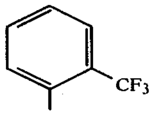 | 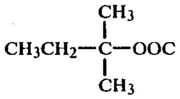 | $CH_3$ | H | H |
| 1018 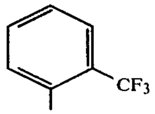 | 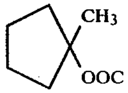 | $CH_3$ | H | H |
| 1019 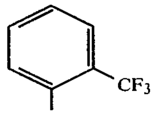 | $C_2H_5OOC$ | $C_3H_7$ | H | H |
| 1020 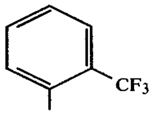 | $C_2H_5OOC$ | $CH_3$ | H | $NO_2$ |
| 1021 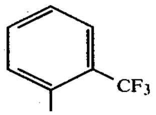 | $C_2H_5OOC$ | $CH_3$ | H | $CONH_2$ |
| 1022 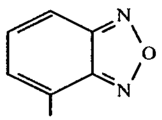 | $C_2H_5OOC$ | $CH_3$ | H | H |
| 1023 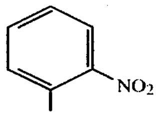 | $C_2H_5OOC$ | $CH_3$ | H | H |

-continued
| | | | | |
|---|---|---|---|---|
| 1024 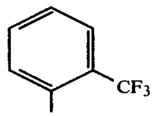 | 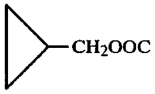 | $CH_3$ | H | $NHCOCH_3$ |
| 1025 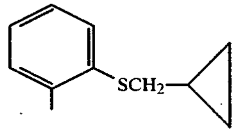 | $C_2H_5OOC$ | $CH_3$ | H | H |
| 1026 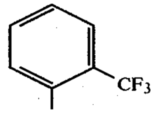 | 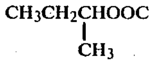 | $CH_3$ | H | H |
| 1027 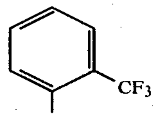 | 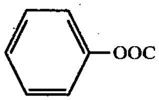 | $CH_3$ | H | H |
| 1028 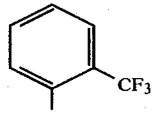 | 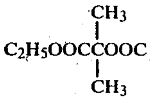 | $CH_3$ | H | H |
| 1029 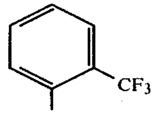 | CN | $CH_3$ | H | H |
| 1030 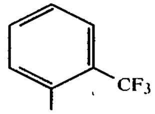 | $C_2H_5OOC$ | $CF_3$ | H | H |

-continued
| | | | | | |
|---|---|---|---|---|---|
| 1031 | 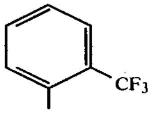 | $CH_3(CH_2)_{15}OOC$ | $CH_3$ | H | H |
| 1032 | 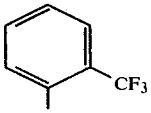 | 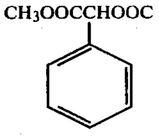 | $CH_3$ | H | H |
| 1033 | 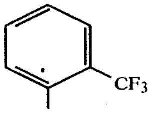 | 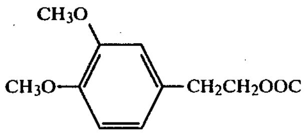 | $CH_3$ | H | H |
| 1034 | 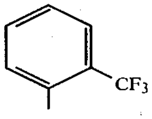 | 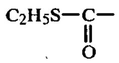 | $CH_3$ | H | H |
| 1035 | 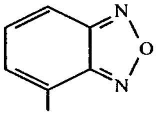 | $O_2N$ | $CH_3$ | H | H |
| 1036 | 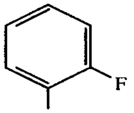 | 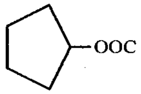 | $CH_3$ | H | H |
| 1037 | 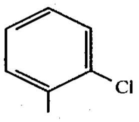 | $(CH_3)_2CHOOC$ | $CH_3$ | H | H |

-continued
| | | | | | |
|---|---|---|---|---|---|
| 1038 | 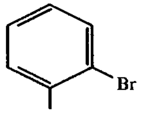 | $(CH_3)_2CHOOC$ | $CH_3$ | H | H |
| 1039 | 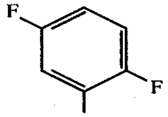 | $(CH_3)_2CHOOC$ | $CH_3$ | H | H |
| 1040 | 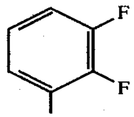 | $(CH_3)_2CHOOC$ | $CH_3$ | H | H |
| 1041 | 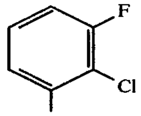 | $(CH_3)_2CHOOC$ | $CH_3$ | H | H |
| 1042 | 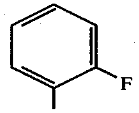 | $CH_3OCH_2CHOOC$ 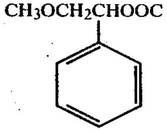 | $CH_3$ | H | H |
| 1043 | 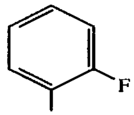 | $(CH_3)_2CHOOC$ | $CH_3$ | H | H |
| 1044 | 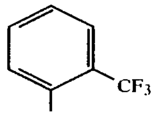 | $(C_2H_5)_2CHOOC$ | $CH_3$ | H | H |

-continued
| | | | | | |
|---|---|---|---|---|---|
| 1045 | 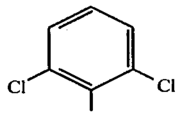 | $C_2H_5OOC$ | $CH_3$ | H | H |
| 1046 | 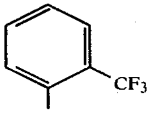 | $(CH_3)_2CHOOC$ | $CH_3$ | $CH_3$ | H |
| 1047 | 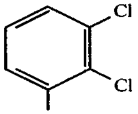 | $C_2H_5OOC$ | $CH_3$ | H | H |
| 1048 | 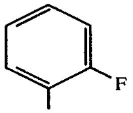 | 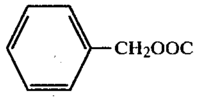 | $CH_3COO(CH_2)_3$ | H | H |
| 1049 | 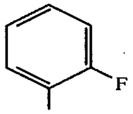 | 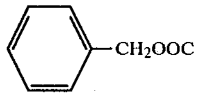 | $HO(CH_2)_3$ | H | H |
| 1050 | 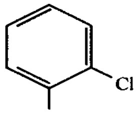 | $(CH_3)_3COOC$ | $CH_3$ | H | H |
| 1051 | 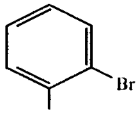 | $(CH_3)_3COOC$ | $CH_3$ | H | H |

-continued
| | | | | | |
|---|---|---|---|---|---|
| 1052 | 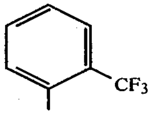 | $ClCH_2CH_2CH_2CH_2OOC$ | $CH_3$ | H | H |
| 1053 | 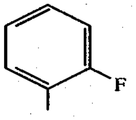 | $(CH_3)_2CHOOC$ | $CH_3$ | H | COOH |
| 1054 | 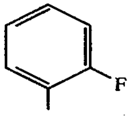 | $(ClCH_2)_2CHOOC$ | $CH_3$ | H | H |
| 1055 | 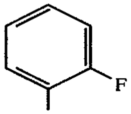 | $(CH_3)_2CHOOC$ | $CH_3COOCH_2$ | H | H |
| 1056 | 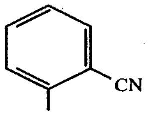 | $(CH_3)_3COOC$ | $CH_3$ | H | H |
| 1057 | 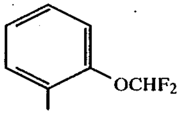 | $(CH_3)_3COOC$ | $CH_3$ | H | H |
| 1058 | 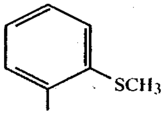 | $(CH_3)_2CHOOC$ | $CH_3$ | H | H |

-continued
| | | | | | |
|---|---|---|---|---|---|
| 1059 | 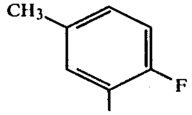 | $(CH_3)_2CHOOC$ | $CH_3$ | H | H |
| 1060 | 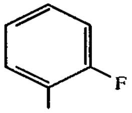 | 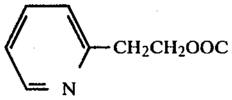 | $CH_3$ | H | H |
| 1061 | 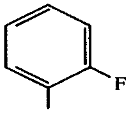 | 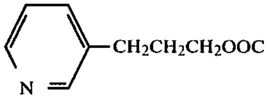 | $CH_3$ | H | H |
| 1062 | 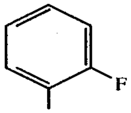 | 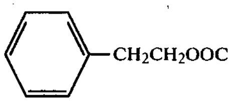 | $CH_3$ | H | H |
| 1063 | 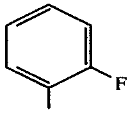 | 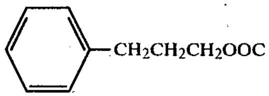 | $CH_3$ | H | H |
| 1064 | 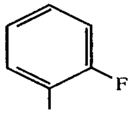 | $C_2H_5OOC$ | $H_2NCH_2$ | H | H |
| 1065 | 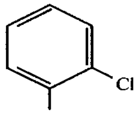 | H | $CH_3$ | H | H |

-continued
| | | | | | |
|---|---|---|---|---|---|
| 1066 | 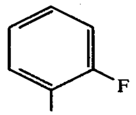 | $(CH_3)_2CHOOC$ | $CH_3$ | H | $COCH_3$ |
| 1067 | 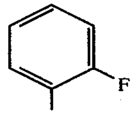 | $(CH_3)_2CHOOC$ | $CH_3$ | H | 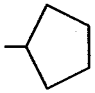 |
| 1068 | 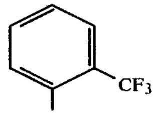 | $CH_3OCH_2CHOOC$ 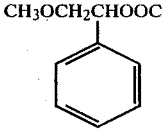 | $CH_3$ | H | H |
| 1069 | 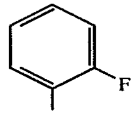 | $(CH_3)_2CHOOC$ | 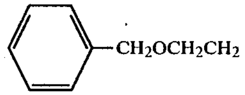 | H | H |
| 1070 | 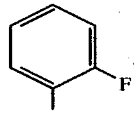 | $(CH_3)_2CHOOC$ | 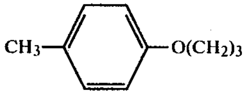 | H | H |
| 1071 | 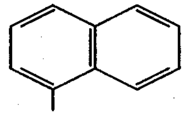 | $(CH_3)_2CHOOC$ | $CH_3$ | H | H |

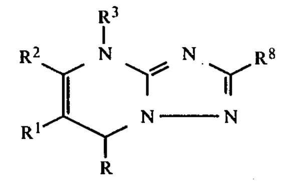
| No. | R | $R^1$ | $R^2$ | $R^3$ | R8 |
|---|---|---|---|---|---|
| 1072 | 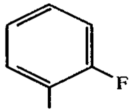 | $(CH_3)_2CHOOC$ | $CH_3$ | H | $-CH_2F$ |
| 1073 | 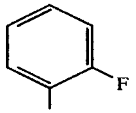 | $(CH_3)_3COOC$ | $CH_3$ | H | $-CH_2CF_3$ |
| 1074 | 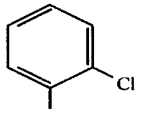 | $(CH_3)_2CHOOC$ | $CH_3$ | H | $CHF_2$ |
| 1075 | 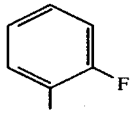 | 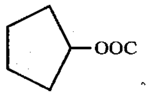 | $CH_3$ | H | $-CH_2CH{=}CH_2$ |
| 1076 | 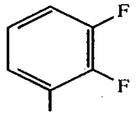 | $(CH_3)_2CHOOC$ | $CH_3$ | H | $-C{\equiv}CH$ |
| 1077 | 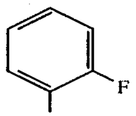 | $C_2H_5OOC$ | $CH_3$ | H | $-CH_2OCH_2CH_3$ |

-continued
| | | | | | |
|---|---|---|---|---|---|
| 1078 | 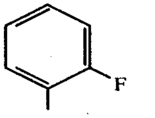 | $(CH_3)_2CHOOC$ | $CH_3$ | H | 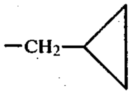 |
| 1079 | 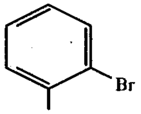 | $CH_3OOC$ | $CH_3$ | H | $-(CH_2)_3CN$ |
| 1080 | 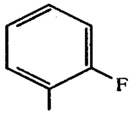 | 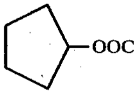 | $CH_3$ | H | $-CH_2CH_2NO_2$ |
| 1081 | 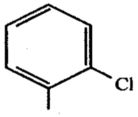 | $CH_3(CH_2)_3OOC$ | $CH_3$ | H | 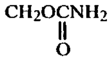 |
| 1082 | 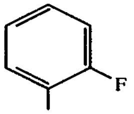 | $(CH_3)_2CHOOC$ | $CH_3$ | H | 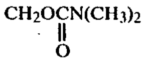 |
| 1083 | 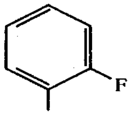 | $(CH_3)_2COOC$ | $CH_3$ | H | 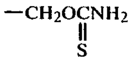 |
| 1084 | 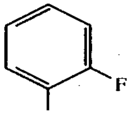 | $(CH_3)_2CHOOC$ | $CH_3$ | H | 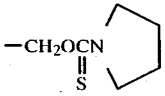 |

-continued
| | | | | | |
|---|---|---|---|---|---|
| 1085 | 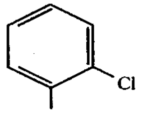 | $C_2H_5OOC$ | $CH_3$ | H | $-CON(C_2H_5)_2$ |
| 1086 | 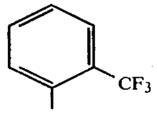 | $(CH_3)_2CHOOC$ | $CH_3$ | H | $CH_2CH{=}CH_2$ |
| 1087 | 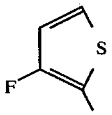 | $(CH_3)_2CHOOC-$ | $CH_3$ | H | H |
| 1088 | 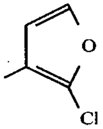 | $C_2H_5OOC$ | $CH_3$ | H | H |
| 1089 | 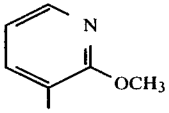 | $(CH_3)_2CHOOC$ | $CH_3$ | H | H |
| 1090 | 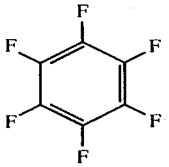 | $(CH_3)_2CHOOC$ | $CH_3$ | H | H |
| 1091 | 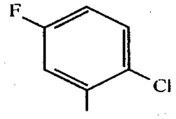 | $(CH_3)_3COOC$ | $CH_3$ | H | H |

-continued
| | | | | |
|---|---|---|---|---|
| 1092 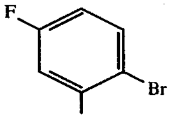 | $CH_3CH_2CH_2OOC$ | $CH_3$ | H | H |
| 1093 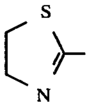 | $CH_3OOC$ | $CH_3$ | H | H |
| 1094 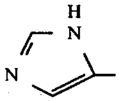 | 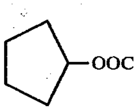 | $CH_3$ | H | H |
| 1095 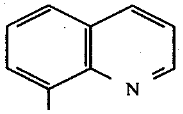 | $(CH_3)_2CHOOC$ | $CH_3$ | H | H |
| 1096 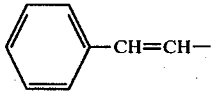 | $(CH_3)_2CHOOC$ | $CH_3$ | H | H |
| 1097 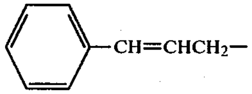 | $(CH_3)_3COOC$ | $CH_3$ | H | H |
| 1098 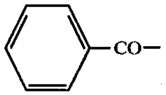 | $C_2H_5OOC$ | $CH_3$ | H | H |
| 1099 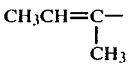 | $(CH_3)_2CHOOC$ | $CH_3$ | H | H |
| 1100 $CH{\equiv}C-CH_2-$ | $(CH_3)_3COOC$ | $CH_3$ | H | H |

-continued
| | | | | | |
|---|---|---|---|---|---|
| 1101 | 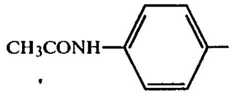 | $C_2H_5OOC$ | $CH_3$ | H | H |
| 1102 | 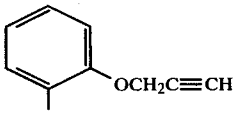 | $(CH_3)_2CHOOC$ | $CH_3$ | H | H |
| 1103 | 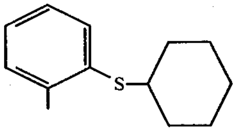 | $C_2H_5OOC$ | $CH_3$ | H | H |
| 1104 | 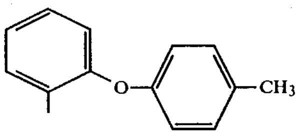 | $CH_3CH_2CH_2OOC$ | $CH_3$ | H | H |
| 1105 | 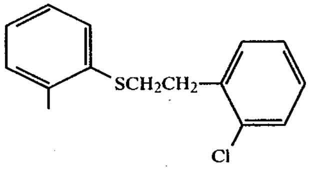 | $CH_3(CH_2)_3OOC$ | $CH_3$ | H | H |
| 1106 | 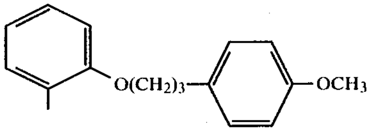 | 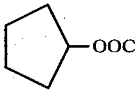 | $CH_3$ | H | H |
| 1107 | 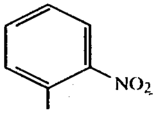 | $(CH_3)_2CHOOC$ | $CH_3$ | H | CN |

-continued
| | | | | | |
|---|---|---|---|---|---|
| 1108 | 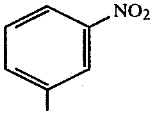 | $(CH_3)_2CHOOC$ | $CH_3$ | H | CN |
| 1109 | 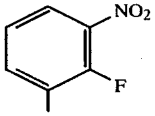 | $(CH_3)_2CHCH_2OOC$ | $CH_3$ | H | CN |
| 1110 | 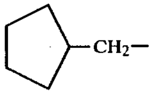 | $CH_3OOC$ | $CH_3$ | H | H |
| 1111 | 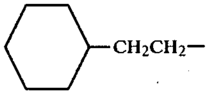 | 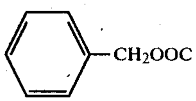 | $CH_3$ | H | H |
| 1112 | 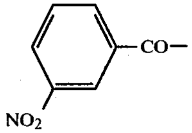 | $CH_3OCH_2CH_2OOC$ | $CH_3$ | H | H |
| 1113 | 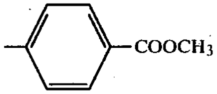 | $CH_3OOC$ | $CH_3$ | H | H |
| 1114 | 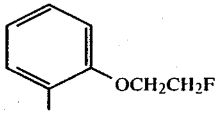 | $(CH_3)_2CHOOC$ | $CH_3$ | H | H |
| 1115 | 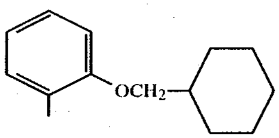 | 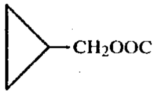 | $CH_3$ | H | H |

-continued
| | | | | | |
|---|---|---|---|---|---|
| 1116 | 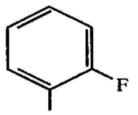 | $(CH_3)_2CHOSC$ | $CH_3$ | H | H |
| 1117 | 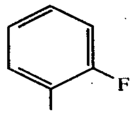 | $(CH_3)_2CHSSC$ | $CH_3$ | H | H |
| 1118 | 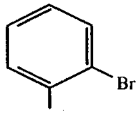 | $H_2NOC$ | $CH_3$ | H | H |
| 1119 | 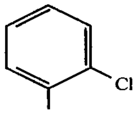 | 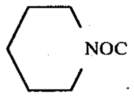 | $CH_3$ | H | H |
| 1120 | 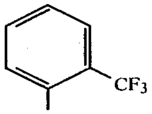 | $(CH_3)_2CHNHOC$ | $CH_3$ | H | H |
| 1121 | 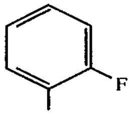 | $(C_2H_5)_2NOC$ | $CH_3$ | H | H |
| 1122 | 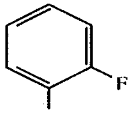 | $H_2NSC$ | $CH_3$ | H | H |

-continued
| | | | | | |
|---|---|---|---|---|---|
| 1123 | 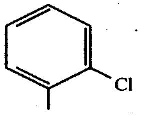 | 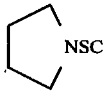 | $CH_3$ | H | H |
| 1124 | 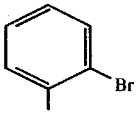 | $(CH_3)_3CNHSC$ | $CH_3$ | H | H |
| 1125 | 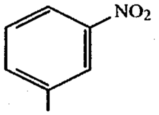 | 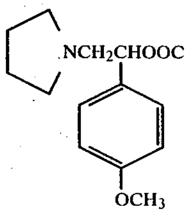 | $CH_3$ | H | H |
| 1126 | 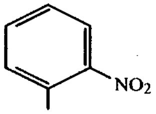 | 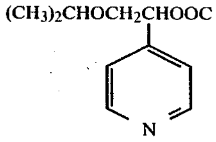 | $CH_3$ | H | H |
| 1127 | 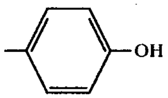 | 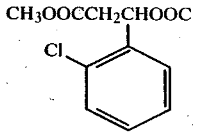 | $CH_3$ | H | H |
| 1128 | 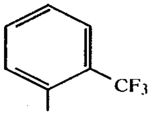 | 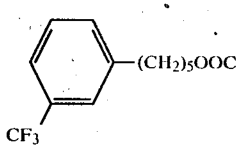 | $CH_3$ | H | H |

-continued
| | | | | | |
|---|---|---|---|---|---|
| 1129 | 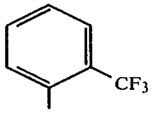 | $C_2H_5OOC$ | 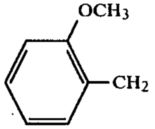 | H | H |
| 1130 | 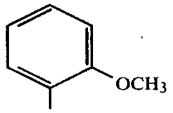 | $CH_3OOC$ | 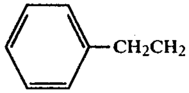 | H | H |
| 1131 | 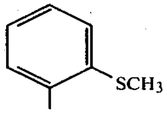 | $(CH_3)_2CHOOC$ | 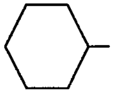 | H | H |
| 1132 | 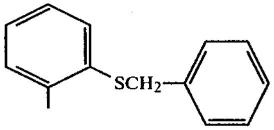 | $CH_3(CH_2)_2OOC$ | 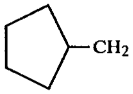 | H | H |
| 1133 | 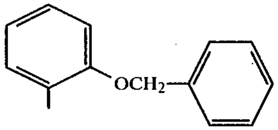 | $CH_3(CH_2)_3OOC$ | $H_2NCH_2CH_2$ | H | H |
| 1134 | 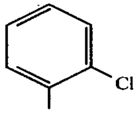 | $CH_3(CH_2)_3OOC$ | $CH_3CONHCH_2CH_2$ | H | H |
| 1135 | 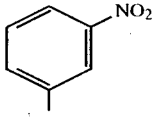 | $(CH_3)_2CHCH_2OOC$ | $HOCH_2CH_2OCH_2$ | H | H |

-continued
| | | | | |
|---|---|---|---|---|
| 1136 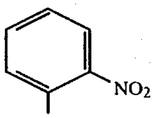 | $C_2H_5OOC$ | $H_2N(CH_2)_2OCH_2$ | H | H |
| 1137 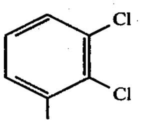 | $CH_3OOC$ | 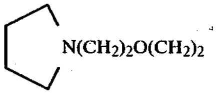 | H | H |
| 1138 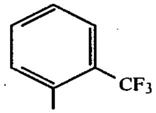 | $(CH_3)_2CHOOC$ | $CH_3$ | $C_3H_7$ | H |
| 1139 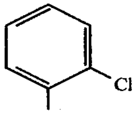 | $(CH_3)_3COOC$ | $CH_3$ | 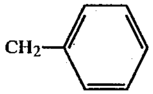 | H |
| 1140 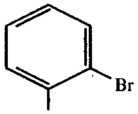 | $C_3H_7OOC$ | $CH_3$ | 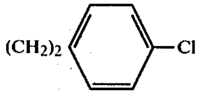 | H |
| 1141 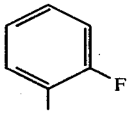 | 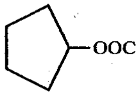 | $CH_3$ | 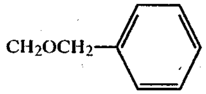 | H |
| 1142 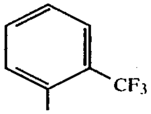 | $CH_3(CH_2)_3OOC$ | $CH_3$ | $COCH_3$ | H |

-continued
| | | | | | |
|---|---|---|---|---|---|
| 1143 | 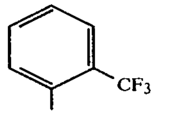 | $(CH_3)_2CHS\overset{O}{\overset{\|}{C}}$ | $CH_3$ | H | H |
| 1144 | 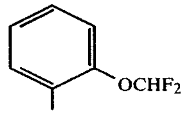 | $CH_3OOC$ | $CH_3$ | H | H |
| 1145 | 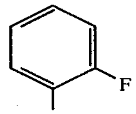 | $C_3H_7OOC$ | $CH_3$ | H | H |
| 1146 | 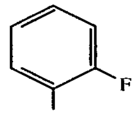 | $(CH_3)_3COOC$ | $CH_3$ | H | H |
| 1147 | 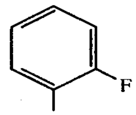 | $(CH_3)_3COOC$ | $CH_3$ | H | Br |
| 1148 | 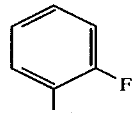 | $(CH_3)_3COOC$ | $CH_3$ | H | $CH_3$ |
| 1149 | 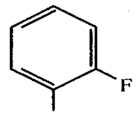 | $(CH_3)_3COOC$ | $CH_3$ | H | Cl |

-continued
| | | | | | |
|---|---|---|---|---|---|
| 1150 | 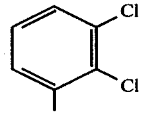 | $(CH_3)_3COOC$ | $CH_3$ | H | H |
| 1151 | 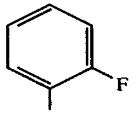 | $(CH_3)_2CHCH_2OOC$ | $CH_3$ | H | H |
| 1152 | 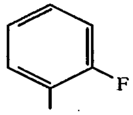 | $C_4H_9OOC$ | $CH_3$ | H | H |
| 1153 | 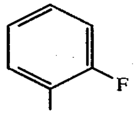 | $(CH_3)_2CHOOC$ | $CH_3$ | H | $CH_3$ |
| 1154 | 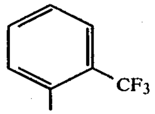 | $(CH_3)_2NCH_2CH_2OOC$ | $CH_3$ | H | H |

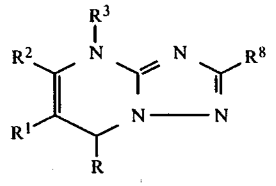
| No. | R | $R^1$ | $R^2$ | $R^3$ | $R^8$ |
|---|---|---|---|---|---|
| 1155 | 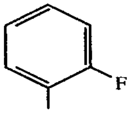 | $(CH_3)_2CHOOC$ | $CH_3$ | H | $NO_2$ |
| 1156 | 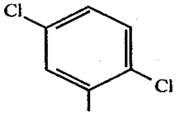 | $(CH_3)_2CHOOC$ | $CH_3$ | H | H |
| 1157 | 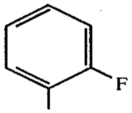 | $(CH_3)_2CHOOC$ | $CH_2Cl$ | H | H |
| 1158 | 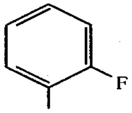 | $(CH_3)_2CHOOC$ | $CH_2N(C_2H_5)_2$ | H | H |
| 1159 | 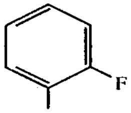 | 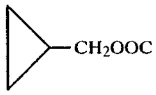 | $CH_3$ | H | H |
| 1160 | 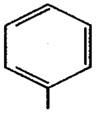 | $(CH_3)_2CHOOC$ | $CH_3$ | H | H |

-continued
| | | | | | |
|---|---|---|---|---|---|
| 1161 | 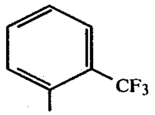 | $(CH_3)_2CHOOC$ | $CH_3$ | $COOC_2H_5$ | H |
| 1162 | 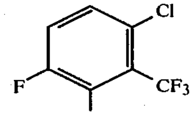 | $C_2H_5OOC$ | $CH_3$ | H | H |
| 1163 | 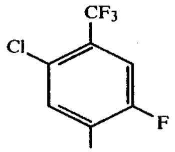 | $(CH_3)_2CHOOC$ | $CH_3$ | H | H |
| 1164 | 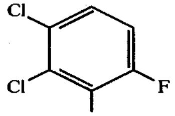 | $C_2H_5OOC$ | $CH_3$ | H | H |
| 1165 | 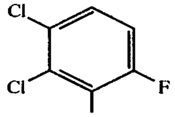 | $(CH_3)_2CHOOC$ | $CH_3$ | H | H |
| 1166 | 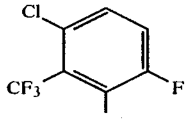 | $(CH_3)_2CHOOC$ | $CH_3$ | H | H |
| 1167 | 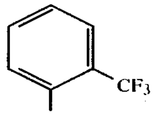 | $(ClCH_2)_2CHOOC$ | $CH_3$ | H | H |

-continued
| | | | | | |
|---|---|---|---|---|---|
| 1168 | 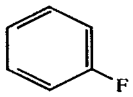 | $ClCH_2CH_2CHOOC$ | $CH_3$ | H | H |
| 1169 | 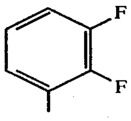 | $(CH_3)_2CHOOC$ | $CH_3$ | H | CN |
| 1170 | 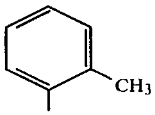 | 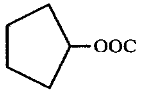 | $CH_3$ | H | H |
| 1171 | 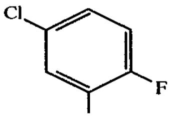 | $(CH_3)_2CHOOC$ | $CH_3$ | H | H |
| 1172 | 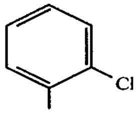 | 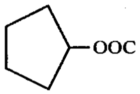 | $CH_3$ | H | H |
| 1173 | 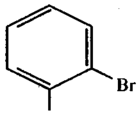 | 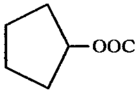 | $CH_3$ | H | H |
| 1174 | 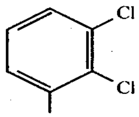 | $(CH_3)_3CHOOC$ | $CH_3$ | H | H |

-continued
| | | | | | |
|---|---|---|---|---|---|
| 1175 | 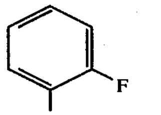 | $(CH_3)_2CHOOC$ | $CH_3$ | H | $CH_2OH$ |
| 1176 | 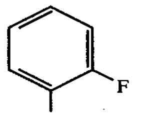 | $(CH_3)_2CHOOC$ | $CH_3$ | H | $CH_2OCOCH_3$ |
| 1177 | 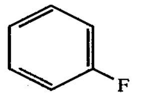 | $(CH_3)_2CHOOC$ | $Cl(CH_2)_3$ | H | H |
| 1178 | 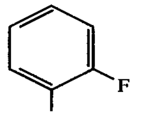 | $(CH_3)_2CHOOC$ | $CH_3COO(CH_2)_3$ | H | H |
| 1179 | 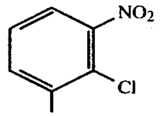 | $(CH_3)_2CHOOC$ | $CH_3$ | H | H |
| 1180 | 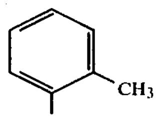 | $(CH_3)_2CHCH_2OOC$ | $CH_3$ | H | H |
| 1181 | 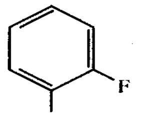 | $(CH_3)_2CHOOC$ | $CH_3$ | H | F |

-continued
| | | | | | |
|---|---|---|---|---|---|
| 1182 | 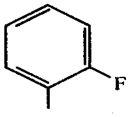 | $(CH_3)_2CHOOC$ | $CH_2F$ | H | H |
| 1183 | 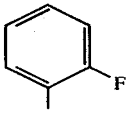 | $(CH_3)_2CHOOC$ | $CH_2CH_2OH$ | H | H |
| 1184 | 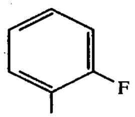 | $(CH_3)_2CHOOC$ | $(CH_2)_3OH$ | H | H |
| 1185 | 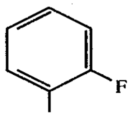 | $C_2H_5OOC$ | 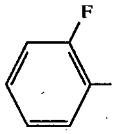 | H | H |
| 1186 | 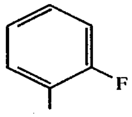 | CN | $CH_3$ | H | H |
| 1187 | 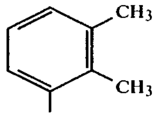 | $(CH_3)_2CHOOC$ | $CH_3$ | H | H |
| 1188 | 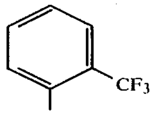 | $(CH_3)_2CHOOC$ | $C_4H_9$ | H | H |

-continued
| | | | | | |
|---|---|---|---|---|---|
| 1189 | 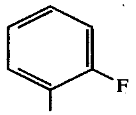 | $(CH_3)_2CHOOC$ | $CH_2OCOCH_3$ | H | H |
| 1190 | 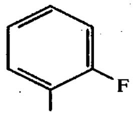 | $(CH_3)_2CHOOC$ | $C_2H_5$ | H | H |
| 1191 | 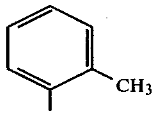 | $(CH_3)_2CHOOC$ | $CH_3$ | H | H |
| 1192 | 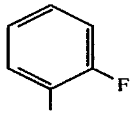 | $(CH_3)_2CHOOC$ | $CH_3$ | H | CN |
| 1193 | 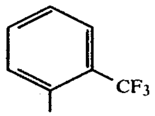 | $(CH_3)_2CHOOC$ | $CH_3$ | H | Cl |
| 1194 | 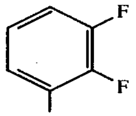 | $C_2H_5OOC$ | $CH_3$ | H | H |
| 1195 | 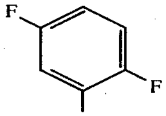 | $C_2H_5OOC$ | $CH_3$ | H | H |

-continued
| | | | | | |
|---|---|---|---|---|---|
| 1196 | 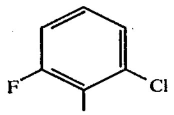 | $C_2H_5OOC$ | $CH_3$ | H | H |
| 1197 | 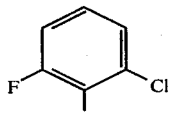 | $(CH_3)_2CHOOC$ | $CH_3$ | H | H |
| 1198 | 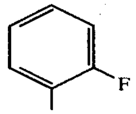 | $(CH_3)_2CHOOC$ | $CH(CH_3)_2$ | H | H |
| 1199 | 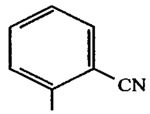 | $(CH_3)_2CHOOC$ | $CH_3$ | H | H |
| 1200 | 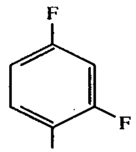 | $C_2H_5OOC$ | $CH_3$ | H | H |
| 1201 | 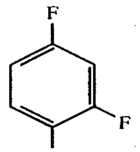 | $(CH_3)_2CHOOC$ | $CH_3$ | H | H |
| 1202 | 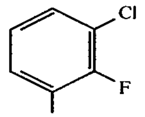 | $C_2H_5OOC$ | $CH_3$ | H | H |

-continued
| | | | | | |
|---|---|---|---|---|---|
| 1203 | 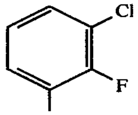 | $(CH_3)_2CHOOC$ | $CH_3$ | H | H |
| 1204 | 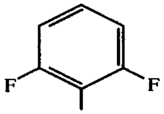 | $C_2H_5OOC$ | $CH_3$ | H | H |
| 1205 | 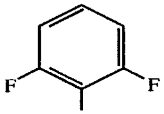 | $(CH_3)_2CHOOC$ | $CH_3$ | H | H |
| 1206 | 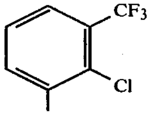 | $C_2H_5OOC$ | $CH_3$ | H | H |
| 1207 | 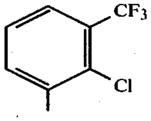 | $(CH_3)_2CHOOC$ | $CH_3$ | H | H |
| 1208 | 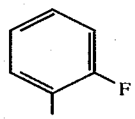 | $(CH_3)_2CHOOC$ | $CH_2OH$ | H | H |
| 1209 | 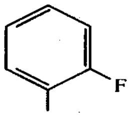 | $(CH_3)_2CHOOC$ | $C_4H_9$ | H | H |

-continued
| | | | | | |
|---|---|---|---|---|---|
| 1210 | 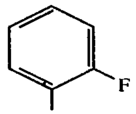 | $(CH_3)_2CHOOC$ | $CH_3$ | H | $CH(CH_3)_2$ |
| 1211 | 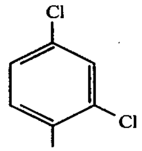 | $(CH_3)_2CHOOC$ | $CH_3$ | H | H |
| 1212 | 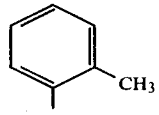 | $(CH_3)_2CHOOC$ | $CH_3$ | H | H |
| 1213 | 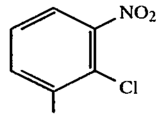 | $C_2H_5OOC$ | $CH_3$ | H | H |
| 1214 | 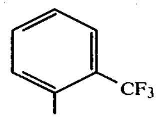 | $C_2H_5OOC$ | $CH_3NHCOOCH_2$ | H | H |
| 1215 | 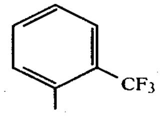 | $C_2H_5OOC$ | $CH_3$ | H | F |
| 1216 | 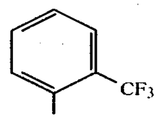 | $C_2H_5OOC$ | $CH_3$ | H | $CH_2OH$ |

-continued
| | | | | | |
|---|---|---|---|---|---|
| 1217 | 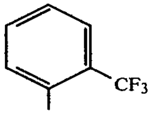 | $C_2H_5OOC$ | $CH_3$ | H | $C_3H_7$ |
| 1218 | 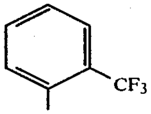 | $C_2H_5OOC$ | $(C_2H_5)_2NCH_2$ | H | H |
| 1219 | 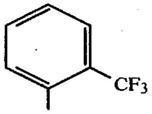 | $C_2H_5OOC$ | $(CH_3)_3C$ | H | H |
| 1220 | 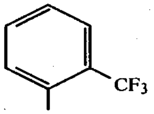 | $C_2H_5OOC$ | $CH_3NHCSOCH_2$ | H | H |
| 1221 | 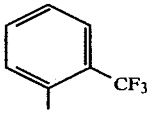 | $C_2H_5OOC$ | $CH_3$ | H | $CH_3$ |
| 1222 | 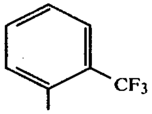 | $C_2H_5OOC$ | $CH_3$ | 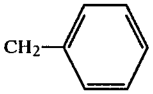 | H |
| 1223 | 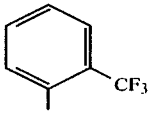 | $C_2H_5OOC$ | 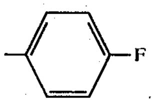 | H | H |

-continued
| | | | | | |
|---|---|---|---|---|---|
| 1224 | 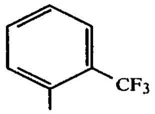 | $H_2NOC$ | $CH_3$ | H | H |
| 1225 | 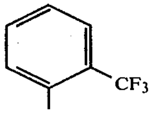 | $H_2NSC$ | $CH_3$ | H | H |
| 1226 | 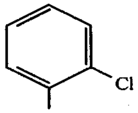 | $(CH_3)_2CHOOC$ | $CH_3$ | $CH_2CH_2Cl$ | H |
| 1227 | 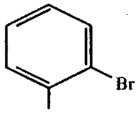 | $(CH_3)_3CHOOC$ | $CH_3$ | $(CH_2)_3OSO_2CH_3$ | H |
| 1228 | 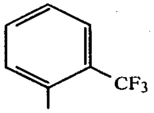 | 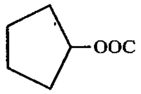 | $CH_3$ | 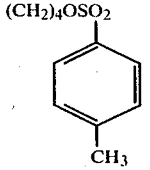 | H |
| 1229 | 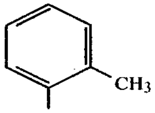 | $C_2H_5OOC$ | $CH_3$ | $CH_2CH_2OH$ | H |
| 1230 | 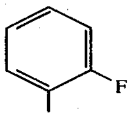 | $(CH_3)_2CHOOC$ | $CH_3$ | 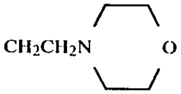 | H |

-continued
| | | | | | |
|---|---|---|---|---|---|
| 1231 | 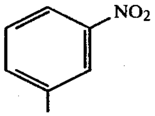 | $CH_3OOC$ | $CH_3$ | $(CH_2)_3NC_2H_5$ | H |
| 1232 | 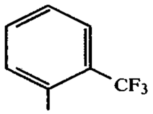 | $C_2H_5OOC$ | $CH_3$ | H | H |
| 1233 | 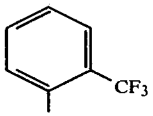 | $C_2H_5OOC$ | $CH_3$ | $CH_3$ | H |
| 1234 | 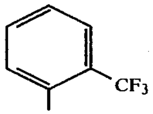 | $C_2H_5OOC$ | $CH_3$ | 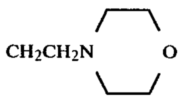 | H |
| 1235 | 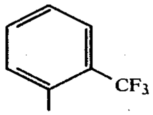 | 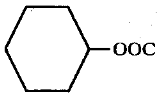 | $CH_3$ | H | H |
| 1236 | 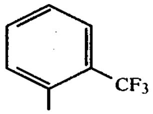 | $C_2H_5OOC$ | $C_2H_5OCH_2$ | H | H |
| 1237 | 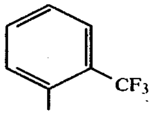 | $C_2H_5OOC$ | $CH_2Cl$ | H | H |
| 1238 | 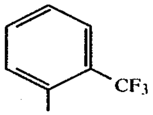 | $C_2H_5OOC$ | $CH_3$ | H | $NHCOCH_3$ |
(d: decomposition)

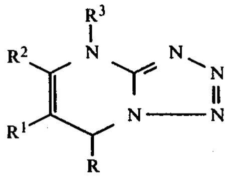
| No. | R | $R^1$ | $R^2$ | $R^3$ | M.p. (°C.) |
|---|---|---|---|---|---|
| 1239 | 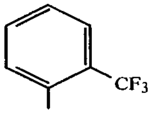 | $C_2H_5OOC$ | $CH_3$ | H | 220-221 |
| 1240 | 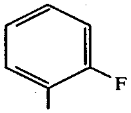 | $(CH_3)_2CHOOC$ | $CH_3$ | H | 208-209 |
| 1241 | 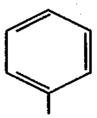 | $(CH_3)_2CHOOC$ | $CH_3$ | H | 210-211 |
| 1242 | 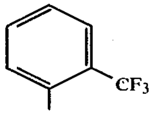 | $(CH_3)_2CHOOC$ | $CH_3$ | H | 227-229 |
| 1243 | 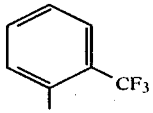 | $CH_3OOC$ | $CH_3$ | H | |
| 1244 | 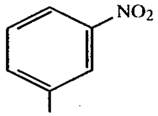 | $C_2H_5OOC$ | $(C_2H_5)_2NCH_2$ | H | HCl<br>201-203 (d) |

-continued
| | | | | |
|---|---|---|---|---|
| 1245 | 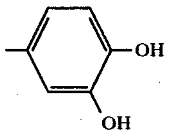 | $CH_3OOC$ | $CH_3$ | H |
| 1246 | 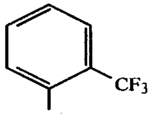 | $C_2H_5OOC$ | $CH_2OCOCH_3$ | H |
| 1247 | 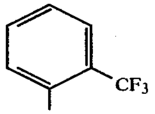 | $C_2H_5OOC$ | $CH_2OH$ | H |
| 1248 | 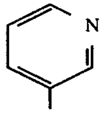 | $CH_3OOC$ | $CH_3$ | H |
| 1249 | 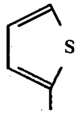 | $C_2H_5OOC$ | $C_3H_7$ | H |
| 1250 | 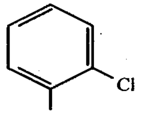 | $C_2H_5OOC$ | $CH_3$ | H |
| 1251 | 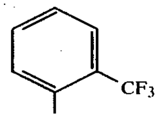 | $C_4H_9OOC$ | $CH_3$ | H |

-continued
| | | | | |
|---|---|---|---|---|
| 1252 | 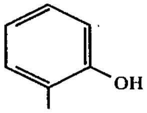 | $CH_3OOC$ | $CH_3$ | H |
| 1253 | 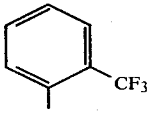 | $C_2H_5OOC$ | $CH_2Cl$ | H |
| 1254 | 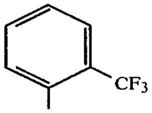 | $C_2H_5OOC$ | $CH_2F$ | H |
| 1255 | 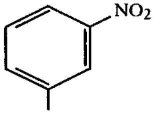 | $CH_3CO$ | $CH_3$ | H |
| 1256 | 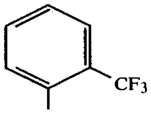 | 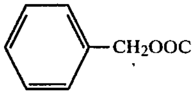 | $CH_3$ | H |
| 1257 | 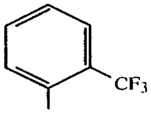 | HOOC | $CH_3$ | H |
| 1258 | 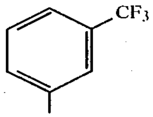 | $C_2H_5OOC$ | $CH_3$ | H |

-continued
| | | | | |
|---|---|---|---|---|
| 1259 | 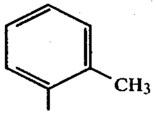 | $C_2H_5OOC$ | $CH_3$ | H |
| 1260 | 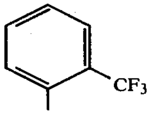 | $C_3H_7OOC$ | $CH_3$ | H |
| 1261 | 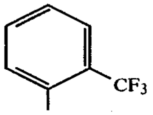 | $(CH_3)_2CHCH_2OOC$ | $CH_3$ | H |
| 1262 | 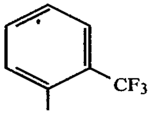 | $(CH_3)_3COOC$ | $CH_3$ | H |
| 1263 | 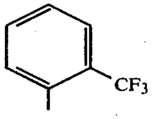 | 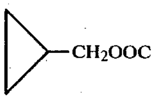 | $CH_3$ | H |
| 1264 | 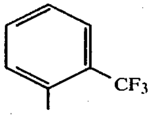 | 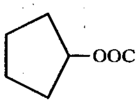 | $CH_3$ | H |
| 1265 | 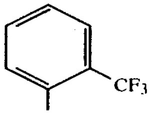 | 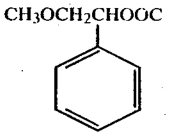 | $CH_3$ | H |

-continued
| | | | | |
|---|---|---|---|---|
| 1266 | 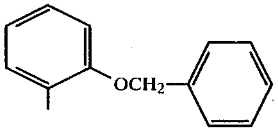 | $C_2H_5OOC$ | $CH_3$ | H |
| 1267 | 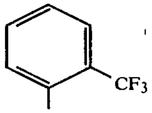 | $O_2N$ | $CH_3$ | H |
| 1268 | 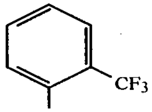 | 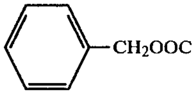 | $CH_3$ | $CH_2OC_2H_5$ |
| 1269 | 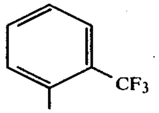 | HOOC | $CH_3$ | $CH_2OC_2H_5$ |
| 1270 | $CH_3$ | $C_2H_5OOC$ | $CH_3$ | H |
| 1271 | 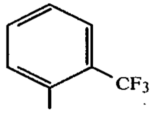 | 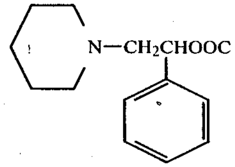 | $CH_3$ | H |
| 1272 | 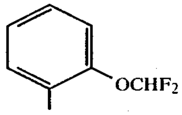 | $C_2H_5OOC$ | $CH_3$ | H |
| 1273 | 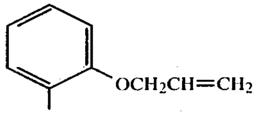 | $C_2H_5OOC$ | $CH_3$ | H |

-continued
| | | | | |
|---|---|---|---|---|
| 1274 | 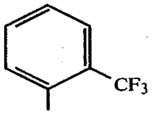 | $FCH_2CH_2OOC$ | $CH_3$ | H |
| 1275 | 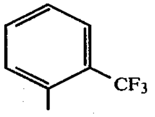 | $CH_3OCH_2CH_2OOC$ | $CH_3$ | H |
| 1276 | 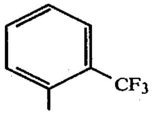 | $ClCH_2CH_2OOC$ | $CH_3$ | H |
| 1277 | 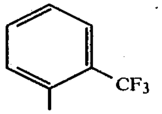 | $CF_3CH_2OOC$ | $CH_3$ | H |
| 1278 | 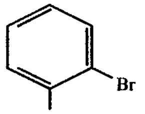 | $C_4H_9OOC$ | $CH_3$ | H |
| 1279 | 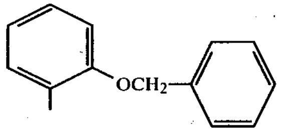 | 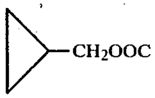 | $CH_3$ | H |
| 1280 | 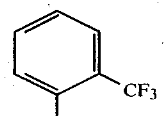 | 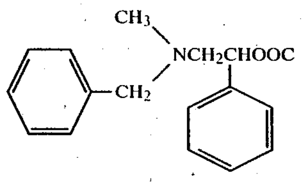 | $CH_3$ | H |

-continued
| | | | | |
|---|---|---|---|---|
| 1281 | 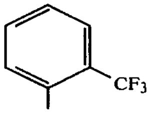 | $CH_3(CH_2)_7OOC$ | $CH_3$ | H |
| 1282 | 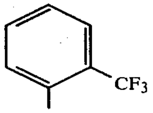 | $CH_3(CH_2)_5OOC$ | $CH_3$ | H |
| 1283 | 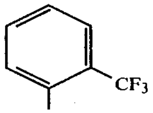 | $CH_2{=}CHCH_2OOC$ | $CH_3$ | H |
| 1284 | 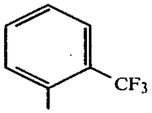 | 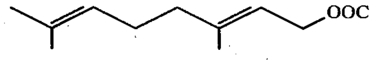 | $CH_3$ | H |
| 1285 | 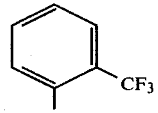 | $CH{\equiv}CCH_2OOC$ | $CH_3$ | H |
| 1286 | 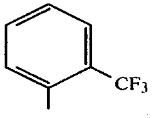 | $CH_3S(CH_2)_2OOC$ | $CH_3$ | H |
| 1287 | 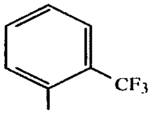 | $CH_3(CH_2)_4OOC$ | $CH_3$ | H |

-continued
| | | | |
|---|---|---|---|
| 1288 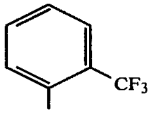 | 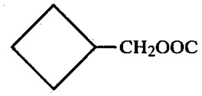 | $CH_3$ | H |
| 1289 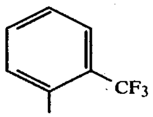 | 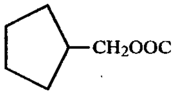 | $CH_3$ | H |
| 1290 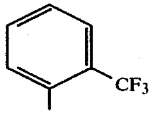 | 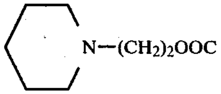 | $CH_3$ | H |
| 1291 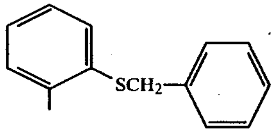 | $C_2H_5OOC$ | $CH_3$ | H |
| 1292 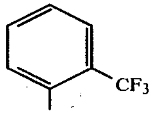 | 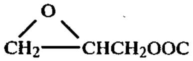 | $CH_3$ | H |
| 1293 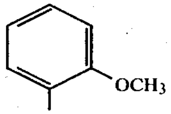 | $C_2H_5OOC$ | $CH_3$ | H |
| 1294 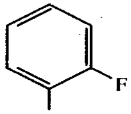 | $C_2H_5OOC$ | $CH_3$ | H |

-continued
| | | | | |
|---|---|---|---|---|
| 1295 | 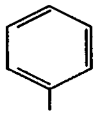 | $CH_3OOC$ | $CH_3$ | H |
| 1296 | 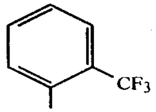 | 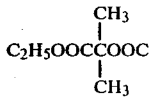 | $CH_3$ | H |
| 1297 | 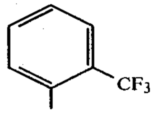 | CN | $CH_3$ | H |
| 1298 | 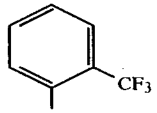 | $C_2H_5OOC$ | $CF_3$ | H |
| 1299 | 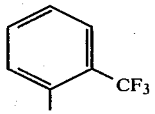 | $CH_3(CH_2)_{15}OOC$ | $CH_3$ | H |
| 1300 | 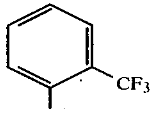 | 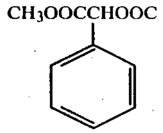 | $CH_3$ | H |
| 1301 | 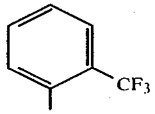 | 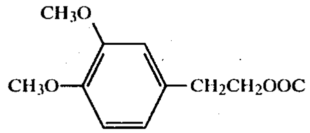 | $CH_3$ | H |

-continued
| | | | | |
|---|---|---|---|---|
| 1302 | 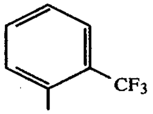 | 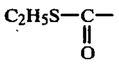 | $CH_3$ | H |
| 1303 | 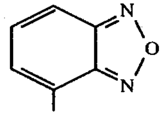 | $O_2N$ | $CH_3$ | H |
| 1304 | 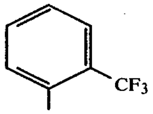 | $C_2H_5OOC$ | Cl | H |
| 1305 | 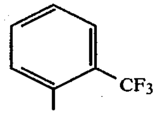 | $C_2H_5OOC$ | $(C_2H_5)_2NCH_2$ | H |
| 1306 | 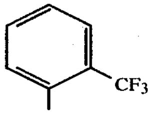 | $C_2H_5OOC$ | $CH_3NHCOOCH_2$ | H |
| 1307 | 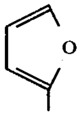 | $C_2H_5OOC$ | $C_3H_7$ | H |
| 1308 | 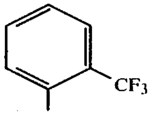 | $CH_3(CH_2)_{21}OOC$ | $CH_3$ | H |

-continued
| | | | | |
|---|---|---|---|---|
| 1309 | 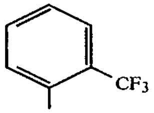 | 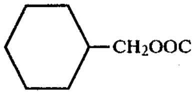 | $CH_3$ | H |
| 1310 | 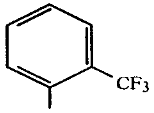 | $(CH_3)_3CCH_2OOC$ | $CH_3$ | H |
| 1311 | 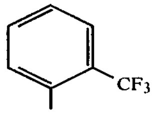 | 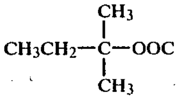 | $CH_3$ | H |
| 1312 | 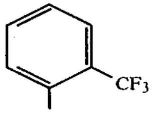 | 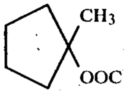 | $CH_3$ | H |
| 1313 | 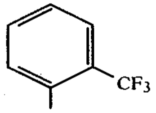 | $C_2H_5OOC$ | $C_3H_7$ | H |
| 1314 | 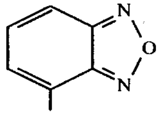 | $C_2H_5OOC$ | $CH_3$ | H |
| 1315 | 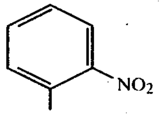 | $C_2H_5OOC$ | $CH_3$ | H |

-continued
| | | | | |
|---|---|---|---|---|
| 1316 | 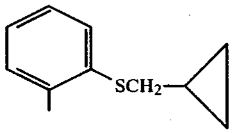 | $C_2H_5OOC$ | $CH_3$ | H |
| 1317 | 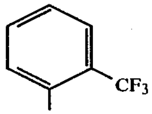 | $CH_3CH_2CHOOC$<br>$CH_3$ | $CH_3$ | H |
| 1318 | 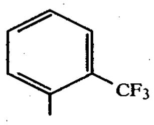 | 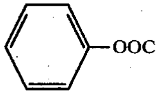 | $CH_3$ | H |
d: decomposition

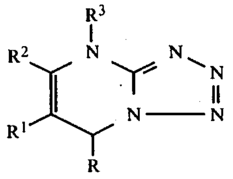
| No. | R | $R^1$ | $R^2$ | $R^3$ |
|---|---|---|---|---|
| 1319 | 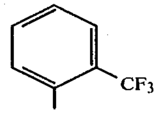 | $C_2H_5OOC$ | $CH_3$ | H |
| 1320 | 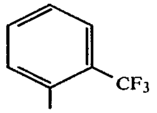 | $C_2H_5OOC$ | $(C_2H_5)_2N$ | H |
| 1321 | 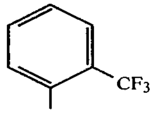 | $C_2H_5OOC$ | $(CH_3)_3C$ | H |
| 1322 | 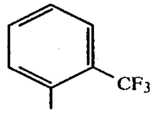 | $C_2H_5OOC$ | $CH_3NHCSOCH_2$ | H |
| 1323 | 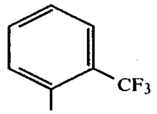 | $C_2H_5OOC$ | $CH_3$ | $CH_3$ |
| 1324 | 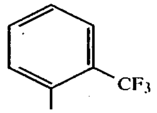 | $C_2H_5OOC$ | $CH_3$ | 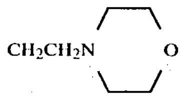 |

-continued
| | | | | |
|---|---|---|---|---|
| 1325 | 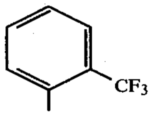 | 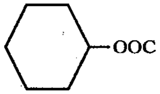 | $CH_3$ | H |
| 1326 | 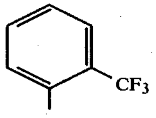 | $C_2H_5OOC$ | $C_2H_5OCH_2$ | H |
| 1327 | 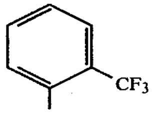 | $C_2H_5OOC$ | $CH_3$ | 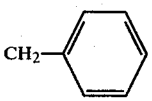 |
| 1328 | 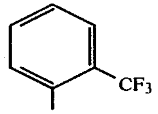 | $C_2H_5OOC$ | 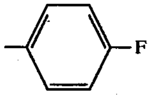 | H |
| 1329 | 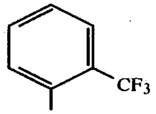 | $H_2NOC$ | $CH_3$ | H |
| 1330 | 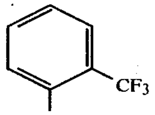 | $H_2NSC$ | $CH_3$ | H |
| 1331 | 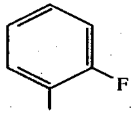 | 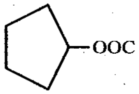 | $CH_3$ | H |

-continued
| | | | | |
|---|---|---|---|---|
| 1332 | 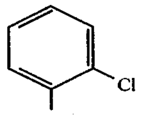 | $(CH_3)_2CHOOC$ | $CH_3$ | H |
| 1333 | 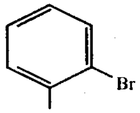 | $(CH_3)_2CHOOC$ | $CH_3$ | H |
| 1334 | 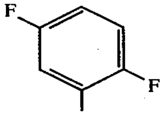 | $(CH_3)_2CHOOC$ | $CH_3$ | H |
| 1335 | 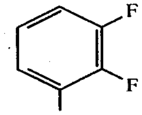 | $(CH_3)_2CHOOC$ | $CH_3$ | H |
| 1336 | 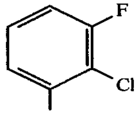 | $(CH_3)_2CHOOC$ | $CH_3$ | H |
| 1337 | 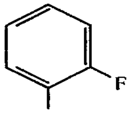 | $CH_3OCH_2CHOOC$ 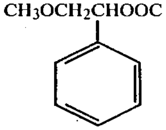 | $CH_3$ | H |
| 1338 | 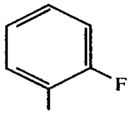 | $(CH_3)_2CHOOC$ | $CH_3$ | H |

-continued
| | | | | |
|---|---|---|---|---|
| 1339 | 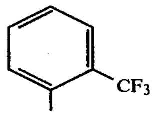 | $(C_2H_5)_2CHOOC$ | $CH_3$ | H |
| 1340 | 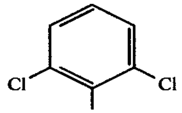 | $C_2H_5OOC$ | $CH_3$ | H |
| 1341 | 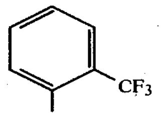 | $(CH_3)_2CHOOC$ | $CH_3$ | $CH_3$ |
| 1342 | 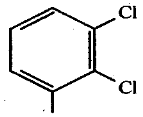 | $C_2H_5OOC$ | $CH_3$ | H |
| 1343 | 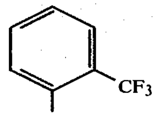 | $(CH_3)_2CHS\underset{\underset{O}{\|}}{C}$ | $CH_3$ | H |
| 1344 | 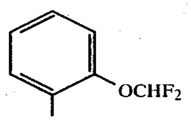 | $CH_3OOC$ | $CH_3$ | H |
| 1345 | 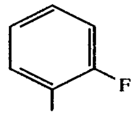 | $C_3H_7OOC$ | $CH_3$ | H |

-continued
| | | | | |
|---|---|---|---|---|
| 1346 | 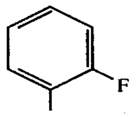 | $(CH_3)_3COOC$ | $CH_3$ | H |
| 1347 | 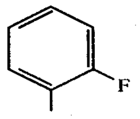 | $(CH_3)_3COOC$ | $CH_3$ | H |
| 1348 | 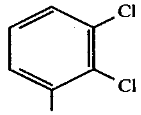 | $(CH_3)_3COOC$ | $CH_3$ | H |
| 1349 | 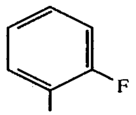 | $(CH_3)_2CHCH_2OOC$ | $CH_3$ | H |
| 1350 | 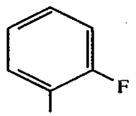 | $C_4H_9OOC$ | $CH_3$ | H |
| 1351 | 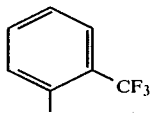 | $(CH_3)_2NCH_2CH_2OOC$ | $CH_3$ | H |
| 1352 | 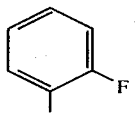 | $(CH_3)_2CHOOC$ | $C_2H_5$ | H |

-continued
| | | | | |
|---|---|---|---|---|
| 1353 | 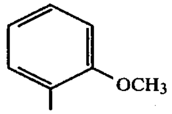 | $(CH_3)_2CHOOC$ | $CH_3$ | H |
| 1354 | 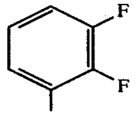 | $C_2H_5OOC$ | $CH_3$ | H |
| 1355 | 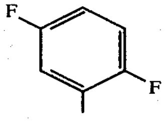 | $C_2H_5OOC$ | $CH_3$ | H |
| 1356 | 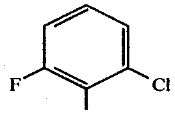 | $C_2H_5OOC$ | $CH_3$ | H |
| 1357 | 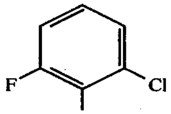 | $(CH_3)_2CHOOC$ | $CH_3$ | H |
| 1358 | 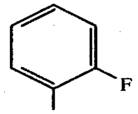 | $(CH_3)_2CHOOC$ | $CH(CH_3)_2$ | H |
| 1359 | 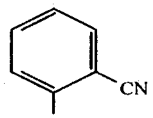 | $(CH_3)_2CHOOC$ | $CH_3$ | H |

-continued
| | | | | |
|---|---|---|---|---|
| 1360 | 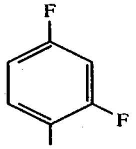 | $C_2H_5OOC$ | $CH_3$ | H |
| 1361 | 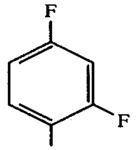 | $(CH_3)_2CHOOC$ | $CH_3$ | H |
| 1362 | 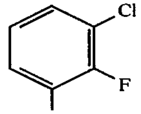 | $C_2H_5OOC$ | $CH_3$ | H |
| 1363 | 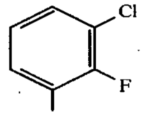 | $(CH_3)_2CHOOC$ | $CH_3$ | H |
| 1364 | 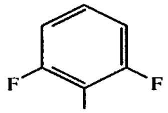 | $C_2H_5OOC$ | $CH_3$ | H |
| 1365 | 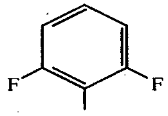 | $(CH_3)_2CHOOC$ | $CH_3$ | H |
| 1366 | 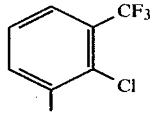 | $C_2H_5OOC$ | $CH_3$ | H |

-continued
| | | | | |
|---|---|---|---|---|
| 1367 | 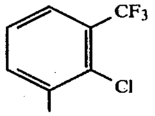 | $(CH_3)_2CHOOC$ | $CH_3$ | H |
| 1368 | 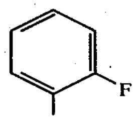 | $(CH_3)_2CHOOC$ | $CH_2OH$ | H |
| 1369 | 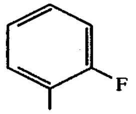 | $(CH_3)_2CHOOC$ | $C_4H_9$ | H |
| 1370 | 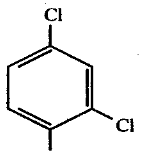 | $(CH_3)_2CHOOC$ | $CH_3$ | H |
| 1371 | 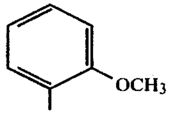 | $(CH_3)_2CHOOC$ | $CH_3$ | H |
| 1372 | 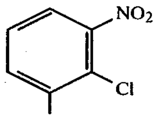 | $C_2H_5OOC$ | $CH_3$ | H |
| 1373 | 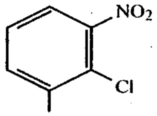 | $(CH_3)_2CHOOC$ | $CH_3$ | H |

-continued
| | | | | |
|---|---|---|---|---|
| 1374 | 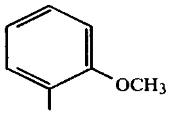 | $(CH_3)_2CHCH_2OOC$ | $CH_3$ | H |
| 1375 | 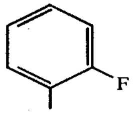 | $(CH_3)_2CHOOC$ | $CH_3$ | H |
| 1376 | 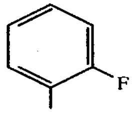 | $(CH_3)_2CHOOC$ | $CH_2F$ | H |
| 1377 | 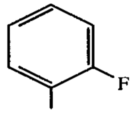 | $(CH_3)_2CHOOC$ | $CH_2CH_2OH$ | H |
| 1378 | 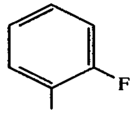 | $(CH_3)_2CHOOC$ | $(CH_2)_3OH$ | H |
| 1379 | 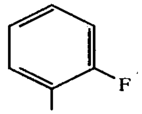 | $C_2H_5OOC$ | 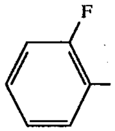 | H |
| 1380 | 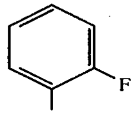 | CN | $CH_3$ | H |

-continued
| | | | | |
|---|---|---|---|---|
| 1381 | 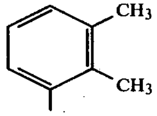 | $(CH_3)_2CHOOC$ | $CH_3$ | H |
| 1382 | 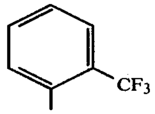 | $(CH_3)_2CHOOC$ | $C_4H_9$ | H |
| 1384 | 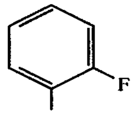 | $(CH_3)_2CHOOC$ | $CH_2OCOCH_3$ | H |
| 1385 | 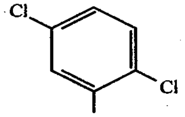 | $(CH_3)_2CHOOC$ | $CH_3$ | H |
| 1386 | 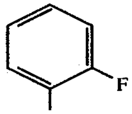 | $(CH_3)_2CHOOC$ | $CH_2Cl$ | H |
| 1387 | 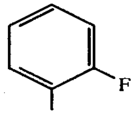 | $(CH_3)_2CHOOC$ | $CH_2N(C_2H_5)_2$ | H |
| 1387 | 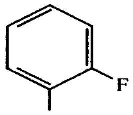 | 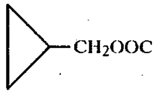 | $CH_3$ | H |

-continued
| | | | | |
|---|---|---|---|---|
| 1388 | 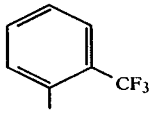 | $(CH_3)_2CHOOC$ | $CH_3$ | $COOC_2H_5$ |
| 1389 | 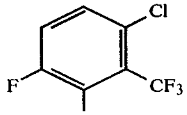 | $C_2H_5OOC$ | $CH_3$ | H |
| 1390 | 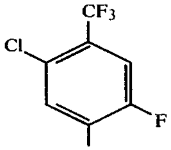 | $(CH_3)_2CHOOC$ | $CH_3$ | H |
| 1391 | 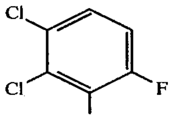 | $C_2H_5OOC$ | $CH_3$ | H |
| 1392 | 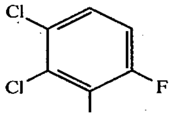 | $(CH_3)_2CHOOC$ | $CH_3$ | H |
| 1393 | 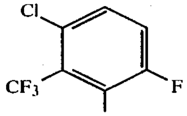 | $(CH_3)_2CHOOC$ | $CH_3$ | H |
| 1394 | 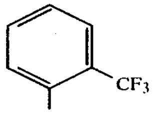 | $(ClCH_2)_2CHOOC$ | $CH_3$ | H |

-continued
| | | | | |
|---|---|---|---|---|
| 1395 | 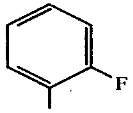 | $ClCH_2CH_2OOC$ | $CH_3$ | H |
| 1396 | 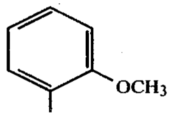 | 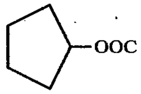 | $CH_3$ | H |
| 1397 | 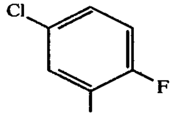 | $(CH_3)_2CHOOC$ | $CH_3$ | H |

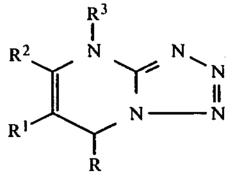
| No. | R | $R^1$ | $R^2$ | $R^3$ |
|---|---|---|---|---|
| 1398 | 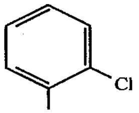 | 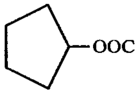 | $CH_3$ | H |
| 1399 | 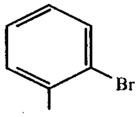 | 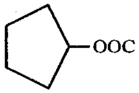 | $CH_3$ | H |
| 1400 | 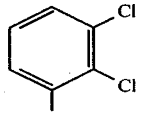 | $(CH_3)_3COOC$ | $CH_3$ | H |
| 1401 | 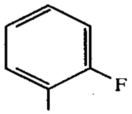 | $(CH_3)_2CHOOC$ | $Cl(CH_2)_3$ | H |
| 1402 | 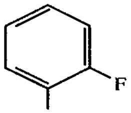 | $(CH_3)_2CHOOC$ | $CH_3COO(CH_2)_3$ | H |
| 1403 | 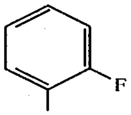 | 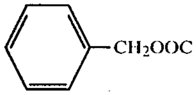 | $CH_3COO(CH_2)_3$ | H |

-continued
| | | | | |
|---|---|---|---|---|
| 1404 | 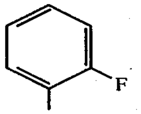 | 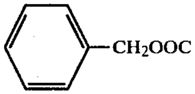 | $HO(CH_2)_3$ | H |
| 1405 | 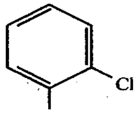 | $(CH_3)_3COOC$ | $CH_3$ | H |
| 1406 | 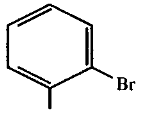 | $(CH_3)_3COOC$ | $CH_3$ | H |
| 1407 | 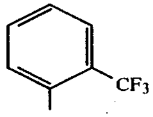 | $ClCH_2CH_2CH_2CH_2OOC$ | $CH_3$ | H |
| 1408 | 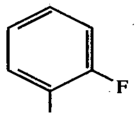 | $(ClCH_2)_2CHOOC$ | $CH_3$ | H |
| 1409 | 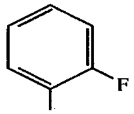 | $(CH_3)_2CHOOC$ | $CH_3COOCH_2$ | H |
| 1410 | 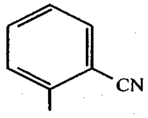 | $(CH_3)_3COOC$ | $CH_3$ | H |

-continued
| | | | | |
|---|---|---|---|---|
| 1411 | 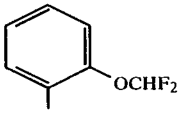 | $(CH_3)_3COOC$ | $CH_3$ | H |
| 1412 | 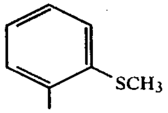 | $(CH_3)_2CHOOC$ | $CH_3$ | H |
| 1413 | 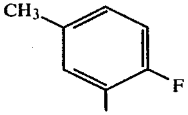 | $(CH_3)_2CHOOC$ | $CH_3$ | H |
| 1414 | 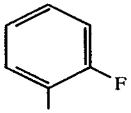 | 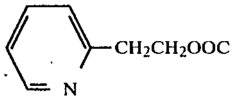 | $CH_3$ | H |
| 1415 | 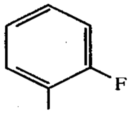 | 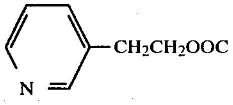 | $CH_3$ | H |
| 1416 | 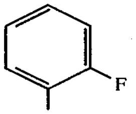 | 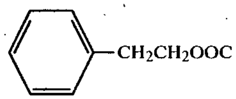 | $CH_3$ | H |
| 1417 | 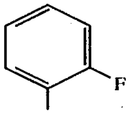 | 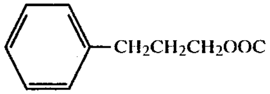 | $CH_3$ | H |

-continued
| | | | |
|---|---|---|---|
| 1418 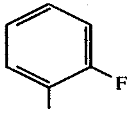 | $C_2H_5OOC$ | $H_2N$ | H |
| 1419 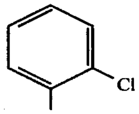 | H | $CH_3$ | H |
| 1420 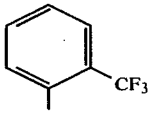 | $CH_3OCH_2CHOOC$ 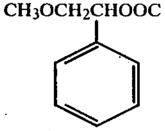 | $CH_3$ | H |
| 1421 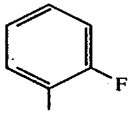 | $(CH_3)_2CHOOC$ | 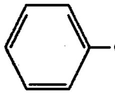 $CH_2OCH_2CH_2$ | H |
| 1422 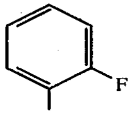 | $(CH_3)_2CHOOC$ | $CH_3$ 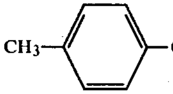 $O(CH_2)_3$ | H |
| 1423 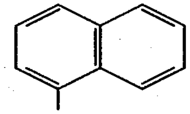 | $(CH_3)_2CHOOC$ | $CH_3$ | H |
| 1424 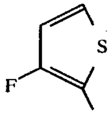 | $(CH_3)_2CHOOC$ | $CH_3$ | H |

-continued
| | | | | |
|---|---|---|---|---|
| 1425 | 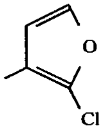 | $C_2H_5OOC$ | $CH_3$ | H |
| 1426 | 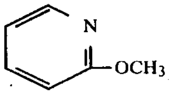 | $(CH_3)_2CHOOC$ | $CH_3$ | H |
| 1427 | 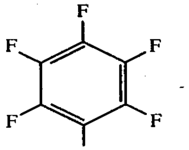 | $(CH_3)_2CHOOC$ | $CH_3$ | H |
| 1428 | 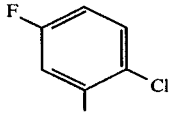 | $(CH_3)_3COOC$ | $CH_3$ | H |
| 1429 | 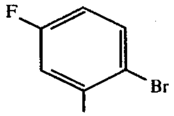 | $CH_3CH_2CH_2OOC$ | $CH_3$ | H |
| 1430 | 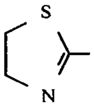 | $CH_3OOC$ | $CH_3$ | H |
| 1431 | 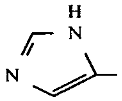 | 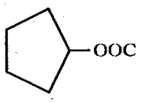 | $CH_3$ | H |

-continued
| | | | |
|---|---|---|---|
| 1432 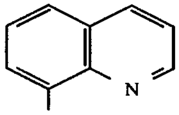 | $(CH_3)_2CHOOC$ | $CH_3$ | H |
| 1433 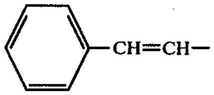 | $(CH_3)_2CHOOC$ | $CH_3$ | H |
| 1434 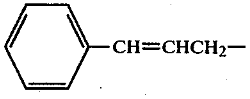 | $(CH_3)_3COOC$ | $CH_3$ | H |
| 1435 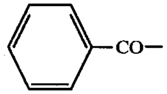 | $C_2H_5OOC$ | $CH_3$ | H |
| 1436 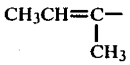 | $(CH_3)_2CHOOC$ | $CH_3$ | H |
| 1437 $CH{\equiv}C{-}CH_2{-}$ | $(CH_3)_3COOC$ | $CH_3$ | H |
| 1438 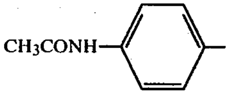 | $C_2H_5OOC$ | $CH_3$ | H |
| 1439 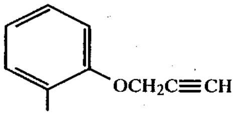 | $(CH_3)_2CHOOC$ | $CH_3$ | H |
| 1440 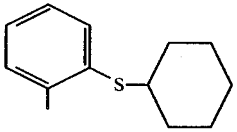 | $C_2H_5OOC$ | $CH_3$ | H |

-continued
| | | | | |
|---|---|---|---|---|
| 1441 | 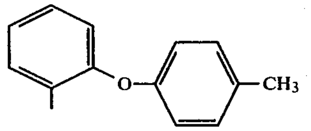 | $CH_3CH_2CH_2OOC$ | $CH_3$ | H |
| 1442 | 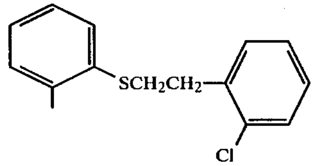 | $CH_3(CH_2)_3OOC$ | $CH_3$ | H |
| 1443 | 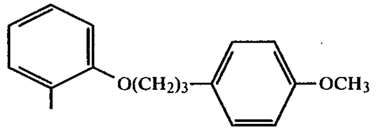 | 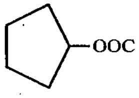 | $CH_3$ | H |
| 1444 | 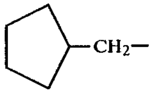 | $(CH_3)_2CHOOC$ | $CH_3$ | H |
| 1445 | 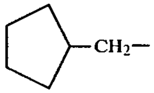 | $CH_3OOC$ | $CH_3$ | H |
| 1446 | 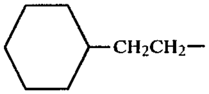 | 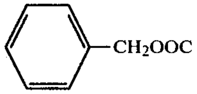 | $CH_3$ | H |
| 1447 | 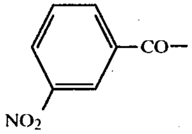 | $CH_3OCH_2CH_2OOC$ | $CH_3$ | H |

-continued
| | | | | |
|---|---|---|---|---|
| 1448 | 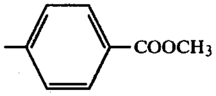 | $CH_3OOC$ | $CH_3$ | H |
| 1449 | 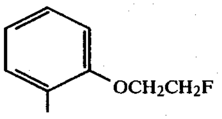 | $(CH_3)_2CHOOC$ | $CH_3$ | H |
| 1450 | 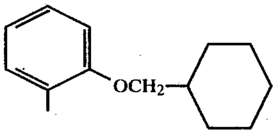 | 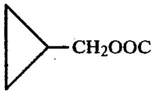 | $CH_3$ | H |
| 1451 | 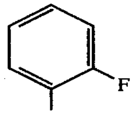 | $(CH_3)_2CHOSC$ | $CH_3$ | H |
| 1452 | 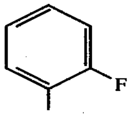 | $(CH_3)_2CHSSC$ | $CH_3$ | H |
| 1453 | 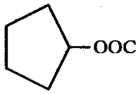 | $H_2NOC$ | $CH_3$ | H |
| 1454 | 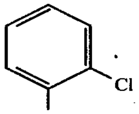 | 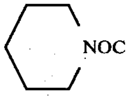 | $CH_3$ | H |
| 1455 | 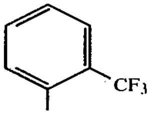 | $(CH_3)_2CHNHOC$ | $CH_3$ | H |

-continued
| | | | |
|---|---|---|---|
| 1456 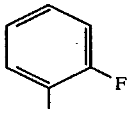 | $(C_2H_5)_2NOC$ | $CH_3$ | H |
| 1457 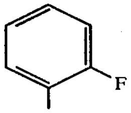 | $H_2NSC$ | $CH_3$ | H |
| 1458 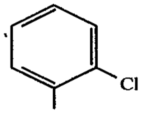 | 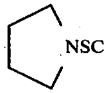 | $CH_3$ | H |
| 1459 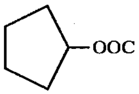 | $(CH_3)_3CNHSC$ | $CH_3$ | H |
| 1460 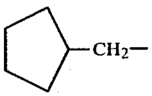 | 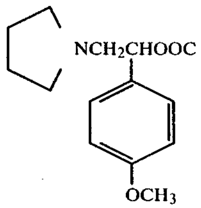 | $CH_3$ | H |
| 1461 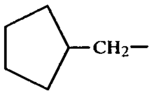 | 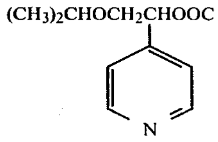 | $CH_3$ | H |
| 1462 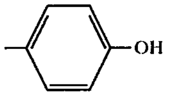 | 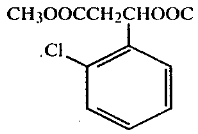 | $CH_3$ | H |

-continued
| | | | | |
|---|---|---|---|---|
| 1463 | 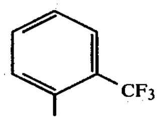 | 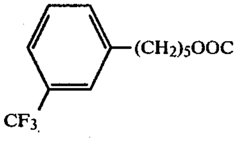 | $CH_3$ | H |
| 1464 | 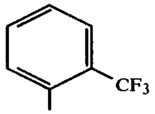 | $C_2H_5OOC$ | 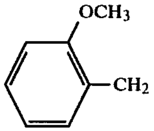 | H |
| 1465 | 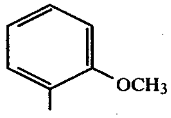 | $CH_3OOC$ | 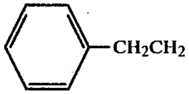 | H |
| 1466 | 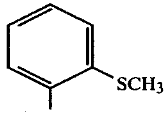 | $(CH_3)_2CHOOC$ | 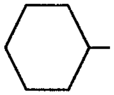 | H |
| 1467 | 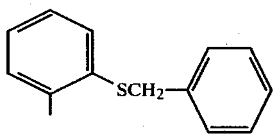 | $CH_3(CH_2)_2OOC$ | 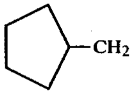 | H |
| 1468 | 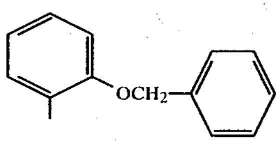 | $CH_3(CH_2)_3OOC$ | $H_2NCH_2CH_2$ | H |
| 1469 | 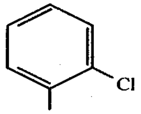 | $CH_3(CH_2)_3OOC$ | $CH_3CONHCH_2CH_2$ | H |

-continued
| | | | | |
|---|---|---|---|---|
| 1470 | 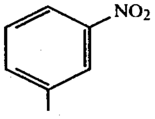 | $(CH_3)_2CHCH_2OOC$ | $HOCH_2CH_2OCH_2$ | H |
| 1471 | 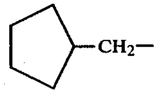 | $C_2H_5OOC$ | $H_2N(CH_2)_2OCH_2$ | H |
| 1472 | 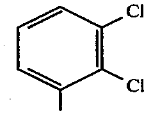 | $CH_3OOC$ | 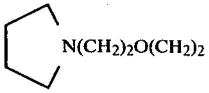 | H |
| 1473 | 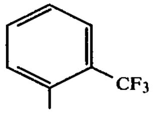 | $(CH_3)_2CHOOC$ | $CH_3$ | $C_3H_7$ |
| 1474 | 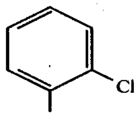 | $(CH_3)_2CHOOC$ | $CH_3$ | 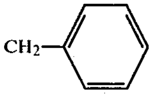 |
| 1475 | 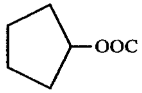 | $C_3H_7OOC$ | $CH_3$ | 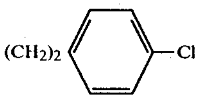 |
| 1476 | 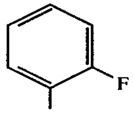 | 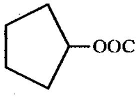 | $CH_3$ | 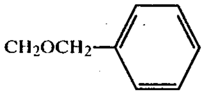 |
| 1477 | 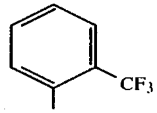 | $CH_3(CH_2)_3OOC$ | $CH_3$ | $COCH_3$ |

-continued
| | | | | |
|---|---|---|---|---|
| 1478 | 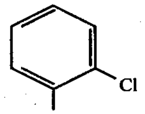 | $(CH_3)_2CHOOC$ | $CH_3$ | $CH_2CH_2Cl$ |
| 1479 | 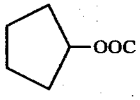 | $(CH_3)_3COOC$ | $CH_3$ | $(CH_2)_3OSO_2CH_3$ |
| 1480 | 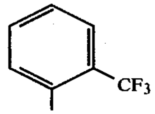 | 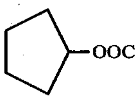 | $CH_3$ | $(CH_2)_4OSO_2$ 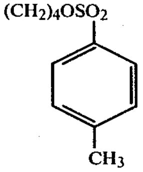 |
| 1481 | 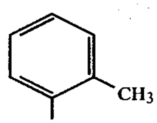 | $C_2H_5OOC$ | $CH_3$ | $CH_2CH_2OH$ |
| 1482 | 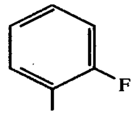 | $(CH_3)_2CHOOC$ | $CH_3$ | $CH_2CH_2N$ 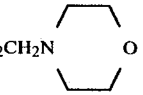 |
| 1483 | 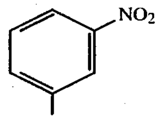 | $CH_3OOC$ | $CH_3$ | $(CH_2)_3N(C_2H_5)_2$ |

EXAMPLE 1484

A mixture of 0.34 g of 5-amino-1,2,3-triazole and 1.0 g of isopropyl α-acetyl-2-fluorocinnamate in 10 ml of acetonitrile is refluxed under heating for 4 hours. The solvent is distilled off under reduced pressure and the residue is crystallized from a mixture of diisopropyl ether and dichloromethane. The resulting crystals are recrystallized from a mixture of methanol, diisopropyl ether and hexane to give 0.3 g of 7-(2-fluorophenyl)-6-isopropoxycarbonyl-5-methyl-4,7-dihydro-1,2,3-triazolo[1,5-a]pyrimidine, melting at 137°–139° C., as colorless crystals.

The compounds summarized in the following tables can also be prepared in a similar manner as the above example.

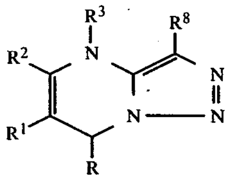
| No. | R | $R^1$ | $R^2$ | $R^3$ | $R^8$ |
|---|---|---|---|---|---|
| 1485 | 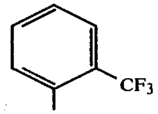 | $(CH_3)_2CHOOC$ | $CH_3$ | H | H |
| 1486 | 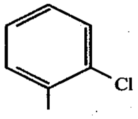 | $(CH_3)_2CHOOC$ | $CH_3$ | H | H |
| 1487 | 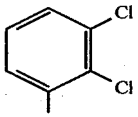 | $C_3H_7OOC$ | $CH_3$ | H | H |
| 1488 | 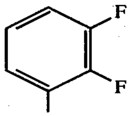 | $(CH_3)_2CHOOC$ | $CH_3$ | H | H |
| 1489 | 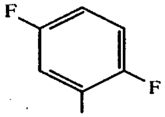 | $(CH_3)_2CHOOC$ | $CH_3$ | H | H |
| 1490 | 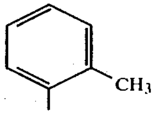 | $(CH_3)_2CHCH_2OOC$ | $CH_3$ | H | H |

-continued
| | | | | | |
|---|---|---|---|---|---|
| 1491 | 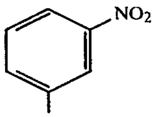 | $CH_3OOC$ | $CH_3$ | H | H |
| 1492 | 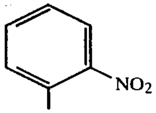 | $C_2H_5OOC$ | $CH_3$ | H | H |
| 1493 | 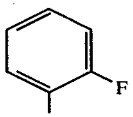 | 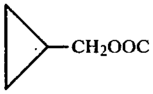 | $CH_3$ | H | H |
| 1494 | 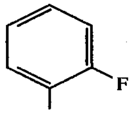 | 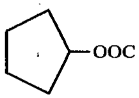 | $CH_3$ | H | H |
| 1495 | 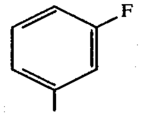 | $FCH_2CH_2OOC$ | $CH_3$ | H | H |
| 1496 | 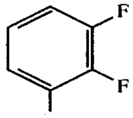 | $(CH_3)_2CHOOC$ | $CH_3$ | H | CN |
| 1497 | 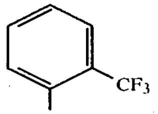 | $(CH_3)_3COOC$ | $CH_3$ | H | H |

-continued
| | | | | | |
|---|---|---|---|---|---|
| 1498 | 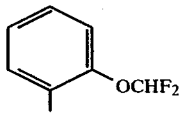 | $(CH_3)_2CHOOC$ | $CH_3$ | H | H |
| 1499 | 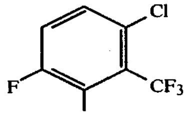 | $C_2H_5OOC$ | $CH_3$ | H | H |
| 1500 | 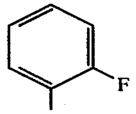 | $(CH_3)_2CHOOC$ | $CH_2OH$ | H | H |
| 1501 | 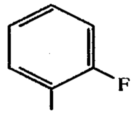 | $(CH_3)_2CHCH_2OOC$ | $CH_3$ | H | H |
| 1502 | 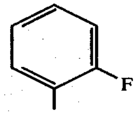 | $C_2H_5OOC$ | $CH_3$ | H | $COOC_2H_5$ |
| 1503 | 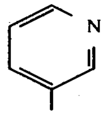 | $CH_3(CH_2)_3OOC$ | $CH_3$ | H | H |
| 1504 | 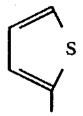 | $(C_2H_5)_2CHOOC$ | $CH_3$ | H | H |

-continued
| | | | | | |
|---|---|---|---|---|---|
| 1505 | 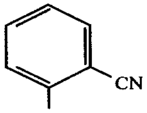 | 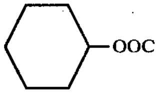 | $CH_3$ | H | H |
| 1506 | 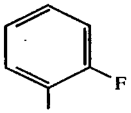 | 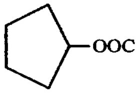 | $CH_3$ | H | Cl |
| 1507 | 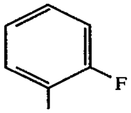 | 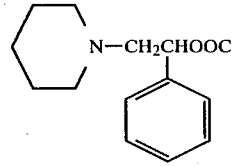 | $CH_3$ | H | H |
| 1508 | 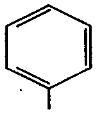 | $(CH_3)_2CHOOC$ | $CH_3$ | H | H |
| 1509 | 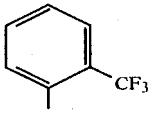 | 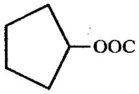 | $CH_2F$ | H | H |
| 1510 | 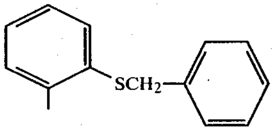 | $(CH_3)_3COOC$ | $CH_3$ | H | H |
| 1511 | 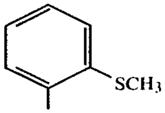 | 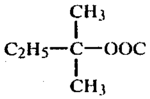 | $CH_3$ | H | H |

-continued
| | | | | | |
|---|---|---|---|---|---|
| 1512 | 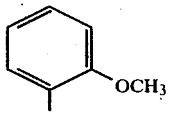 | $CH_3(CH_2)_5OOC$ | $CH_3$ | H | H |
| 1513 | 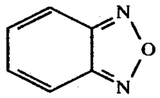 | $C_2H_5OOC$ | $CH_3$ | H | H |
| 1514 | 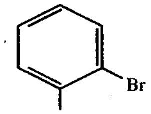 | N≡C | $C_2H_5$ | H | H |
| 1515 | 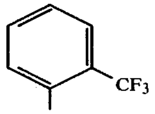 | $CH_3OCH_2CH_2OOC$ | $CH_3$ | H | $CH_3$ |
| 1516 | 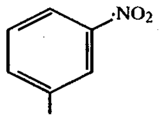 | $C_2H_5OOC$ | $CH_2N(C_2H_5)_2$ | H | H |

EXAMPLE 1600

To a solution of 3.0 g of isopropyl 4-[2-(phthalimido)-ethoxy]-3-oxobutylate and 1.5 g of 2,3-difluorobenzaldehyde in 30 ml of benzene is added two drops of acetic acid and piperidine respectively and the mixture is refluxed for 3 hours with Dean-Stark trap. The solvent is distilled off and to the residue are added 1.1 g of 3-amino-4-cyanopyrazole and 10 ml of dimethylformamide, and then heated at 100° C. for 6 hours. After the solvent is distilled off, the residue is purified by column chromatography on silica gel and crystallized from ethanol to give 1.65 g of isopropyl 3-cyano-7-(2,3-difluorophenyl)-5-[2-(phthalimido)ethoxymethyl]-4,7-dihydropyrazolo[1,5-a]pyrimidine-6-carboxylate, melting at 176°-177° C.

To a solution of 1.3 g of isopropyl 3-cyano-7-(2,3-difluorophenyl)-5-[2-(phthalimido)ethoxymethyl]-4,7-dihydropyrazolo[1,5-a]pyrimidine-6-carboxylate in a mixed solvent of 12 ml of methanol and 12 ml of chloroform is added 142 μl of hydrazine hydrate and the mixture is refluxed at 50° C. for 5 hours. After the solvent is distilled off, to the residue is added aqueous sodium hydrogencarbonate and then extracted with ethyl acetate. The organic layer is washed with water, dried over sodium sulfate and ethanolic hydrochloric acid is added to convert into hydrochloride. The obtained crystals are recrystallized from methanol to give 0.4 g of isopropyl 5-(2-aminoethoxymethyl)-3-cyano-7-(2,3-difluorophenyl)-4,7-dihydropyrazolo[1,5-a]pyrimidine-6-carboxylate hydrochloride ¼ hydrate.

Melting point: 231°-233° C. with decomposition.

Mass spectrum: m/z 417.

Thin layer chromatography: Rf=0.26 (Merck ART 5715, chloroform: methanol=4:1).

The foregoing isopropyl 3-cyano-7-(2,3-difluorophenyl)-5-[2-(phthalimido)ethoxymethyl]-4,7-dihydropyrazolo[1,5-a]-pyrimidine-6-carboxylate is subjected to an optically active column (YMC-Pack A-103) and eluted with a mixture of n-hexane-ethyl acetate-ethanol (55:45:1) to purify and separate it to give two optical isomers. Each optical isomer is treated in a similar manner as mentioned above to give d-form [melting at 217°-218° C. with decomposition, $[\alpha]_D^{20}=+68°$ (c=0.25, ethanol)] and l-form [melting at 217°-218° C. with decomposition, $[\alpha]_D^{20}=-70°$ (c=0.25, ethanol)] of isopropyl 5-(2-aminoethoxymethyl)-3-cyano-7-(2,3-difluorophenyl)-4,7-dihydropyrazolo[1,5-a]pyrimidine-6-carboxylate hydrochloride, respectively.

Isopropyl 4-[2-(phthalimido)ethoxy]-3-oxobutylate, as the starting compound, is prepared as follows:

To a suspension of 6 g of 2-(phthalimido)ethoxyacetic acid in dichloromethane are added 2.05 ml of thionyl chloride and 3 drops of dimethylformamide, and the mixture is stirred for 2 days. The solvent is distilled off to give 2-(phthalimido)ethoxyacetyl chloride. A solution of 2-(phthalimido)ethoxyacetyl chloride in 10 ml of dichloromethane is added dropwise to a solution, maintained at −5° C., of 3.6 g of Meldrum's acid in 20 ml of dichloromethane and 4.3 ml of pyridine. Then, the mixture is stirred overnight at room temperature. To the resultant mixture is added 2 normal hydrochloric acid and the dichloromethane layer is extracted. The extract is washed with sodium chloride solution three times, dried over sodium sulfate and the solvent is distilled off. To the residue is added 50 ml of isopropyl alcohol and refluxed for 5 hours. The solvent is distilled off and the residue is purified by column chromatography on silica gel to give 3.7 g of isopropyl 4-[2-(phthalimido)ethoxy]-3-oxobutylate.

Although the present invention has been adequately discussed in the foregoing specification and examples included therein, one readily recognizes that various changes and modifications may be made without departing from the spirit and scope thereof.

What is claimed is:

1. A polyazaheterocycle compound of the formula:

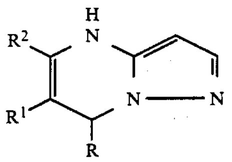

or a pharmaceutically acceptable salt thereof, wherein R is hydrogen, $C_{1-4}$ alkyl, $C_{3-6}$ cycloakyl, furyl, thienyl, pyridyl or phenyl which may be optionally substituted by one or two substituents selected from the group consisting of halogen, $C_{1-4}$ alkyl, trifluoromethyl, $C_{1-4}$ alkoxy, phenyl-$C_{1-3}$ alkyloxy, $C_{1-4}$ alkylthio, phenyl-$C_{1-3}$ alkylthio, acyl, hydroxy, amino, nitro and cyano;

$R^1$ is hydrogen, cyano, carbamoyl, carboxyl, $C_{1-4}$ alkoxycarbonyl which may be optionally substituted in the alkoxy moiety by one or two substituents selected from the group consisting of $C_{1-4}$ alkoxy, cyano, a group represented by the formula: —N ($Ra^1$) ($Rb^1$) (wherein each of $Ra^1$ and $Rb^1$ is $C_{1-4}$ alkyl or phenyl-$C_{1-3}$ alkyl, or $Ra^1$ and $Rb^1$ together with the adjacent nitrogen atom form a 5- to 7-membered heterocycle selected from the group consisting of pyrrolidine, piperidine, morpholine, piperazine, N-methylpiperzine, N-(2-hydroxymethyl)-piperazine, azepine and diazepine), nitro, phenyl, thienyl, furyl and pyridyl, or alkanoyl;

$R^2$ is $C_{1-4}$ alkyl, hydroxy-$C_{1-4}$ alkyl, acetoxy-$C_{1-4}$ alkyl, halo-$C_{1-4}$ alkyl, dihalo-$C_{1-4}$ alkyl, trifluoromethyl, $C_{-1-4}$ alkoxy-$C_{1-4}$ alkyl, di-$C_{1-4}$ alkoxy-methyl, $C_{1-4}$ alkylcarbamoyloxy-$C_{1-4}$ alkyl, $C_{1-4}$ alkyl-thiocarbamoyloxy-$C_{1-4}$ alkyl, formyl, hydroxyiminomethyl or cyano.

2. The compound of claim 1:
7-(2-fluorophenyl)-6-isopropoxycarbonyl-5-methyl-4,7-dihydropyrazolo[1,5-a]pyrimidine.

3. The compound of claim 1:
7-(2,5-difluorophenyl)-6-isopropoxycarbonyl-5-methyl-4,7-dihydropyrazolo[1,5-a]pyrimidine.

4. The compound of claim 1:
6-ethoxycarbonyl-5-methyl-7-(2-trifluoromethylphenyl)-4,7-dihydropyrazolo[1,5-a]pyrimidine.

5. The compound of claim 1:
6-isopropoxycarbonyl-5-methyl-7-(2-trifluoromethylphenyl)-4,7-dihydropyrazolo[1,5-a]pyrimidine.

6. The compound of claim 1:
6-tert-butoxycarbonyl-5-methyl-7-(2-trifluoromethylphenyl)-4,7-dihydropyrazolo[1,5-a]pyrimidine.

7. The compound of claim 1:
7-(2-chlorophenyl)-6-isopropoxycarbonyl-5-methyl-4,7-dihydropyrazolo[1,5-a]pyrimidine.

8. The compound of claim 1:
7-(2-bromophenyl)-6-isopropoxycarbonyl-5-methyl-4,7-dihydropyrazolo[1,5-a]pyrimidine.

9. The compound of claim 1:
7-(2-chloro-3-fluorophenyl)-6-isopropoxycarbonyl-5-methyl-4,7-dihydropyrazolo[1,5-a]pyrimidine.

10. The compound of claim 1:
6-isobutoxycarbonyl-5-methyl-7-(2-trifluoromethyl-phenyl)-4,7-dihydropyrazolo[1,5-a]pyrimidine.

11. The compound of claim 1:
1-phenyl-2-piperidinoethyl 5-methyl-7-(3-nitrophenyl)-4,7-dihydropyrozolo[1,5-a]pyrimidine-6-carboxylate.

12. The compound of claim 1:
7-(2-benzylthiophenyl)-6-ethoxycarbonyl-5-methyl-4,7-dihydropyrazolo[1,5-a]pyrimidine.

13. The compound of claim 1:

6-isopropoxycarbonyl-5-methyl-7-(2-methylphenyl)-4,7-dihydropyrazolo[1,5-a]pyrimidine.

14. The compound of claim 1:
7-(2,6-difluorophenyl)-6-isopropoxycarbonyl-5-methyl-4,7-dihydropyrazolo[1,5-a]pyrimidine.

15. The compound of claim 1:
6-ethoxycarbonyl-5-methyl-7-(2-trifluoromethyl-phenyl)-4,7-dihydropyrazolo[1,5-a]pyrimidine.

16. A pharmaceutical composition comprising a therapeutically effective amount of the compound of claim 1 and a pharmaceutically acceptable carrier thereof.

* * * * *